(12) United States Patent
Boger

(10) Patent No.: US 6,548,530 B1
(45) Date of Patent: Apr. 15, 2003

(54) CBI ANALOGS OF CC-1065 AND THE DUOCARMYCINS

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/051,264

(22) PCT Filed: Oct. 3, 1996

(86) PCT No.: PCT/US96/16481

§ 371 (c)(1),
(2), (4) Date: Oct. 2, 1998

(87) PCT Pub. No.: WO97/12862

PCT Pub. Date: Apr. 10, 1997

Related U.S. Application Data

(60) Provisional application No. 60/004,752, filed on Oct. 3, 1995.

(51) Int. Cl.[7] .................... A61K 31/403; C07D 405/14; C07D 409/14
(52) U.S. Cl. .................... 514/410; 548/218; 548/302.1; 548/420
(58) Field of Search .............................. 548/218, 302.1, 548/420; 514/410

(56) References Cited

FOREIGN PATENT DOCUMENTS

WO          97/44000          11/1997

OTHER PUBLICATIONS

Boger et al., J. Am. Chem. Soc., (Sep. 7, 1994), vol. 116, No. 18, pp. 7996–8006.*
Boger et al., J. Am. Chem. Soc., (Jun. 15, 1994), vol. 116, No. 12, pp. 5523–5524.*
Aristoff et al., J. Med. Chem., (1993), vol. 36, No. 14, pp. 1956–1963.*
Boger et al., J. Am. Chem. Soc., (Jul. 1, 1992), vol. 114, No. 14, pp. 5487–5496.*
Boger et al., J. Org. Chem., (1991), vol. 56, No. 8, p. 2946.*
Boger et al., J. Org. Chem., (1990), vol. 55, No. 23, pp. 5823–5832.*
Boger, et al., "CBI–CDPBO and CBI–CDPBI: CC–1065 Analogs Containing Deep–seated Modifications in the DNA Binding Subunit", Bioorg. & Med. Chem. 3 (6): 761–775 Jun. (1995).
Boger, et al., "A Potent, Simple Derivative of an Analog of the CC–1065 Alkylation Subunit", Bioorg. & Med. Chem. Letters 1 (1): 55–58 (1991).
Boger, et al., "Synthesis and Preliminary Evaluation of (+)–CBI–Indole: An Enhanced Functional Analog of (+)–CC–1065", Bioorg. & Med. Chem. Letters 1 (2): 115–120 (1991).
Suzuki, "Benzofuran Derivatvies. II. Synthesis of 2,3–Dihydrobenzofurans from Ethyl 2–Acylphenoxyacetates", Bull. Chem. Soc. Jpn. 58: 2821–2825 (1985).
Epstein, et al., "Studies Concerning the Infrared Spectra of Some Substituted Benzofuran Derivatives", J. Org. Chem. 30 : 1246–1247 (1965).
Boger, et al., "CC–1065 CBI Analogs: an Example of Enhancement of DNA Alkylation Efficiency Through Introduction of Stabilizing Electrostatic Interactions", Bioorg. & Med. Chem. 3 (6): 611–621 Jun. (1995).
Mohamadi, et al., "Total Synthesis and Biological Properties of Novel Antineoplastic (Chloromethyl) furamoindolines: An Asymmetric Hydroboration Mediated Synthesis of the Alkylation Subunits", J. Med. Chem. 37: 232–239 (1994).
Boger, et al., "1,2,9,9a–Tetrahydrocyclopropa[c]benz[e]indol–4–one (CBI) Analogs of CC–1065 and the Duocarmycins: Synthesis and Evaluation", Bioorg. & Med. Chem. 3 (11): 1429–1453 Nov. (1995).
Warpehoski, et al., "Bis–Des–Hydroxy, Bis–Des–Methoxy CC–1065, Synthesis, DNA Binding, and Biological Activity", Tetrahedron Letters 29 (2): 131–134 (1988).

* cited by examiner

Primary Examiner—Laura L. Stockton
(74) Attorney, Agent, or Firm—Donald G. Lewis

(57) ABSTRACT

Analogs of the antitumor antibiotics CC-1065 and the duocarmycins incorporate the 1,2,9,9a-tetrahydrocyclopropa[c]benz[e]indol-4-one (CBI) alkylation subunit. The CBI-based analogs have potent cytotoxic activity and are useful as efficacious antitumor compounds. A direct relationship between functional stability and in vitro cytotoxic potency is disclosed. The CBI-based analogs are easily synthesized and are 4× more stable and 4× more potent than the corresponding analogs containing the authentic CPI alkylation subunit of CC-1065 and comparable in potency to agents containing the authentic alkylation subunit of duocarmycin SA. Similarly, the CBI-based agents alkylate DNA with an unaltered sequence selectivity at an enhanced rate and with a greater efficiency than the corresponding CPI analog and were comparable to the corresponding analog incorporating the duocarmycin SA alkylation subunit. Systematic and extensive modifications and simplifications in the DNA binding subunits attached to CBI are also described.

7 Claims, 34 Drawing Sheets

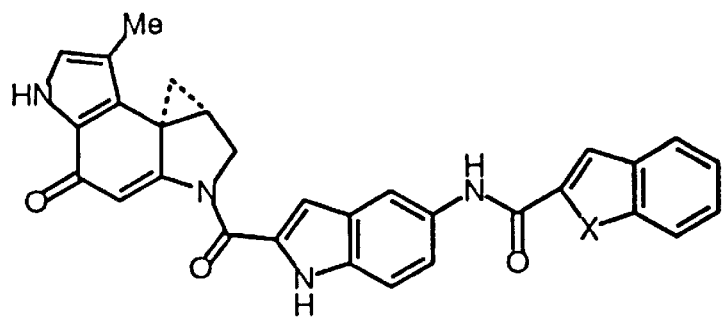
4   X = NH   U-71,184
5   X = O    U-73,975   adozelesin
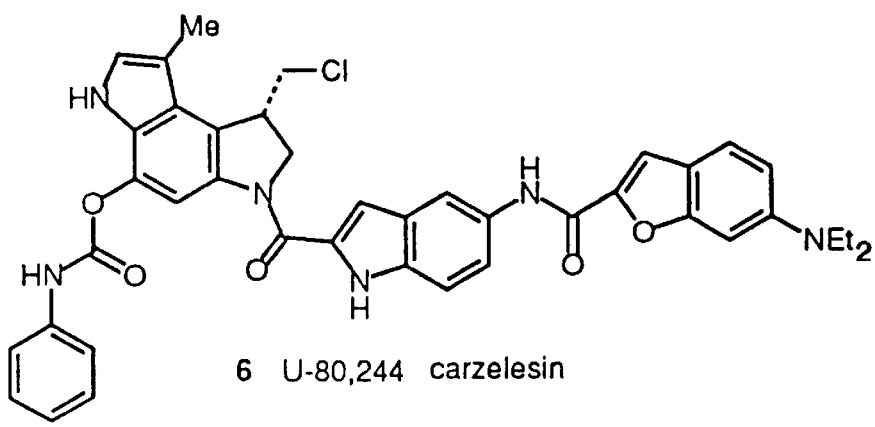
6   U-80,244   carzelesin
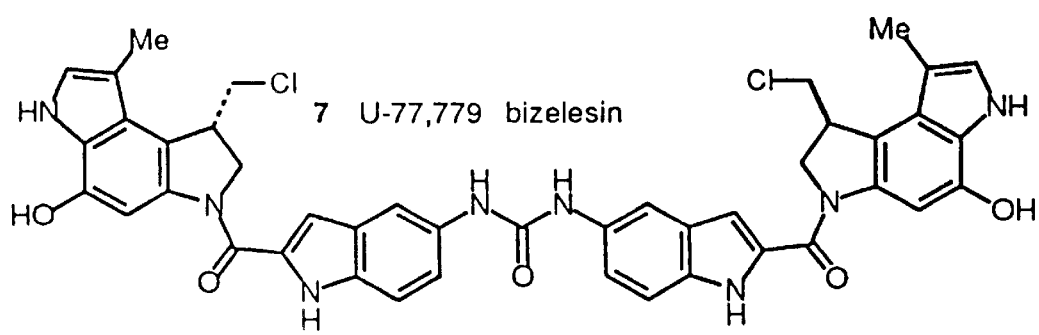
7   U-77,779   bizelesin
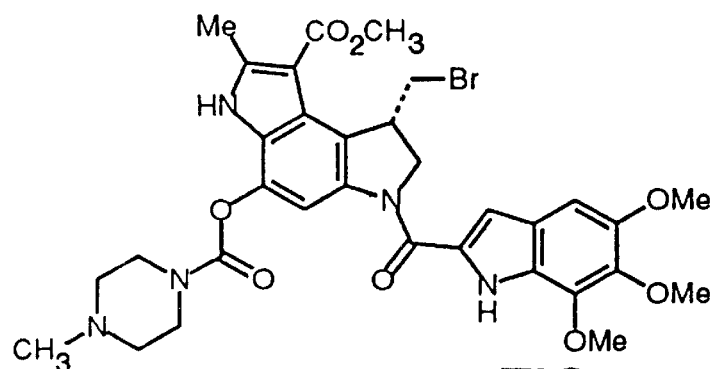
8   KW-2189
FIG.2

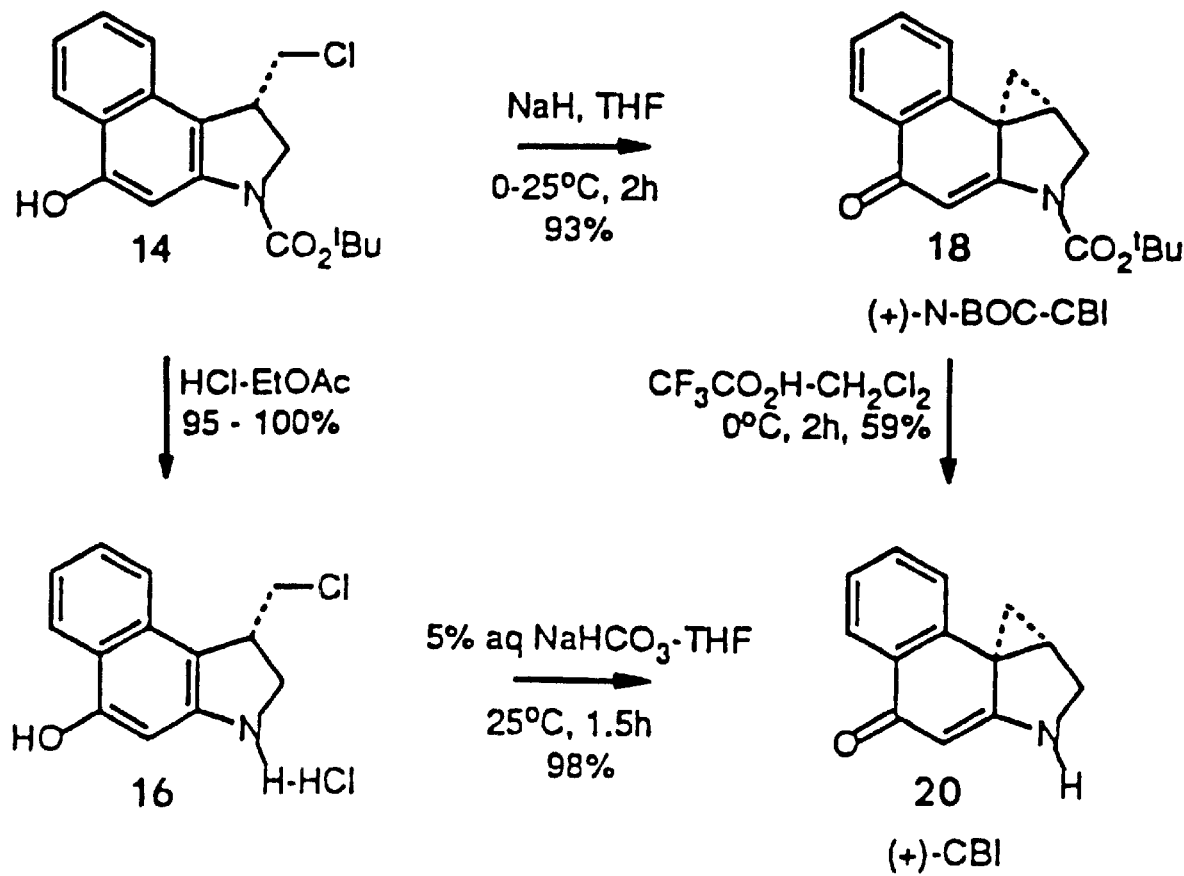
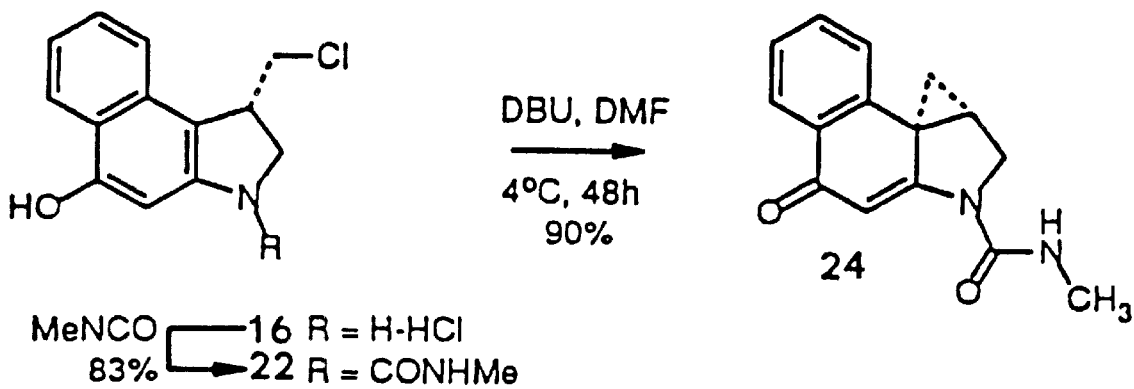
FIG.5A

| Agent | Configuration | IC$_{50}$(L1210, nM) |
|---|---|---|
| 9, (+)-N-BOC-CBI | natural | 80 |
| 9, (−)-N-BOC-CBI | unnatural | 1000 |
| 11, (+)-N-BOC-CPI | natural | 330 |
| 17, (+)-CBI | natural | |
| 17, (−)-CBI | unnatural | |
| (+)-15 | natural | 80 |
| (−)-15 | unnatural | 1000 |
| (+)-21 | natural | 200 |
| (+)-22 | natural | 140 |
| (+)-23 | natural | 110 |
| (+)-24 | natural | 25 |
| (−)-21 | unnatural | |
| (−)-22 | unnatural | |
| (−)-23 | unnatural | |
| (−)-24 | unnatural | |
| 18 | natural | 200 |
| 18 | unnatural | |
| 19 | natural | 140 |
| 19 | unnatural | |
| 20 | natural | 110 |
| 20 | unnatural | |

FIG.7

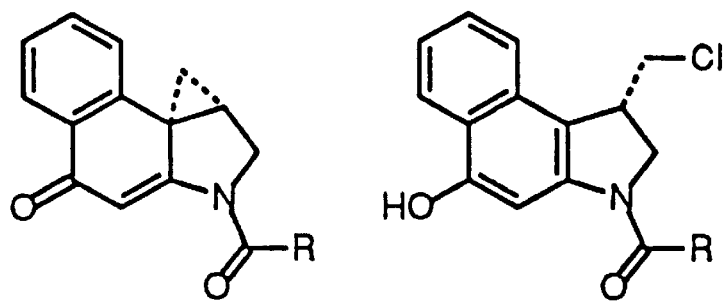
25 - 29    30 - 34
only natural enantiomers depicted
R =
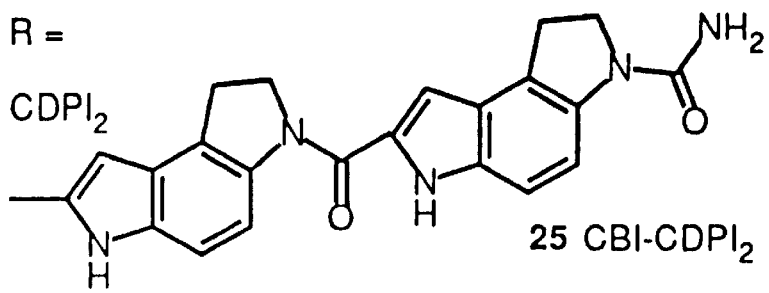
25 CBI-CDPI$_2$
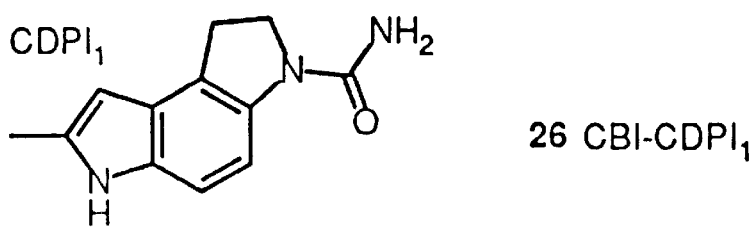
26 CBI-CDPI$_1$
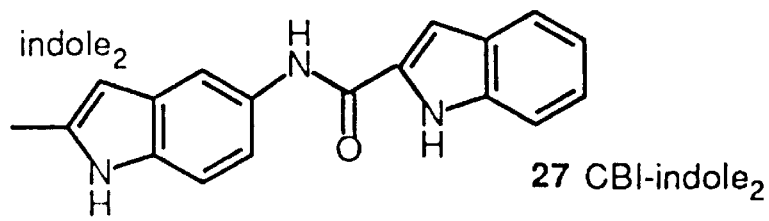
27 CBI-indole$_2$
28 CBI-indole$_1$
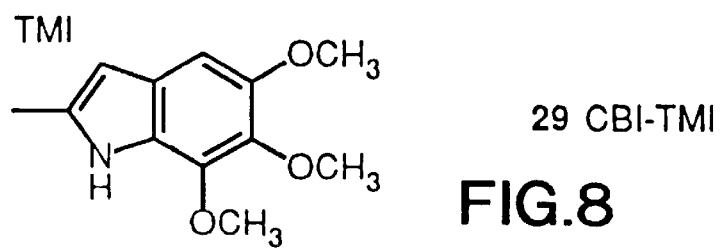
29 CBI-TMI
FIG.8

| Agent | Configuration | IC$_{50}$(L1210, pM) |
|---|---|---|
| 1, (+)-CC-1065 | natural | 20 |
| 1, ent-(−)-CC-1065 | unnatural | 20 |
| 2, (+)-duocarmycin SA | natural | 10 |
| 2, ent-(−)-duocarmycin SA | unnatural | 100 |
| 3, (+)-duocarmycin A | natural | 500 |
| 3, ent-(−)-duocarmycin A | unnatural | ≥22000 |
| 25, (+)-CBI-CDPI$_2$ | natural | 5 |
| 25, (−)-CBI-CDPI$_2$ | unnatural | 20 |
| (+)-CPI-CDPI$_2$ | natural | 20 |
| (−)-CPI-CDPI$_2$ | unnatural | 20 |
| 26, (+)-CBI-CDPI$_1$ | natural | 5 |
| 26, (−)-CBI-CDPI$_1$ | unnatural | 380 |
| (+)-CPI-CDPI$_1$ | natural | 40 |
| (−)-CPI-CDPI$_1$ | unnatural | 6300 |
| 27, (+)-CBI-indole$_2$ | natural | 10 |
| 27, (−)-CBI-indole$_2$ | unnatural | ? |
| 4, (+)-CPI-indole$_2$ | natural | 40 |
| 4, (−)-CPI-indole$_2$ | unnatural | 1000[a] |
| 28, (+)-CBI-indole$_1$ | natural | 5000 |
| 28, (−)-CBI-indole$_1$ | unnatural | 90[a] |
| 29, (+)-CBI-TMI | natural | 30 |
| 29, (−)-CBI-TMI | unnatural | 2000 |

FIG.9

| Agent | A | B | Configuration | IC$_{50}$ (L1210, pM) |
|---|---|---|---|---|
| (+)-CPI-indole$_2$ | | | natural | 40 |
| (−)-CPI-indole$_2$ | | | unnatural | 1000× Upjohn Value |
| (+)-27 | NH | NH | natural | 10$^a$ |
| (+)-57 | NH | O | natural | 10$^a$ |
| (+)-58 | NH | S | natural | 5 |
| (+)-59 | O | NH | natural | 5$^a$ |
| (+)-60 | O | O | natural | 15$^a$ |
| (+)-61 | O | S | natural | 7 |
| (−)-27 | NH | NH | unnatural | ? 300 Upjohn Value |
| (−)-57 | NH | O | unnatural | 30,000 |
| (−)-58 | NH | S | unnatural | 15,000$^b$ |
| (−)-59 | O | NH | unnatural | NT$^c$ |
| (−)-60 | O | O | unnatural | 1300 |
| (−)-61 | O | S | unnatural | 1200$^b$ |

$^a$The corresponding CPI analogs of 27, 57, 59, and 60 exhibited IC$_{50}$ values of 40, 40, 30, and 30 pM, respectively. $^b$Tested as the seco derivative 53 or 56. $^c$Not tested.

FIG. 11

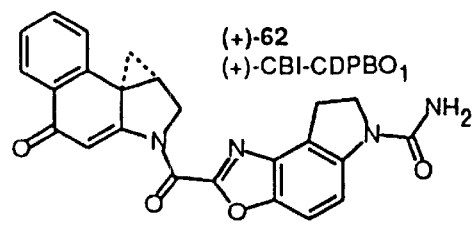
(+)-62
(+)-CBI-CDPBO₁
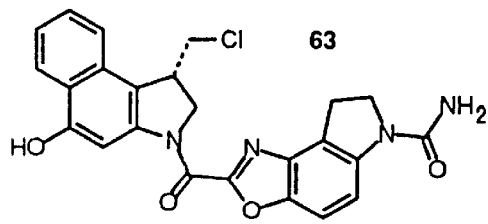
63
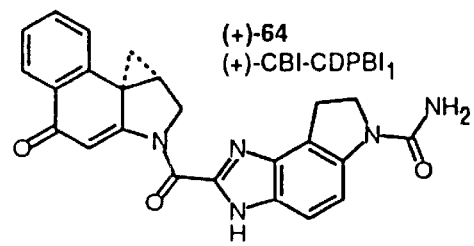
(+)-64
(+)-CBI-CDPBI₁
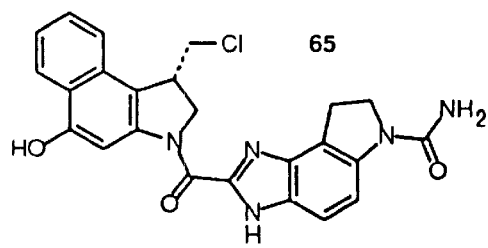
65
only natural enantiomers are depicted
PDE-i, CDPI
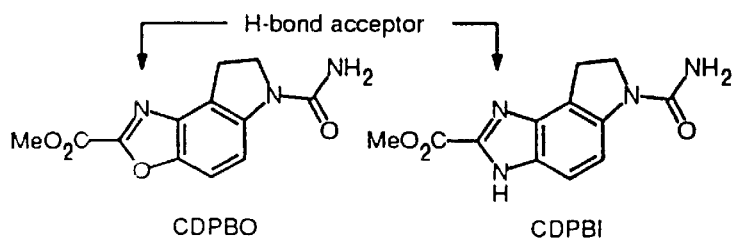
CDPBO          CDPBI
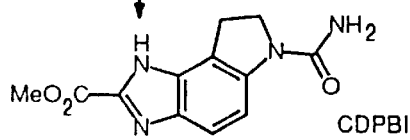
CDPBI
FIG. 12

| Agent | Configuration | IC$_{50}$ (L1210, pM) |
|---|---|---|
| 26, (+)-CBI-CDPI$_1$ | natural | 5 |
| 26, (−)-CBI-CDPI$_1$ | unnatural | 380 |
| 62, (+)-CBI-CDPBO$_1$ | natural | 200 |
| 62, (−)-CBI-CDPBO$_1$ | unnatural | 17000 |
| 64, (+)-CBI-CDPBI$_1$ | natural | 200 |
| 64, (−)-CBI-CDPBI$_1$ | unnatural | 2000 |
| 63, | natural | 200 |
| 63, | unnatural | 17000 |
| 65, | natural | 200 |
| 65, | unnatural | 2000 |
| 1, (+)-CC-1065 | natural | 20 |
| 1, (−)-CC-1065 | unnatural | 20 |
| 2, (+)-duocarmycin SA | natural | 10 |
| 2, (−)-duocarmycin SA | unnatural | 100 |

FIG. 13

33 R = H
66 R = 5-NMe$_3^+$
67 R = 6-NMe$_3^+$
68 R = 7-NMe$_3^+$

| Agent | IC$_{50}$ (L1210, nM) | Rel DNA Alkylation[a] |
|---|---|---|
| 1, (+)-CC-1065 | 0.02 | 1 |
| 2, (+)-duocarmycin SA | 0.01 | 1 |
| (+)-28, (+)-CBI-indole$_1$ | 5 | 0.01 |
| (+)-33 | 5 | 0.01 |
| (+)-66 | 10 | 1 |
| (+)-67 | 10 | 1 |
| (+)-68 | 10 | 1 |

[a]Relative efficiency for alkylation of w794 DNA (4 °C, 24 h)

FIG. 15

| Agent | IC$_{50}$ (L1210, nM) | rel DNA alkylation[a] |
|---|---|---|
| 9, (+)-N-BOC-CBI | 80 | 0.00001 |
| 72 | 100 | 0.00001 |
| 73 | 0.8 | 0.01 |
| 78 | 0.005 | 1 |
| 79 | 0.005 | 1 |
| 25, (+)-CBI-CDPI$_2$ | 0.005 | 1 |

[a]Relative efficiency of alkylation of w794 DNA; 37 °C, 24 h, reference 31.

FIG.18

| R | k (s⁻¹, pH 3) | $t_{1/2}$ | IC$_{50}$ (L1210) | sigma |
|---|---|---|---|---|
| 21 CONHMe | $5.4 \times 10^{-6}$ | 36 h | 200 nM | 0.36 |
| 22 CO$_2$Me | $3.4 \times 10^{-6}$ | 57 h | 140 nM | 0.45 |
| 23 COEt | $2.0 \times 10^{-6}$ | 96 h | 110 nM | 0.48 |
| 24 SO$_2$Et | $0.5 \times 10^{-6}$ | 383 h | 24 nM | 0.72 |

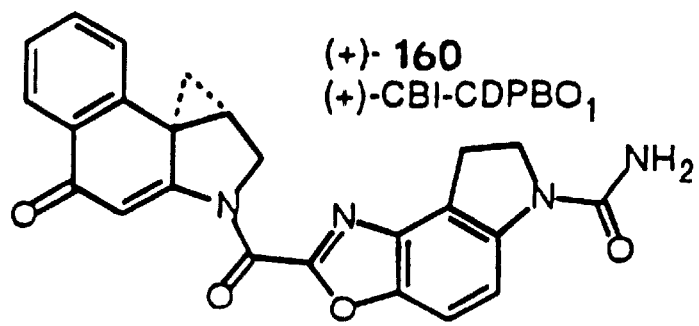
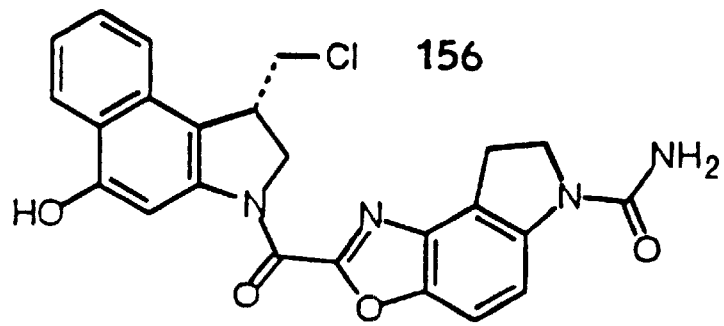
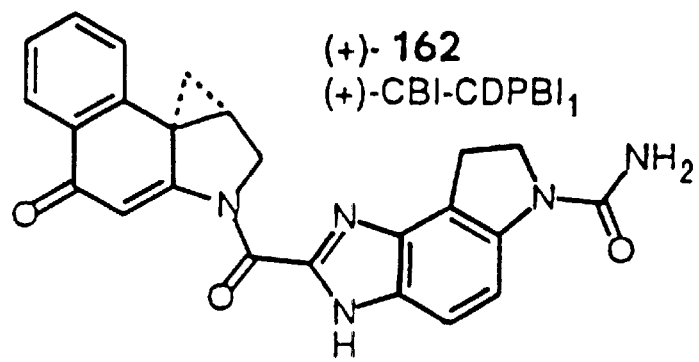
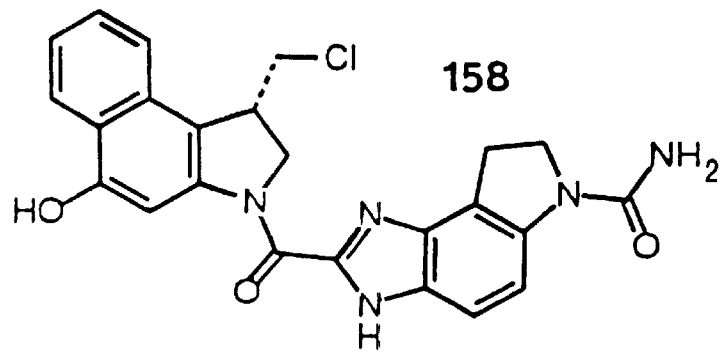
only natural enantiomers are depicted
FIG.28A

CBI ANALOGS OF CC-1065 AND THE DUOCARMYCINS

This application is a 371 of PCT/US96/16481 filed Oct. 3, 1996 which claims the benefit of U.S. Provisional No. 60/004,752 filed Oct. 3, 1995.

This invention was made with government support under Contract No. CA 41986 and CA 55276 by the National Institutes of Health. The government has certain rights in the invention.

FIELD OF INVENTION

The invention relates to antitumor antibiotics. More particularly, the invention relates to analogs of CC-1065 and the duocarmycins having antitumor antibiotic activity.

BACKGROUND (+)-CC-1065 (1) and the duocarmycins 2–3 represent the initial members of a class of exceptionally potent antitumor antibiotics. Members of this class of antitumor antibiotic derive their biological effects through the reversible, stereoelectronically-controlled sequence selective alkylation of duplex DNA. (H. Sugiyama, et al., *Tetrahedron Lett.* 1990, 31, 7197; C. H. Lin, et al., *J. Am. Chem. Soc.* 1992, 114, 10658; H. Sugiyama, et al., *Tetrahedron Lett.* 1993, 34, 2179; K. Yamamoto, et al., *Biochemistry* 1993, 32, 1059; A. Asai, et al., *J. Am. Chem. Soc.* 1994, 116, 4171; and D. L. Boger, et al., *Tetrahedron* 1991, 47, 2661.) (+)-CC-1065 (1) was first disclosed in 1981 by L. J. Hanka, et al.. (*J. Am. Chem. Soc.* 1981, 103, 7629.) The duocarmycins 2–3 were first disclosed in 1988 and 1990. (Takahashi, et al.. *J. Antibiot.* 1988, 41, 1915; T. Yasuzawa, et al., *Chem. Pharm. Bull.* 1988, 36, 3728; M. Ichimura, et al., *J. Antibiot.* 1988, 41, 1285; M. Ichimura, et al., *J. Antibiot.* 1990, 43, 1037; M. H. Ichimura, et al., *J. Antibiot.* 1991, 44, 1045; K. Ohba, et al., *J. Antibiot.* 1988, 41, 1515; and S. Ishii, *J. Antibiot.* 1989, 42, 1713.)

Subsequent to their disclosure, extensive efforts have been devoted to establish their duplex DNA alkylation selectivity and its structural origin. (D. L. Boger, *Acc. Chem. Res.* 1995, 28, 20; D. L. Boger, *Proc. Nal. Sci. U.S.A.* in press; D. L. Boger, *Chemtracts: Org. Chem.* 1991, 4, 329; D. L. Boger, In *Proceed R. A. Welch Found. Conf. on Chem. Res., XXXV. Chem. at the Frontiers of Medicine* 1991, 35, 137; D. L. Boger, In *Advances in Heterocyclic Natural Products Synthesis*, Vol. 2, Pearson, W. H. Ed.; JAI Press: Greenwich, Conn., 1992, 1–188; D. L. Boger, *Pure Appl. Chem.* 1993, 65, 1123; D. L. Boger, *Pure Appl. Chem.* 1994, 66, 837; R. S. Coleman, In *Studies in Nat. Prod. Chem.*, Vol 3, Rahman, A.-u.-, Ed.; Elsevier: Amsterdam, 1989, 301; and D. L. Boger, In *Heterocycles in Bioorganic Chemistry*; J. Bergman, H. C. van der Plas, and M. Simonyl, Eds; Royal Society of Chemistry: Cambridge, 1991, 103.) Progress has also been made with respect to characterizing the link between DNA alkylation and the ensuing biological properties. (D. L. Boger, et al., *Bioorg. Med. Chem. Lett.* 1994, 4, 631.) Extensive efforts have also been devoted to define the fundamental principles underlying the relationships between structure, chemical reactivity, and biological properties. (W. Wierenga, et al., *Adv. Enzyme Regul.* 1986, 25, 141; M. A. Warpehoski, et al., *J. Med. Chem.* 1988, 31, 590; D. L. Boger, et al., *J. Am. Chem. Soc.* 1993, 115, 9025; D. L. Boger, et al., *J. Am. Chem. Soc.* 1992, 114, 10056; H. Muratake, et al., *Tetrahedron Lett.* 1994, 35, 2573; Y. Fukuda, et al., *Tetrahedron* 1994, 50, 2793; Y. Fukuda, et al., *Tetrahedron* 1994, 50, 2809; Y. Fukuda, et al., *Bioorg. Med. Chem. Lett.* 1992, 2, 755; Y. Fukuda, et al., *Tetrahedron Lett.* 1990, 31, 6699; W. Wierenga, *J. Am. Chem. Soc.* 1981, 103, 5621; P. Magnus, et al., *J. Am. Chem. Soc.* 1987, 109, 2706; G. A. Kraus, et al., *J. Org. Chem.* 1985, 50, 283; D. L. Boger, et al., *J. Am. Chem. Soc.* 1988, 110, 1321, 4796; R. E. Bolton, et al., *J. Chem. Soc., Perkin Trans.* 1 1988, 2491; R. J. Sundberg, et al., *J. Org. Chem.* 1988, 53, 5097; R. J. Sundberg, et al., *J. Org. Chem.* 1991, 56, 3048; V. P. Martin, *Helv. Chim. Acta* 1989, 72, 1554; M. Toyota, et al., *J. Chem. Soc., Perkin Trans.* 1 1992, 547; and L. F. Tietze, et al., *J. Org. Chem.* 1994, 59, 192.) The relationships between structure, chemical reactivity, and biological properties of CI-based analogs have also been characterized. (D. L. Boger, et al., *Proc. Natl. Acad. Sci. U.S.A.* 1991, 88, 1431; D. L. Boger, et al., *J. Am. Chem. Soc.* 1991, 113, 3980; D. L. Boger, et al., *J. Org. Chem.* 1989, 54, 1238; D. L. Boger, et al., *J. Am. Chem. Soc.* 1990, 112, 5230; K. J. Drost, et al., *J. Org. Chem.* 1989, 54, 5985; J. H. Tidwell, et al., *J. Org. Chem.* 1992, 57, 6380; J. Sundberg, et al., *Tetrahedron Lett.* 1986, 27, 2687; Y. Wang, et al., *Heterocycles* 1993, 36, 1399; Y. Wang, et al., *J. Med. Chem.* 1993, 36, 4172; L. F. Tietze, et al., *Chem. Ber.* 1993, 126, 2733; and T. Sakamoto, et al., *J. Chem. Soc., Perkin Trans.* 1 1993, 1941.) The relationships between structure, chemical reactivity, and biological properties of $C_2BI$-based analogs have also been characterized. (D. L. Boger, et al., *J. Am. Chem. Soc.* 1992, 114, 9318; and D. L. Boger, et al., *Bioorg. Med. Chem.* 1993, 1, 27.) The relationships between structure, chemical reactivity, and biological properties of CBQ-based analogs have also been characterized. (D. L. Boger, et al., *J. Am. Chem. Soc.* 1994, 116, 6461; and D. L. Boger, et al., *J. Am. Chem. Soc.* 1994, 116, 11335.) F. Mohamadi et al. have characterized the relationships between structure, chemical reactivity, and biological properties of CFI-based analogs (*J. Med Chem.* 1994, 37, 232.) A p-quinonemethide analog was characterized by D. L. Boger, et al.. (*J. Org. Chem.* 1994, 59, 4943.)

Concurrent with the above structure/function studies, substantial efforts have been devoted to developing potential clinical candidates based on the natural product structures having enhanced in vivo efficacy. Compounds 4–8 are analogs of the natural product structures having enhanced in vivo efficacy with clinical potential. (D. L. Boger, et al., *J. Org. Chem.* 1984, 49, 2240; M. A. Warephoski, M. A. *Tetrahedron Lett.* 1986, 27, 4103; Li, L. H.; *Invest New Drugs* 1991, 9, 137; B. K. Bhuyan, et al., *Cancer Res.* 1992, 52, 5687; B. K. Bhuyan, et al., *Cancer Res.* 1993, 53, 1354; L. H. Li, et al., *Cancer Res.* 1992, 52, 4904; M. A. Mitchell, et al., *J. Am. Chem. Soc.* 1991, 113, 8994. Lee, C.-S.; Gibson, N. W. *Cancer Res.* 1991, 51, 6586. Lee, C.-S.; Gibson, N. W. *Biochemistry* 1993, 32, 9108; Wierenga, W. *Drugs Fut.* 1991, 16, 741; K. Gomi, et al., *Jpn. J. Cancer Res.* 1992, 83, 113. Okamoto, A.; Okabe, M.; Gomi, K. *Jpn. J. Cancer Res.* 1993, 84, 93; E. Kobayashi, et al., *Cancer Res.* 1994, 54, 2404; and H. Ogasawara, *Jpn. J. Cancer Res.* 1994, 85, 418. ) A Phase I clinical trial one one drug candidate in this class is described by G. F. Fleming, et al., (*J. Natl. Cancer Inst.* 1994, 86, 368.) Efforts have also focused on the development of analogs having decreased delayed toxicity as compared to the natural form of (+)-CC-1065. (J. P. McGovren, et al., *Cancer Res.* 1993, 53, 5690.) Importantly, this unusual property has not been observed with ent-(−)-CC-1065, although it is equally cytotoxic, and is not observed with the naturally-derived duocarmycins as well as simplified analogs of the natural products.

The first preparation and examination of agents containing the 1,2,9,9a-tetrahydrocyclopropa[c]benz[e]indol-4-one (CBI) alkylation subunit were described in connection with efforts to evaluate CC-1065 and duocarmycin analogs bearing deep-seated structural alterations in the alkylation subunit. (D. L. Boger, et al., *J. Am. Chem. Soc.* 1989, 111, 6461; and D. L. Boger, et al., *J. Org. Chem.* 1990, 55, 5823.) These agents were employed as tools to identify the structural features of compounds 1–3 associated with their sequence selective alkylation of duplex DNA and to define the fundamental relationships between structure, chemical or functional reactivity and biological properties.

Prior to the present invention, it had been assumed that the unique alkylating activity of the naturally occurring CPI subunit of CC-1065 would be degraded if this portion of the molecule were structurally altered. (L. H. Hurley, et al., *Science* 1984, 226, 843; V. L. Reynolds, et al., *Biochemistry* 1985, 24, 6228. L. H. Hurley, et al., *Biochemistry* 1988, 27, 3886; L. H. Hurley, et al., *J. Am. Chem. Soc.* 1990, 112, 4633; M. A. Warpehoski, et al., *J. Biochemistry* 1992, 31, 2502; D. L. Boger, et al., *Bioorg. Med. Chem.* 1994, 2, 115; D. L. Boger, et al., *J. Am. Chem. Soc.* 1990, 112, 4623; M. A. Warpehoski, et al., *In Advances in DNA Sequence Specific Agents;* Hurley, L. H., Ed.; JAI Press: Greenwich, Conn., 1992, Vol 1, 217; M. A. Warpehoski, *Drugs Fut.* 1991, 16, 131; M. A. Warpehoski, et al., in *Molecular Basis of Specificity in Nucleic Acid-Drug Interactions;* B. Pullman and J. Jortner, Eds.; Kluwer: Netherlands; 1990, 531; M. A. Warpehoski, et al., *Chem. Res. Toxicol.* 1988, 1, 315; Hurley, L. H.;. In *Molecular Aspects of Anticancer Drug-DNA Interactions;* Neidle, S., Waring, M., Eds.; CRC Press: Ann Arbor, Mich. 1993, Vol 1, 89; and L. H. Hurley, et al., *Acc. Chem. Res.* 1986, 19, 230.) The above assumption is disclosed herein to be inaccurate. Furthermore, the natural enantiomers of the CBI-based analogs of (+)-CC-1065, have been shown to be approximately four times more stable chemically and approximately four times more potent biologically as compared to the corresponding agents incorporating the natural CPI alkylation subunit of CC-1065. (D. L. Boger, et al., *Tetrahedron Lett.* 1990, 31, 793; D. L. Boger, et al., *J. Org. Chem.* 1992, 57, 2873; and D. L. Boger, et al., *J. Org. Chem.* 1995, 60, 0000.) The CBI analogs are also considerably more synthetically accessible as compared to the naturally occuring CPI compounds. (+)-CBI-indole$_2$ (27) exhibits cytotoxic potency comparable to that of the (+)-CC-1065 and greater (4×) than that of the potential clinical candidate (+)-CPI-indole$_2$ (4, U71,184) introduced by Upjohn. (+)-CBI-indole$_2$ (27) also exhibits potent and efficacious in vivo antitumor activity. (D. L. Boger, et al., *Bioorg. Med. Chem. Lett.* 1991, 1, 115.) (+)-CBI-indole$_2$ (27) was the first efficacious antitumor activity by a CC-1065 analog possessing a structurally altered and simplified DNA alkylation subunit. Moreover, the agent further lacked the delayed fatal toxicity characteristic of (+)-CC-1065.

The natural enantiomers of the CBI-based analogs have been shown to alkylate DNA with an unaltered sequence selectivity as compared to the corresponding CPI analog. (D. L. Boger, et al., *J. Am. Chem. Soc.* 1994, 116, 7996; and P. A. Aristoff, et al., *J. Med Chem.* 1993, 36, 1956.) Furthermore, the DNA alkylation of CBI-based analogs occurs at an enhanced rate as compared to the corresponding CPI analogs (D. L. Boger, et al., *J. Am. Chem. Soc.* 1991, 113, 2779) and with a greater efficiency than the corresponding CPI analog. (D. L. Boger, et al., *J. Am. Chem. Soc.* 1992, 114, 5487)

Refined models of the DNA alkylation reactions of the duocarmycins have been developed which accomodate the reversed and offset AT-rich adenine N3 DNA alkylation selectivity of the enantiomeric agents and their structural analogs. (D. L. Boger, et al.,i *J. Org. Chem.* 1990, 55, 4499; D. L. Boger, et al., *J. Am. Chem. Soc.* 1990, 112, 8961; D. L. Boger, et al., *J. Am. Chem. Soc.* 1991, 113, 6645; D. L. Boger, et al., *J. Am. Chem. Soc.* 1993, 115, 9872; D. L. Boger, et al., *Bioorg. Med. Chem. Lett.* 1992, 2, 759; and D. L. Boger, et al., *J. Am. Chem. Soc.* 1994, 116, 1635.) A similar refined model of the DNA alkylation reactions of CC-1065 have been developed which also accomodate the reversed and offset AT-rich adenine N3 DNA alkylation selectivity of the enantiomeric agents and their structural analogs. (D. L. Boger, et al., *Bioorg. Med. Chem.* 1994, 2, 115; and D. L. Boger, et al., *J. Am. Chem. Soc.* 1990, 112, 4623.) These models teach that the diastereomeric adducts derived from the unnatural enantiomers suffer a significant destabilizing steric interaction between the CPI C7 center ($CH_3$) or the CBI C8 center with the base adjacent to the alkylated adenine which is not present with the natural enantiomer adducts. Moreover, the distinguishing features of the natural and unnatural enantiomers diminish or disappear as the inherent steric bulk surrounding this center is reduced or removed. Because of the unnatural enantiomer sensitivity to destabilizing steric interactions surrounding the CPI C7 or CBI C8 center, the unnatural enantiomers of the CBI-based analogs are particularly more effective than the corresponding CPI analog displaying an even more enhanced relative rate and efficiency of DNA alkylation.

SUMMARY

An extensive study of analogs of the potent antitumor antibiotics CC-1065 and the duocarmycins which incorporate the 1,2,9,9a-tetrahydrocyclopropa[c]benz[e]indol-4-one (CBI) alkylation subunit are detailed. In contrast to early speculation, deep-seated modifications in the CC-1065 and duocarmycin alkylation subunits are well tolerated and the CBI-based analogs proved to be potent cytotoxic agents and efficacious antitumor compounds. Full details of studies defining a direct relationship between functional stability and in vitro cytotoxic potency are described. As such, the readily accessible CBI-based analogs were found to be 4× more stable and 4× more potent than the corresponding analogs containing the authentic CPI alkylation subunit of CC-1065 and comparable in potency to agents containing the authentic alkylation subunit of duocarmycin SA. Similarly, the CBI-based agents alkylate DNA with an unaltered sequence selectivity at an enhanced rate and with a greater efficiency than the corresponding CPI analog and were comparable to the corresponding analog incorporating the duocarmycin SA alkylation subunit. Systematic and extensive modifications and simplifications in the DNA binding subunits attached to CBI were explored with the comparisons of both enantiomers of 1–3 with both enantiomers of 18–24, 25–29, 57–61, 62–65, 66–68, 72–73 and 78–79.

CPI and CBI Structures

Simple Derivatives of CBI. Role of the $N^2$ Substituent and Validation of a Direct Relationship Between Functional Stability and In Vitro Cytotoxic Potency. Substantial quantities of optically active natural-(1S)- and ent-(1R)-15 were prepared through use of our original synthesis of CBI and its precursors, as referenced above with two recent modifications. (D. L. Boger, et al., *J. Org. Chem.* 1992, 57, 2873; and D. L. Boger, et al., *J. Org. Chem.* 1995, 60, 0000.) The most efficient approach now proceeds in 9 steps and in 38% overall yield from commercially available 1,3- dihydroxynapthalene based on a key 5-exo-trig aryl radical-alkene cyclization for the direct preparation of N-BOC-5-benzyloxy-1-hydroxymethyl-1,2-dihydro-3H-benz[e]indole. Moreover, the initial resolution we described based on the chromatographic separation of the diastereomeric (R)-O-acetyl madelate esters of the primary alcohol precursor to 15 which has been adopted by others has been since improved in our efforts. The more advanced synthetic intermediate 15, and in fact the penultimate intermediate to the CBI-based analogs, may be directly and more efficiently resolved ($\alpha=1.28$) on an analytical or preparative Daicel Chiralcel OD column without recourse to diastereomeric derivatization. For our purposes, 20 mg of 15 could be separated in a single injection on a semipreparative 10 $\mu$m, 2×25 cm OD HPLC column (5% i-PrOH-hexane, 8 mL/min) with a 90–100% recovery of the total sample. Conversion of natural (1S)- and ent-(1R)-15 to (+)- and ent-(−)-N-BOC-CBI (9), and (+)- and ent-(−)-CBI (17) have been detailed in our initial studies, and provided our comparison standards for the studies detailed below (FIG. 1).

Initial studies conducted with simple derivatives of the (+)-CC-1065 alkylation subunit (CPI) led to the proposal that there exists a direct relationship between an agent's reactivity and in vitro cytotoxic potency (L1210, $IC_{50}$) and established the expectation that the biological potency may be enhanced as their electrophilic reactivity is increased. In our complementary series of studies conducted with agents containing deep-seated modifications in the alkylation subunit including 9–14, the reverse relationship has been observed and the agents possessing the greatest chemical solvolysis stability exhibited the most potent in vitro cytotoxic activity. Moreover, a direct relationship between solvolytic stability and biological potency has been observed and proved to be general with both simple and advanced analogs of the natural products.

As a consequence of these studies, we became interested in the inherent role of the CC-1065 and duocarmycin $N^2$ substituent. Consequently, the simple derivatives 21–24 of (+)-CBI were prepared for examination and, by virtue of their structural similarities, were expected to more accurately reflect a potential relationship between functional reactivity and biological potency than the preceding studies. Treatment of crude, freshly prepared 16 with methyl isocyanate (2 equiv, 3 equiv $NaHCO_3$, THF, 0–25° C., 1 h, 83%) provided 18 and attempts to conduct this reaction in more polar solvents including DMF or in the presence of a stronger base (i.e. $Et_3N$) which promotes competitive closure of 16 to CBI (17) led to lower conversions. Spirocyclization of 18 to 21 was effected by treatment with DBU (2 equiv, DMF, 4° C., 48 h, 90%) and the use of shorter reaction periods (24 h, 55%) or less polar solvents (THF, 18 h, 35%) provided lower conversions. Treatment of the freshly generated crude indoline hydrochloride salt 16 with $ClCO_2CH_3$ (2 equiv, 3 equiv $NaHCO_3$, THF, 0–25° C., 1.5 h) provided 19 (100%) in quantitative conversion. Spirocyclization of 19 to provide 22 was effected by treatment with DBU (2 equiv, THF, 0° C., 48 h and 25° C., 10 h, 93%) and the rate of ring closure of 19 to 22 only became significant at 25° C. under these conditions. Even treatment of 19 with $K_2CO_3$ (1.5 equiv, THF, 25° C., 5 d, 51%) provided 22 albeit with this latter reaction requiring a long reaction period. Similarly, treatment of crude 16 with $ClCOCH_2CH_3$ (2 equiv, 3 equiv $NaHCO_3$, THF, 0–25° C., 5 h or 0° C., 1H) cleanly provided 20 (94–98%). Spirocyclization of 20 to cleanly provide 23 was effected by simply dissolving 20 in a 1:1 mixture of 5% aqueous $NaHCO_3$-THF (25° C., 5–10 h, 97%) and stirring the resulting two-phase reaction mixture at room temperature. Given the ease of hydrolysis of N-acyl-CBI derivatives upon exposure to aqueous base, it is of special note that this set of reaction conditions worked so well for 23. Lower conversions to 23 were observed upon treatment of 20 with DBU (2 equiv, THF, 0–25° C., 18 h) and, although this was not examined in detail, can be attributed to a slow cyclization under the reaction conditions resulting in significant amounts of recovered, unreacted 20. Surprisingly, the most challenging of the derivatives to prepare was 24. Attempts to couple freshly generated 16 with $ClSO_2CH_2CH_3$ under a wide range of reaction conditions deliberately generating or avoiding sulfene formation suffered from competitive or preferential O-sulfonylation or competitive closure to 17. Although this approach could be used to generate 24, the most productive preparation was accomplished simply by reaction of the sodium salt of CBI (17, 2.5 equiv NaH, THF, 0° C., 10 min) with $ClSO_2CH_2CH_3$ (7 equiv, 3 equiv $Et_3N$, 25° C., 3 h, 45%) to provide 24 directly.

The acid-catalyzed solvolysis of 21–24 conducted at pH 3 ($CH_3OH$—$H_2O$) were followed spectrophotometrically by UV with the disappearance of the characteristic long-wavelength absorption band of the CBI chromophore and with the appearance of a short-wavelength absorption band attributable to the seco-N-BOC-CBI derivative, FIGS. 19A–19B. The results of these studies along with the cytotoxic activities of 21–24 are summarized in FIGS. 20A–20D. The cytotoxic activity of the full set of agents examined and the comparisons with the related CPI-based agents are summarized in FIG. 7.

The comparisons of 21–24 revealed a direct, linear relationship between the cytotoxic potency (L1210, log $1/IC_{50}$) and the solvolytic stability (−log $k_{solv}$, pH 3) of the agents (FIGS. 20A–20D). Thus, similar to the trend observed with 9–14, the solvolytically more stable derivatives of CBI proved to be the most potent. Similarly, a linear relationship was found between the electron-withdrawing properties of the $N^2$ substituents (Hammett $\sigma_p$ constant) and the solvolysis reactivity (−log $k_{solv}$, pH 3) of the agents with the strongest electron-withdrawing substituents providing the most stable agents (FIGS. 20A–20D). This latter relationship reflects the influence of the $N^2$ substituent on the ease of C4 carbonyl protonation required for catalysis of solvolysis and cyclopropyl ring cleavage with the stronger electron-withdrawing $N^2$ substituents exhibiting slower solvolysis rates. Less obvious but more fundamental, the observations were found to follow a predictable linear relationship between the cytotoxic potency (L1210, log $1/IC_{50}$) and the electron-withdrawing properties of the $N^2$ substituent (Hammett $\sigma_p$) with the strongest electron-withdrawing substituents providing the biologically most potent agents (FIGS. 20A–20D).

These fundamental correlations between the electron-withdrawing properties of the $N^2$ substituent, the functional reactivity of the agents, and their biological potency should prove useful in the predictable design of new analogs. In fact, it is this fundamental validation of the direct relationship between functional stability and biological potency that suggests that the CBI-based analogs, which are 4× more stable than the corresponding CPI-based analogs, offer rationally-based advantages that may be expected to be even further enhanced by the inherent selectivity that is intrinsic in the diminished reactivity. For agents in this class which possess sufficient reactivity to effectively alkylate duplex DNA, the chemically more stable agents may be expected to constitute the biologically more potent agents. Presumably, this may be attributed to the more effective delivery of the more stable agents to their intracellular target, and the solvolysis rates may be taken to represent a general measure of the relative functional reactivity. Notably, the consumption of the agent in route to its intracellular target need not be simply nonproductive solvolysis but competitive alkylation of nonproductive extra- and intracellular sites as well including the potential of nonproductive sites within duplex DNA. Since the chemically more stable agents provide thermodynamically less stable and more readily reversed addition products, the observations may also represent a more effective thermodynamic partitioning of the agents to their productive intracellular target or site(s).

Consistent with prior observations, the corresponding seco agents 15 and 18–20 which serve as the immediate synthetic precursors to 9 and 21–23 exhibited a cytotoxic potency indistinguishable from that of the corresponding agent incorporating the preformed cyclopropane ring. Since simple C4 phenol O-alkyl ($CH_3$, $CH_2Ph$) and O-acyl derivatives of 15 exhibit substantially diminished cytotoxic potency (10–100×), this equivalency of the seco precursors 15 and 18–20 with 9 and 21–23 most likely may be attributed to their facile closure to the biologically relevant and more potent cyclopropane containing agents. Notably, such observations have been instrumental in the successful development of prodrug strategies for the advanced analogs of the natural products including 6–8.

Although we have described an extensive account of the DNA alkylation properties of (+)- and ent-(−)-N-BOC-CBI (9) and their comparison with those of (+)- and ent-(−)-N-BOC-CPI (11) the properties of 21–24 and their relationship to the biological evaluations are worth summarizing. The agents 21–24 behaved in a manner comparable to 9. The natural and unnatural enantiomers of 21–24 were substantially less efficient (ca. $10^4$×), less selective (selectivity=5′-A A>5′-TA) with 40–45% of all adenines alkylated over a 10-fold agent concentration range, and exhibited an altered DNA alkylation profile than (+)- or ent-(−)-1-3. Moreover, the natural enantiomers of 21–24, like (+)- vs ent-(−)-9, proved to be approximately 5–10× more efficient than the unnatural enantiomers at alkylating DNA, but were found to exhibit the same selectivity and alkylate the same sites. This alkylation selectivity of 21–24, like that of 9, was identical to that of (+)- or ent-(−)-N-BOC-CPI. However, both the natural enantiomers (5×) and especially the unnatural enantiomers (10–100×) of the CBI-based agents were more effective at alkylating DNA than the corresponding CPI-based agent consistent with models that we have discussed in detail. Importantly, the less reactive CBI-based agents were found to alkylate DNA at a faster rate, with a greater efficiency, and with a slightly greater selectivity among the available sites than the corresponding CPI-based agent. This may be interpreted in terms of agents steric accessibility to the adenine N3 alkylation site where the C7 methyl group of the CPI alkylation subunit sterically decelerates the rate of DNA alkylation to the extent that the less reactive, but more accessible, CBI subunit alkylates DNA at a more rapid rate. Since the unnatural enantiomers are even more sensitive to destabilizing steric interactions at the CPI C7 or CBI C8 position, the unnatural enantiomers of the CBI-based agents are particularly more effective than the CPI-based agents.

Advanced Analogs of CC-1065 and the Duocarmycins: Simplification of the DNA Binding Subunits. The preparation and evaluation of both enantiomers of CBI-$CDPI_2$ (25), CBI-$CDPI_1$ (26), CBI-$indole_2$ (27), CBI-$indole_1$ (28), and CBI-TMI (29) and their corresponding seco precursors 30–34 have been disclosed in our early studies and their detailed comparisons with both enantiomers of CC-1065 or the duocarmycins described. More recently, 27, 28, and CBI-PDE-$I_2$ have been disclosed by Aristoff and co-workers. The comparative cytotoxic activity of these prior agents prepared in our studies is summarized in FIG. 9 along with that of the corresponding CPI-based analog.

In an extension of our investigations which first revealed efficacious antitumor activity for 27, we have expanded the studies to the preparation and evaluation of 57–61, a larger series based on 27. The DNA binding subunits of CC-1065 and the duocarmycins contribute in several ways to the properties of the natural products. They contribute significantly to the DNA binding affinity which serves both to increase the rate of DNA alkylation relative to 9 and to thermodynamically stabilize the inherently reversible DNA alkylation reaction. While the former has been suggested to be the origin of the differences in the cytotoxic potency of 1 and 11 by others based principally on the comparisons of (+)-N-BOC-CPI (11), (+)-CPI-$indole_1$, and (+)-CPI-$indole_2$, we have proposed that it is the latter that constitutes the biologically significant distinction. This thermodynamic versus kinetic distinction was first proposed before the reversibility of the DNA alkylation reaction was experimentally verified and was based in part on the observation that the cytotoxic potency of a class of agents would plateau. For example, (+)-CC-1065, (+)-CPI-PDE-$I_1$, and (+)-CPI-$CDPI_n$ (n=1–3) were found to be indistinguishable in our cytotoxic assays ($IC_{50}$=20 pM, L1210). Although the five agents exhibit large differences in their rates of DNA alkylation, all five form thermodynamically stable adducts under physiological conditions. We attribute the increase in cytotoxic potency of CPI-$CDPI_n$ (n=1–3) vs 11 to noncovalent binding stabilization of the reversible DNA adduct formation and that it is the simple event not extent of this stabilization that results in their essentially equivalent properties. This interpretation further suggests that CPI-indole, and CBI-$indole_1$ lack the sufficient stabilization for observation of full potency. Moreover, the interpretation is consistent with the observation that a maximum potency is achievable and that the level of this potency is directly related to the functional stability of the agents. Thus, the CBI-based agents examined to date exhibit a similar plateau of potency (5 pM, L1210) but at a level 4× more potent than that of the corresponding CPI-based agents (20 pM, L1210).

In addition, the DNA binding subunits of CC-1065 contribute to a strong AT-rich DNA binding selectivity which we have recently shown not only contributes to the alkylation selectivity of the agents but exerts an overriding dominate control. In early studies, we were able to demonstrate that the noncovalent binding affinity was derived nearly exclusively from stabilizing van der Waals contacts and hydrophobic binding. Not only did the studies suggest that CC-1065 is best represented as a selective alkylating agent superimposed on the trimer skeleton but removal of the peripheral methoxy and hydroxy substituents (PDE-I-CDPI) had no effect on its noncovalent AT-rich binding selectivity and little effect on its binding affinity. This dependence on hydrophobic binding stabilization results in preferential binding in the narrower, deeper AT-rich regions of the minor groove where the stabilizing van der Waals contacts are maximal ($\Delta G°$=9.5–11.5 kcal/mol). Moreover, such studies suggested seminal ways in which the DNA binding subunits could be simplified (removal of polar substituents) without altering the characteristics responsible for the essential DNA binding affinity or selectivity.

The DNA binding subunits of the agents may also have a significant impact on the physical properties and characteristics of the agents. Most apparent is the remarkable solubility properties of CC-1065 which is essentially insoluble in all solvents except DMSO or DMF including polar protic or aprotic solvents, water, or nonpolar solvents. A major impact that structural variations in the central and right hand subunits may have is in the solubility properties of the agent and hence its biodistribution and bioavailability.

Finally, we have speculated that the extent of the noncovalent binding stabilization of the inherently reversible DNA alkylation reaction may be responsible for the unusual, delayed toxicity of CC-1065. That is, the extensive noncovalent binding stabilization of 1 that renders its DNA alkylation reaction irreversible while that of simpler agents including 2–3 are slowly reversible under physiological conditions offers a potential explanation for the apparently confusing toxicity profile among the analogs detailed to date. The only agents that have exhibited the delayed toxicity that we are aware of are (+)-CC-1065 (1), (+)-CPI-CDPI$_2$, and (+)-CBI-PDE-I$_2$. Each provide irreversible adduct formation under physiological conditions, and the unnatural enantiomers of each, which form inherently less stable and more reversible adducts, do not exhibit the delayed toxicity. Although speculative, it does suggest that simplified DNA binding subunits which provide sufficient but not extensive binding stabilization of the reversible DNA adduct might offer important advantages that relate to the inherent repair or reversal of nonproductive DNA alkylation sites. Moreover, this would also provide a further strong rationale for the use of less reactive alkylation subunits (CBI versus CPI) whose DNA adducts, while stable, are inherently less stable and more readily reversed.

The preparation of the expanded series of agents 57–61 and their corresponding seco derivatives 52–56 is summarized in FIG. 10. The simplified DNA binding subunits were assembled by coupling methyl 5-aminoindole-2-carboxylate (35) or methyl 5-aminobenzoxazole-2-carboxylate (36) with 37–39. Hydrolysis of the methyl esters 40–45 (LiOH, THF—CH$_3$OH—H$_2$O, 25° C.) followed by coupling of the carboxylic acids 46–51 with freshly generated 16 (EDCI, DMF, 25° C.) deliberately conducted in the absence of added base provided excellent yields of the seco agents 32 and 52–56. Spirocyclization of 32 and 52–56 was effected by treatment with NaH, DBN, or P$_4$-tBu and provided the agents 27 (CBI-indole$_2$) and 57–61.

The results of the cytotoxic evaluations of the agents are summarized in FIG. 11 along with those of CBI-indole$_2$ (27) and CPI-indole$_2$. Several aspects of these comparative evaluations are notable. First, the natural enantiomers are substantially more potent than the unnatural enantiomers (130–1000×). In addition, the seco agents 32 and 52–56 exhibited the same levels of cytotoxic activity as the cyclopropane containing agents where compared although this was not investigated in detail. Most notably and with the exception of 60, the cytotoxic potency of natural enantiomers of the new agents were equivalent to or exceeded those of 27 and 57 and all were 2–6× more potent than the corresponding CPI analog. Moreover, the potencies of 32 and 52–56 approach or are equivalent with the ceiling of potency observed with 25–36 (5 pM).

Although we have described an extensive account of the DNA alkylation properties of both enantiomers of 25–27, 28, and 29 elsewhere, their comparisons with the corresponding CPI-based agents and their relationship to the biological evaluations merit summarizing. In these studies, a detailed investigation leading to the definition of the 3.5–5 base pair AT-rich adenine N3 alkylation selectivity of the agents were disclosed for both the natural and unnatural enantiomers, models were disclosed which accommodate the reversed binding orientations and offset AT-rich alkylation selectivity, and a beautiful explanation emerged which explains the diminished DNA capabilities of the unnatural enantiomers. Moreover, a clearer picture of the origin of the DNA alkylation selectivity and the structural features of the agents responsible have emerged from these studies. In a detailed comparative examination of the DNA alkylation properties of the CBI-based agents and the corresponding CPI-based analog or duocarmycin SA based agent, they have been found to exhibit identical DNA alkylation selectivities. This is nicely illustrated in FIGS. 3 and 4 with the comparisons of CBI-indole$_2$ (27)/CPI-indole$_2$ (4) and CBI-TMI (29)/duocarmycin SA (2), respectively. In addition, the CBI-based agents have been shown to alkylate DNA both at a faster rate and with a greater efficiency than the corresponding CPI-based agent. This is nicely illustrated in FIG. 21 with the comparison of (+)-CBI-indole$_2$ (27) and (+)-CPI-indole$_2$ (4) where 27 is 10× more efficient at alkylating w794 (4° C. or 37° C., data for latter not shown). Moreover, when the relative rates of DNA alkylation were directly compared at the single high affinity site of w794 DNA, that of CBI-indole$_2$ was considerably faster, k(27)/k(4)=14, FIGS. 23A–23B. In contrast, the natural enantiomer of CBI-based agents and corresponding duocarmycin SA based agents have been found to alkylate w794 DNA with essentially indistinguishable efficiencies (FIG. 22) and at comparable rates, k(29)/k(2)=0.9, FIGS. 23A–23B.

In addition, because of the unnatural enantiomer sensitivity to destabilizing steric interactions surrounding the duocarmycin C7, CPI C7 or CBI C8 center, the unnatural enantiomers of the simpler CBI-based analogs are approximately 4–100× less effective than the natural enantiomers. In comparison, the unnatural enantiomers of the CPI-based analogs are 10–1000× less effective and the duocarmycin SA based analogs or agents are 1–10× less effective in both the cytotoxic assays and in their relative DNA alkylation rate or efficiency. Moreover, this distinction in the enantiomers diminishes only with the larger agents, ie. 25, where the extensive noncovalent binding interactions are sufficiently large to overcome the destabilizing steric interactions of the unnatural enantiomer alkylation. Importantly, these trends follow closely the relative cytotoxic potency of the agents, the relative stabilities of the three classes of agents, and highlight the enhanced distinctions of the CBI- versus CPI-based analogs and the comparable properties of the duocarmycin SA and CBI-based agents. Fundamental to members of this class of antitumor antibiotics, the natural enantiomers of the agents were found to follow a well-defined relationship between solvolysis (functional) stability (−log k, pH 3) and cytotoxic potency (1/log IC$_{50}$, L1210) where the chemically more stable agents within a given class exert the greatest potency, FIGS. 24A–24E. FIGS. 24A–24E include data for 4–6 available classes of agents that bear five different DNA binding subunits which we have examined, and although this relationship is undoubtedly a second order polynomial indicative of a parabolic relationship that will exhibit an optimal stability-reactivity/potency, the agents employed in FIGS. 24A–24E lie in a near linear range of such a plot. What is unmistakable in the comparisons, is the fundamental direct correlation between functional (solvolytic) stability and cytotoxic potency.

CBI-CDPBO$_1$ and CBI-CDPBI$_1$: Deep-Seated Structural Variations in the DNA Binding Subunits. The efforts of Lown and Dervan have demonstrated that the distamycin AT-rich noncovalent binding selectivity may be altered to accommodate a G-C base-pair or to exhibit progressively altered AT-GC rich binding selectivity through introduction of a nitrogen within the backbone core structure capable of serving as hydrogen bonding acceptor. Accordingly, we have investigated whether similar changes in the core structure of CC-1065 would impact on its DNA binding selectivity and resulting DNA alkylation selectivity. Key to the importance of this examination was the recognition that the more rigid structure of CC-1065, its rigid helical bound conformation, and its near exclusive dependence on stabilizing van der Waals contacts and hydrophobic binding which dictates the preference for binding and alkylation within the narrower, deeper AT-rich minor groove may not be so easily overridden by introduction of a single hydrogen bond acceptor or donor.

In the conduct of these studies, we reported the preparation of (+)- and ent-(−)-CBI-CDPBO$_1$ (62), (+)- and ent-(−)-CBI-CDPBI$_1$ (64) and their corresponding seco precursors 63 and 65 bearing deep-seated modifications in the DNA binding subunit including the incorporation of a nitrogen atom capable of functioning as a hydrogen bond acceptor (CDPBO, CDPBI) or hydrogen bond donor (CDPBI) on their inside convex face which is projected to be in intimate contact with the minor groove floor.

The initial comparisons were made with agents containing a single DNA binding subunit where the single deep-seated structural modification in the DNA binding subunit might be expected to exert a more pronounced effect. In these studies, the DNA alkylation selectivities and efficiencies of the natural enantiomers of 62 and 64 were found to be essentially identical. Moreover, both were approximately 100× less efficient at alkylating DNA than (+)-CBI-CDPI$_1$ (26). Thus, the simple incorporation of a single nitrogen into 64 versus 26 has a pronounced and detrimental effect on the relative efficiency of DNA alkylation. Identical to trends detailed in our prior work on the CBI-derived agents, the unnatural enantiomers of 62 abd 64 proved to be 10–100× less efficient at alkylating DNA than the corresponding natural enantiomers.

More interesting was the observed DNA alkylation selectivities of 62 and 64. The DNA alkylation selectivities of (+)-62 and (+)-64 were essentially identical and both were comparable to the selectivity observed with (+)-26. Although the DNA alkylation selectivity of (+)-62 and (+)-64 potentially could have been significantly altered or have become increasingly more tolerant of a GC base-pair in the alkylation sequence, the selectivity proved more revealing than this simple expectation. Not only did (+)-62 and (+)-64 alkylate DNA with the near identical selectivity of (+)-26, but the unnatural enantiomer selectivity for 62 and 64 proved essentially identical to that of ent-(−)-26. Thus, in a manner essentially identical to (+)- and ent-(−)-26 which exhibit distinct alkylation selectivities (5'-A/TA/TA/T$\underline{A}$ versus 5'-A/T$\underline{AA}$/TA/T, respectively) characteristic of the reverse binding orientations and offset 3.5 base-pair AT-rich binding sites surrounding the alkylation site, the two enantiomers of 62 and 64 alkylated essentially the same sites as the corresponding enantiomers of 26 within duplex DNA. Moreover, this was observed to occur not with the increasing tolerance for incorporation of GC base-pairs in the alkylation sequence, but rather with a diminished DNA alkylation efficiency (100×) relative to that of (+)- and ent-(−)-CBI-CDPI$_1$ (26). The potential origin of these effects have been discussed elsewhere.

The cytotoxic properties of 62–65 and that of the closely related CBI agents are summarized in FIG. 13. Consistent with their relative efficiencies of DNA alkylation, the natural enantiomers of 62 and 64 were essentially indistinguishable (500–1000 pM, L1210) and 100–200× less potent than (+)-CBI-CDPI$_1$ (26). Thus, the introduction of the single nitrogen atom in the DNA binding subunit of 64 reduced the biological potency 100 to 200-fold. Consistent with prior observations, the natural enantiomers of 62 and 64 were 10–100× more potent than the corresponding unnatural enantiomers. CBI-Indole-NMe$_3^+$: Electropositive Substituents Capable of Enhancing DNA Alkylation Efficiency Through Stabilizing Electrostatic Interactions. In recent studies, we have studied the impact that electronegative and electropositive substituents placed on peripheral face of the agents have on the noncovalent DNA binding affinity and selectivity. In these studies, we defined a destabilizing contribution to the DNA binding affinity that results from the introduction of a strong electronegative substituent and described a substantial enhancement of noncovalent binding affinity that results from introduction of an electropositive substituent. This was attributed to a spatially well-defined destabilizing or stabilizing electrostatic interaction with the negatively charged DNA phosphate backbone, respectively, and was found to have little impact on the intrinsic AT-rich binding selectivity of the parent agents. These studies were recently extended to the preparation of 66–68, close analogs of 28/33, containing a peripheral quaternary ammonium salt capable of providing a strong, stabilizing electrostatic interaction with the DNA phosphate backbone. Consistent with expectations, the agents 66–68 alkylated DNA with the same relative efficiency as 1–2 and were approximately 100× more effective than 28 or 33 which lack the ammonium salt substituent. Because of the smaller size of the agents, they exhibited a DNA alkylation selectivity that was subtly altered from that of (+)-CC-1065, but comparable to that of (+)-duocarmycin SA. In addition, the agents were water soluble and offer potential advantages over the existing agents.

Consequently, we were interested in the relative cytotoxic properties of 66–68 and the results of their evaluations are summarized in FIG. 15. Although 66–68 were essentially identical in their cytotoxic potencies (10 nM), they proved to be slightly less potent than (+)-CBI-indole$_1$ (28) and approximately 1000× less potent than (+)-1 and (+)-2. This is in contrast to expectations based on their relative efficiencies of DNA alkylation. Although this was not investigated, we attribute this diminished cytotoxic potency to ineffective cellular penetration required for the agents to reach their intracellular target.

Additional Analogs. In the course of our investigations, several additional agents have been examined including 73 and 75, simple derivatives of the CBI alkylation subunit which possess enhanced DNA alkylation capabilities and in vitro cytotoxic potency by virtue of stabilizing electrostatic DNA binding. That is, in place of the DNA binding affinity derived from hydrophobic binding and stabilizing van der Waals contacts provided by the central and right-hand subunits of 1–3, the simple electrostatic binding affinity provided by the protonated amine of 73 and 75 with the negatively charged phosphate backbone of DNA proved sufficient to substantially enhance the DNA alkylation intensity and in vitro cytotoxic activity.

The semicarbazide of CBI and its seco chloride precursor were prepared as detailed in FIG. 16. Treatment of bis(2,4-dinitrophenyl)carbonate (69) with tert-butylcarbazate (70, 1 equiv, 24° C., 2 h, EtOAc) provided 71 (61%) and a convenient acylating agent for introduction of the tert-butyloxycarbonyl protected hydrazide. N-deprotection of 15 (3 N HCl-EtOAc, 24° C., 20 min, 100%) followed by immediate treatment of the unstable amine hydrochloride salt 16 with 71 (1.3 equiv, 1 equiv Et$_3$N, 24° C., 5.5 h, THF, 91%) provided 72 in excellent yield. Acid-catalyzed N-BOC deprotection of 72 provided 73 and exposure of 72 or 73 to 5% aqueous NaHCO$_3$-THF (24° C.) provided 74 or 75, respectively.

The results of the in vitro cytotoxic evaluation of the N-semicarbazide of CBI conducted on its more stable seco precursor 73 are detailed in FIG. 18 along with the comparative results from the evaluation of N-BOC-CBI (15) and 72. Notably, 73 which possesses the free amine exhibited more potent in vitro cytotoxic activity than its precursor possessing the tert-butylcarbazate (72, ca. 100×) or N-BOC-CBI (9) itself, and proved to be only 100× less potent than (+)-CC-1065.

Consistent with the trends observed in the relative cytotoxic potency of the agents, the intensity of DNA alkylation similarly increased with the introduction of the free semicarbazide and the results of these studies have been detailed elsewhere. Thus, the introduction of a positively charged functionality (protonated amine) onto the simple CBI alkylation subunit served to enhance the DNA alkylation intensity of the agent presumably by providing noncovalent electrostatic DNA binding affinity to the agents. Consistent with the enhancement in the DNA alkylation intensity (100×), the in vitro cytotoxic activity of the agents increased correspondingly (100×).

The introduction of a terminal semicarbazide onto CBI-CDPI$_2$ was carried for comparison purposes (FIG. 17). Acid-catalyzed deprotection of N-BOC-CDPI$_2$ (76, CF$_3$CO$_2$H, 25° C., 1 h) followed by coupling of crude amine salt with 71 (1.5 equiv, 1 equiv Et$_3$N, 25° C., 19 h, 91% overall) provided 77 in excellent conversion. Direct coupling of 77 with freshly generated 16 (3 equiv EDCI, DMF, 25° C., 10 h) provided 78 (65%) in good conversions. Acid-catalyzed deprotection (3M HCl-EtOAc, 25° C., 30 min) cleanly provided 79 (95–100%).

The examination of 78 and 79 revealed that this alteration in the C-terminus of CBI-CDPI$_2$ (25) did not impact on the inherent properties of the agent, FIG. 18. Thus, in contrast to 73 where the introduction of a stabilizing electrostatic interaction enhances the DNA alkylation efficiency and cytotoxic potency of the agent, it had no impact on the properties of 79 versus 78/25. Presumably, this may be attributed to the fact that the noncovalent hydrophobic binding affinity of 25 is already sufficient to provide fuill stabilization of the reversible DNA adduct and the maximal cytotoxic potency and that the additional electrostatic stabilization provided in 79 is unnecessary.

Notably, the terminal acyl hydrazides of 73, 75 and 79 may serve as useful functionality for subsequent reversible or irreversible conjugation with tumor selective delivery systems and such studies are underway.

In contrast to early speculation, deep-seated modifications in the CC-1065 and duocarmycin alkylation subunit are well tolerated and the CBI-based analogs proved to be potent cytotoxic agents and efficacious antitumor compounds. A direct relationship between functional stability and cytotoxic potency was defined and validated. As such, the readily accessible CBI-based analogs were found to be 4× more stable and 4× more potent than the corresponding analogs containing the CPI alkylation subunit of CC-1065 and comparable in potency to the agents containing the duocarmycin SA alkylation subunit. Similarly, the CBI-based agents alkylate DNA with an unaltered sequence selectivity at an enhanced rate and with a greater efficiency than the corresponding CPI analogs and were comparable to the corresponding DSA analog. Systematic modification and simplification of the attached DNA binding subunits have provided a series of synthetic and potent cytotoxic agents including 25–29 and 57–61 whose biological profile are under further study. A number of the agents detailed herein exhibit potent and efficacious antitumor activity.

One aspect of the invention is directed to a compound represented by the following structure:

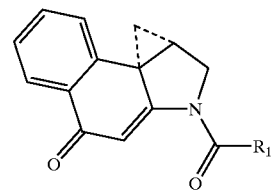

wherein R$_1$ is selected from the group consisting of —CH$_2$CH$_3$ (alkyl), —NHCH$_3$ (-N-alkyl), —OCH$_3$ (O-alkyl), —NH$_2$, —NHNH$_2$, —NHNHCO$_2$'Bu, and a radical. The radical is represented by the following structure:

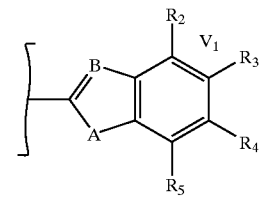

wherein A is selected from the group consisting of NH and O; B is selected from the group consisting of C and N; R$_2$ is selected from the group consisting of hydrogen, hydroxyl, O-alkyl (C1–C6), N-alkyl (C1–C6)$_3$ and a first N-substituted pyrrolidine ring; R$_3$ is selected from the group consisting of hydrogen, hydroxyl, O-alkyl (C1–C6), N-alkyl (C1–C6)$_{31}$ the first N-substituted pyrrolidine ring; R$_4$ is selected from the group consisting of hydrogen, hydroxyl, O-alkyl (C1–C6), and N-alkyl (C1–C6)$_3$; R$_5$ is selected from the group consisting of hydrogen, hydroxyl, O-alkyl (C1–C6), and N-alkyl (C1–C6)$_3$; and V$_1$ represents a first vinylene group between R$_2$ and R$_3$. The following provisos apply: if R$_2$ participates in the first N-substituted pyrrolidine ring, then R$_3$ also particlates in the first N-substituted pyrrolidine ring; if R$_3$ participates in the first N-substituted pyrrolidine ring, then R$_2$ also particlates in the first N-substituted pyrrolidine ring; if R$_2$ and R$_3$ participate in the first N-substituted pyrrolidine ring, then R$_4$ and R$_5$ are hydrogen; and if R$_2$ is hydrogen, then R$_4$ and R$_5$ are hydrogen and R$_3$ is N-alkyl (C1–C6)$_3$. The first N-substituted pyrrolidine ring is fused to the first vinylene group between R$_2$ and R$_3$ and is represented by the following structure:

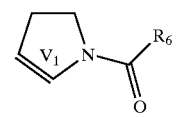

wherein V$_1$ represents the first vinylene group between R$_2$ and R$_3$; R$_6$ is selected from the group consisting of —CH$_2$CH$_3$ (alkyl), —NHCH$_3$ (-N-alkyl), —OCH$_3$ (O-alkyl), —NH$_2$, —NHNH$_2$, —NHNHCO$_2$'Bu, and a radical. The radical is represented by the following structure:

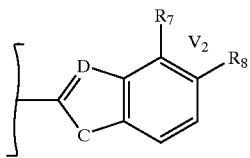

wherein C is selected from the group consisting of NH and O; D is selected from the group consisting of C and N; $R_7$ is selected from the group consisting of hydrogen, hydroxyl, O-alkyl (C1–C6), N-alkyl (C1–C6)$_3$, and a second N-substituted pyrrolidine ring; $R_8$ is selected from the group consisting of hydrogen, hydroxyl, O-alkyl (C1–C6), N-alkyl (C1–C6)$_3$, the second N-substituted pyrrolidine ring; and $V_2$ represents the second vinylene group between $R_7$ and $R_8$. The following provisos apply: if $R_7$ participates in the N-substituted pyrrolidine ring, then $R_8$ also particlates in the N-substituted pyrrolidine ring; and if $R_8$ participates in the N-substituted pyrrolidine ring only if $R_7$ also particlates in the N-substituted pyrrolidine ring. The second N-substituted pyrrolidine ring is fused to the second vinylene group between $R_7$ and $R_8$ and is represented by the following structure:

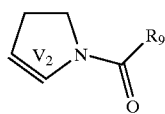

wherein $V_2$ represents the second vinylene group between $R_7$ and $R_8$; and $R_9$ is selected from the group consisting of —CH$_2$CH$_3$ (alkyl), —NHCH$_3$ (-N-alkyl), —OCH$_3$ (O-alkyl), —NH$_2$, —NHNH$_2$, and —NHNHCO$_2$$^t$Bu.

Another aspect of the invention is directed to a compound represented by the following structure:

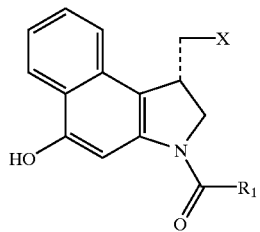

wherein X is selected from the group consisting of chlorine, bromine, iodine, and OTOS; and $R_1$ is selected from the group consisting of —CH$_2$CH$_3$ (alkyl), —NHCH$_3$ (-N-alkyl), —OCH$_3$ (O-alkyl), —NH$_2$, —NHNH$_2$, —NHNHCO$_2$$^t$Bu, and a radical. The radical is represented by the following structure:

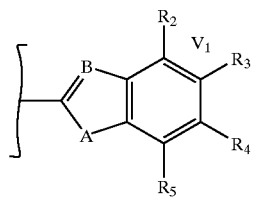

wherein A is selected from the group consisting of NH and O; B is selected from the group consisting of C and N; $R_2$ is selected from the group consisting of hydrogen, hydroxyl, O-alkyl (C1–C6), N-alkyl (C1–C6)$_3$ and a first N-substituted pyrrolidine ring; $R_3$ is selected from the group consisting of hydrogen, hydroxyl, O-alkyl (C1–C6), N-alkyl (C1–C6), the first N-substituted pyrrolidine ring; $R_4$ is selected from the group consisting of hydrogen, hydroxyl, O-alkyl (C1–C6), and N-alkyl (C1–C6)$_3$; $R_5$ is selected from the group consisting of hydrogen, hydroxyl, O-alkyl (C1–C6), and N-alkyl (C1–C6)$_3$; and $V_1$ represents a first vinylene group between $R_2$ and $R_3$. The following provisos apply: if $R_2$ participates in the first N-substituted pyrrolidine ring, then R3 also particlates in the first N-substituted pyrrolidine ring; if $R_3$ participates in the first N-substituted pyrrolidine ring, then $R_2$ also particlates in the first N-substituted pyrrolidine ring; if $R_2$ and $R_3$ participate in the first N-substituted pyrrolidine ring, then $R_4$ and $R_5$ are hydrogen; and if $R_2$ is hydrogen, then $R_4$ and $R_5$ are hydrogen and $R_3$ is N-alkyl (C1–C6)$_3$. The first N-substituted pyrrolidine ring is fused to the first vinylene group between $R_2$ and $R_3$ and is represented by the following structure:

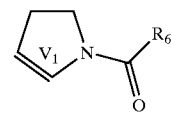

wherein $V_1$ represents the first vinylene group between $R_2$ and $R_3$; $R_6$ is selected from the group consisting of —CH$_2$CH$_3$ (alkyl), —NHCH$_3$ (-N-alkyl), —OCH$_3$ (O-alkyl), —NH$_2$, —NHNH$_2$, —NHNHCO$_2$$^t$Bu, and a radical. The radical is represented by the following structure:

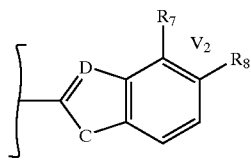

wherein C is selected from the group consisting of NH and O; D is selected from the group consisting of C and N; $R_7$ is selected from the group consisting of hydrogen, hydroxyl, O-alkyl (C1–C6), N-alkyl (C1–C6)$_3$, and a second N-substituted pyrrolidine ring; $R_8$ is selected from the group consisting of hydrogen, hydroxyl, O-alkyl (C1–C6), N-alkyl (C1–C6)$_3$, the second N-substituted pyrrolidine ring; and $V_2$ represents the second vinylene group between $R_7$ and $R_8$. The following provisos apply: if $R_7$ participates in the N-substituted pyrrolidine ring, then $R_8$ also particlates in the N-substituted pyrrolidine ring; and if $R_8$ participates in the N-substituted pyrrolidine ring only if $R_7$ also particlates in the N-substituted pyrrolidine ring. The second N-substituted pyrrolidine ring is fused to the second vinylene group between $R_7$ and $R_8$ and is represented by the following structure:

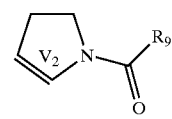

wherein $V_2$ represents the second vinylene group between $R_7$ and $R_8$; and $R_9$ is selected from the group consisting of —$CH_2CH_3$ (alkyl), —$NHCH_3$ (-N-alkyl), —$OCH_3$ (O-alkyl), —$NH_2$, —$NHNH_2$, and —$NHNHCO_2{}^tBu$.

Another aspect of the invention is directed to a compound represented by the following structure:

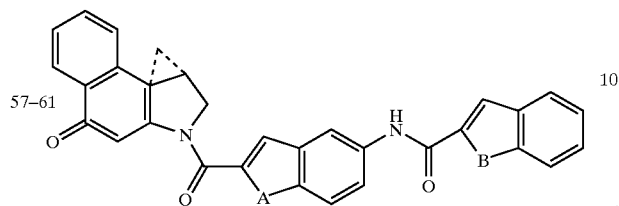

57–61 wherein A is selected from the group consisting of NH and O and B is selected from the group consisting of NH, O, and S.

Another aspect of the invention is directed to a compound compound represented by the following structure:

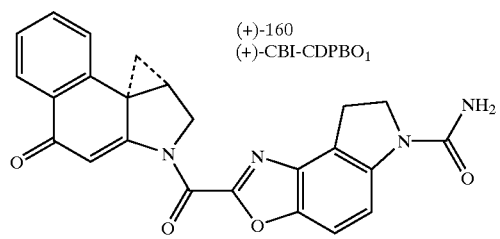

62

(+)-160
(+)-CBI-CDPBO₁

Another aspect of the invention is directed to a compound compound represented by the following structures:

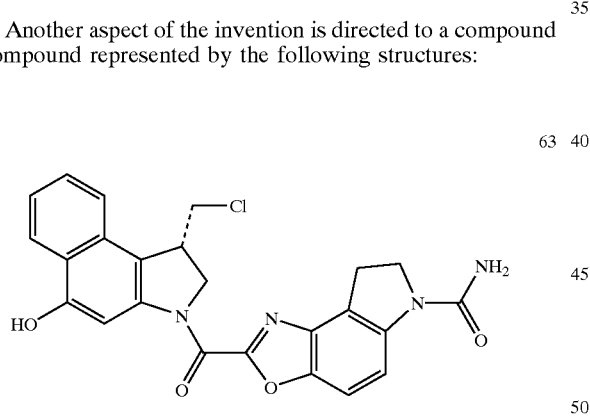

63

Another aspect of the invention is directed to a compound compound represented by the following structure:

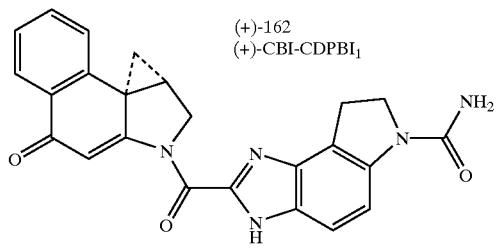

64

(+)-162
(+)-CBI-CDPBI₁

Another aspect of the invention is directed to a compound compound represented by the following structure:

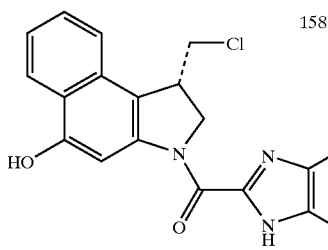

158

65

Another aspect of the invention is directed to a compound compound represented by the following structure:

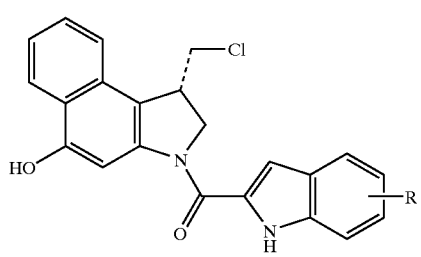

66-68 where R is selected from the group comprising of: H, 5-$NMe_3{}^+$, 6-$NMe_3{}^+$, 7-$NMe_3{}^+$.

Another aspect of the invention is directed to a compound compound represented by the following structure:

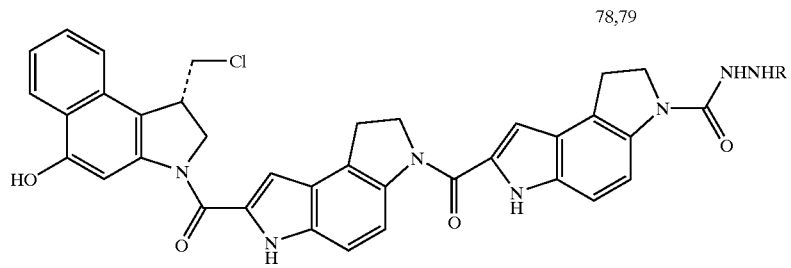

78,79 where R is selected from the group comprising of: CO$_2^t$Bu, H—HCl.

Another aspect of the invention is directed to a compound compound represented by the following structure:

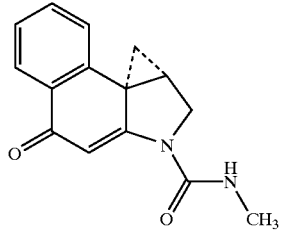

21

Another aspect of the invention is directed to a compound compound represented by the following structure:

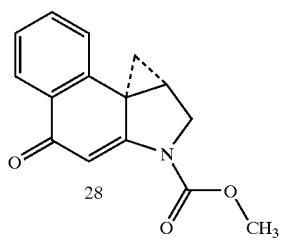

22

Another aspect of the invention is directed to a compound compound represented by the following structure:

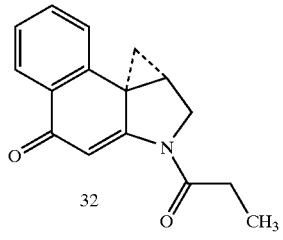

23

Another aspect of the invention is directed to a compound compound represented by the following structure:

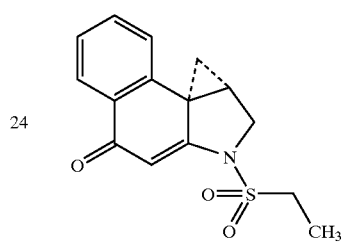

24

Another aspect of the invention is directed to a compound compound represented by the following structure:

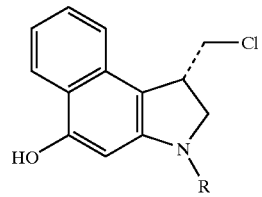

16, 18–20 where R is selected from the group comprising of: H—HCl, CONHMe, CO$_2$CH$_3$, COEt.

Another aspect of the invention is directed to a compound compound represented by the following structure:

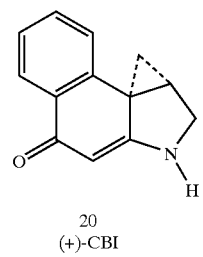

17

20
(+)-CBI

Another aspect of the invention is directed to a compound compound represented by the following structure:

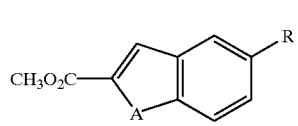

36 wherein A is selected from the group consisting of O and R is selected from the group consisting of NO$_2$ and NH$_2$.

Another aspect of the invention is directed to a compound compound represented by the following structure:

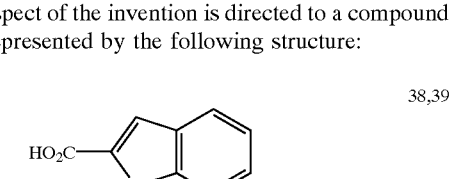

38,39 wherein B is selected from the group consisting of O and S.

Another aspect of the invention is directed to a compound compound represented by the following structure:

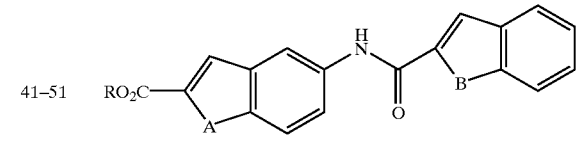

41–51 wherein A is selected from the group consisting of NH and O and B is selected from the group consisting of NH, O, and S and R is selected from the group consisting of H and CH$_3$.

Another aspect of the invention is directed to a compound compound represented by the following structure:

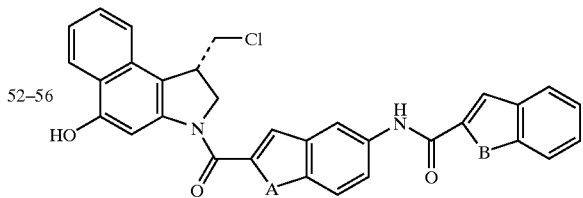

wherein A is selected from the group consisting of NH and O and B is selected from the group consisting of NH, O, and S.

DESCRIPTION OF FIGURES

FIG. 2 illustrates the structures of adozelesin (derivatives 4 and 5), carzelesin (6) and KW-2189 (8).

FIGS. 5A–5B illustrate the synthesis of compounds 16, 20, 22, 24, 26, 28, 30, 32 and 34 with the indicated intermediates, substrates, and intermediate steps.

FIG. 7 illustrates a summary of the cytotoxic activity ($IC_{50}$ (L1210, nM)) of the set of agents examined and the comparison with the related CPI-based agents. Agents are indicated as natural or unnatural.

FIG. 8 illustraes the structures of CBI analogs 25–29 and the intermediate CBI analogs 30–34 with the indicated R groups.

FIG. 9 illustrates a summary of the comparative cytotoxic activity ($IC_{50}$ (L1210, nM)) of prior agents prepared in our studies. Agents are indicated as natural or unnatural.

FIG. 11 illustrates a summary of the results of the cytotoxic evaluations of the agents examined and the comparison with the related CPI-based agents. Agents are indicated as natural or unnatural.

FIG. 12 illustrates the structures of CBI analogs (+)-62, 63, (+)-64 and 65, and indicates functional groups on the CDPBO and CDPBI analogs which are H-bond acceptor and donor, respectively.

FIG. 13 illustrates a summary of the results of the cytotoxic evaluations ($IC_{50}$ (L1210, pM)) of the agents examined and the comparison with the related CPI-based agents. Agents are indicated as natural or unnatural.

FIG. 15 illustrates a summary of the relative alkylation efficiency (Rel DNA Alkylation) and representative cytotoxicity ($IC_{50}$ (L1210, nM)) of agents 66–68 which contain a peripheral quaternary ammonium salt and are close analogs with 28 (values indicated).

FIG. 18 illustrates a summary of the relative alkylation efficiency (Rel DNA Alkylation) and representative cytotoxicity ($IC_{50}$ (L1210, nM)) of agents 9, 72, 73, 78, 79, and 25.

The comparisons of 21–24 reveal a direct, linear relationship between the cytotoxic potency (L1210, log $1/IC_{50}$) and the solvolytic stability ($-\log k_{solv}$, pH 3) of the agents. Similarly, a linear relationship was found between the electron-withdrawing properties of the $N^2$ substituents (Hammett$_p$ constant) and the solvolysis reactivity ($-\log k_{solv}$, pH 3) of the agents with the strongest electron-withdrawing substituents providing the most stable agents. This latter relationship reflects the influence of the $N^2$ substituent on the ease of C4 carbonyl protonation required for catalysis of solvolysis and cyclopropyl ring cleavage with the stronger electron-withdrawing $N^2$ substituents exhibiting slower solvolysis rates. Less obvious but more fundamental, the observations were found to follow a predictable linear relationship between the cytotoxic potency (L1210, log $1/IC_{50}$) and the electron-withdrawing properties of the $N^2$ substituent (Hammett$_p$) with the strongest electron-withdrawing substituents providing the biologically most potent agents.

Figure 21:
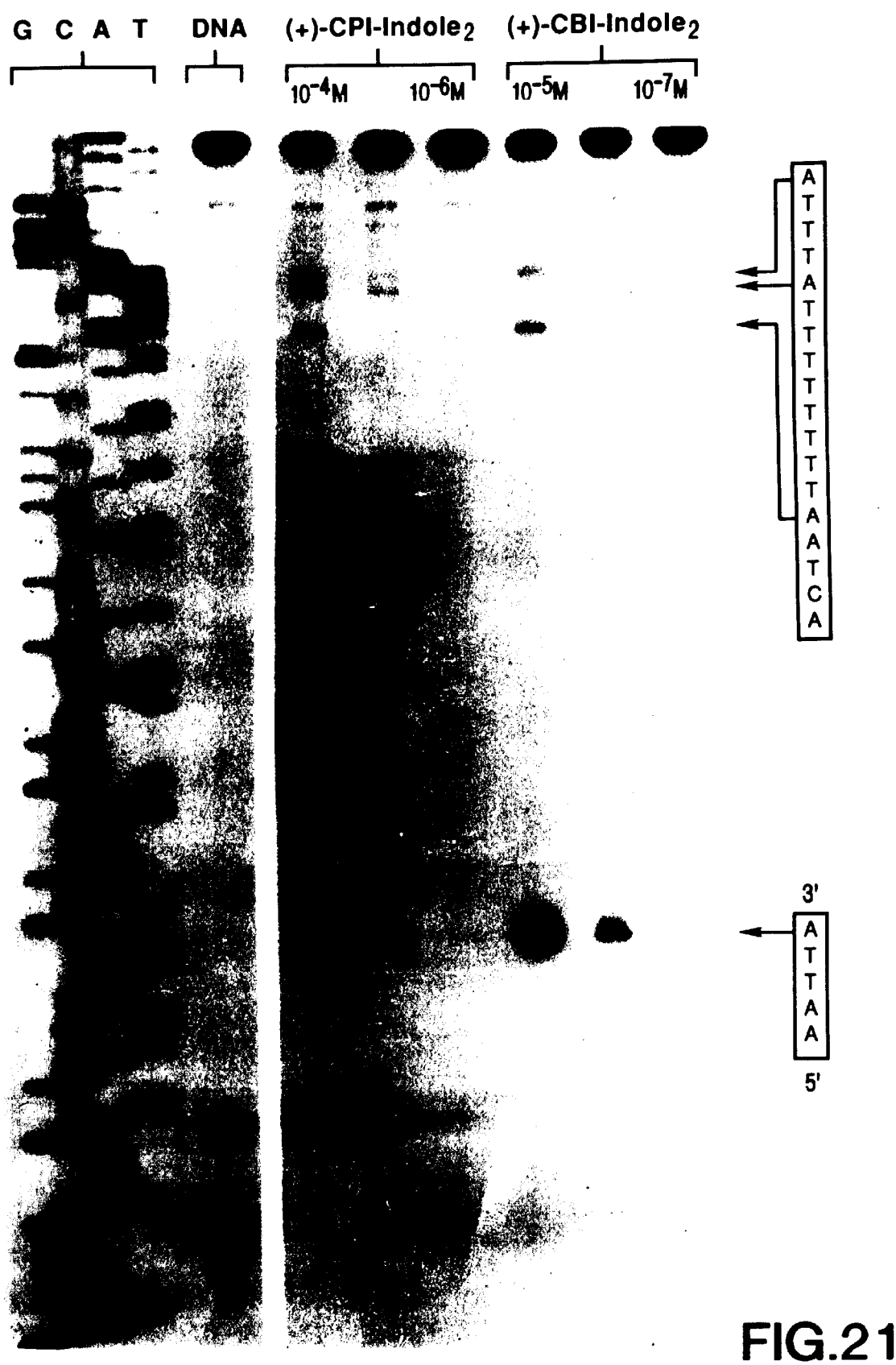

FIG. 21 illustrates the thermally-induced strand cleavage of double-stranded DNA (144 bp, nucleotide no. 138-5238, clone w794) after 24 h incubation of agent-DNA at 4° C. followed by removal of unbound agent and 30 inutes incubation at 100° C.; denaturing 8% polyacrylamide gel and autoradiography. Lanes 1–4, Sanger G,C,A, and T sequencing reactions; lane 5, control labeled w794 DNA; lanes 6–8, (+)-CPI-indole$_2$ ((+)-4, $1\times10^{-4}$–$1\times10^{-6}$ M); lanes 9–11, (+)-CBI-indole$_2$ ((+)-27, $1\times10^{-5}$–$1\times10^{-7}$ M).

Figure 22:
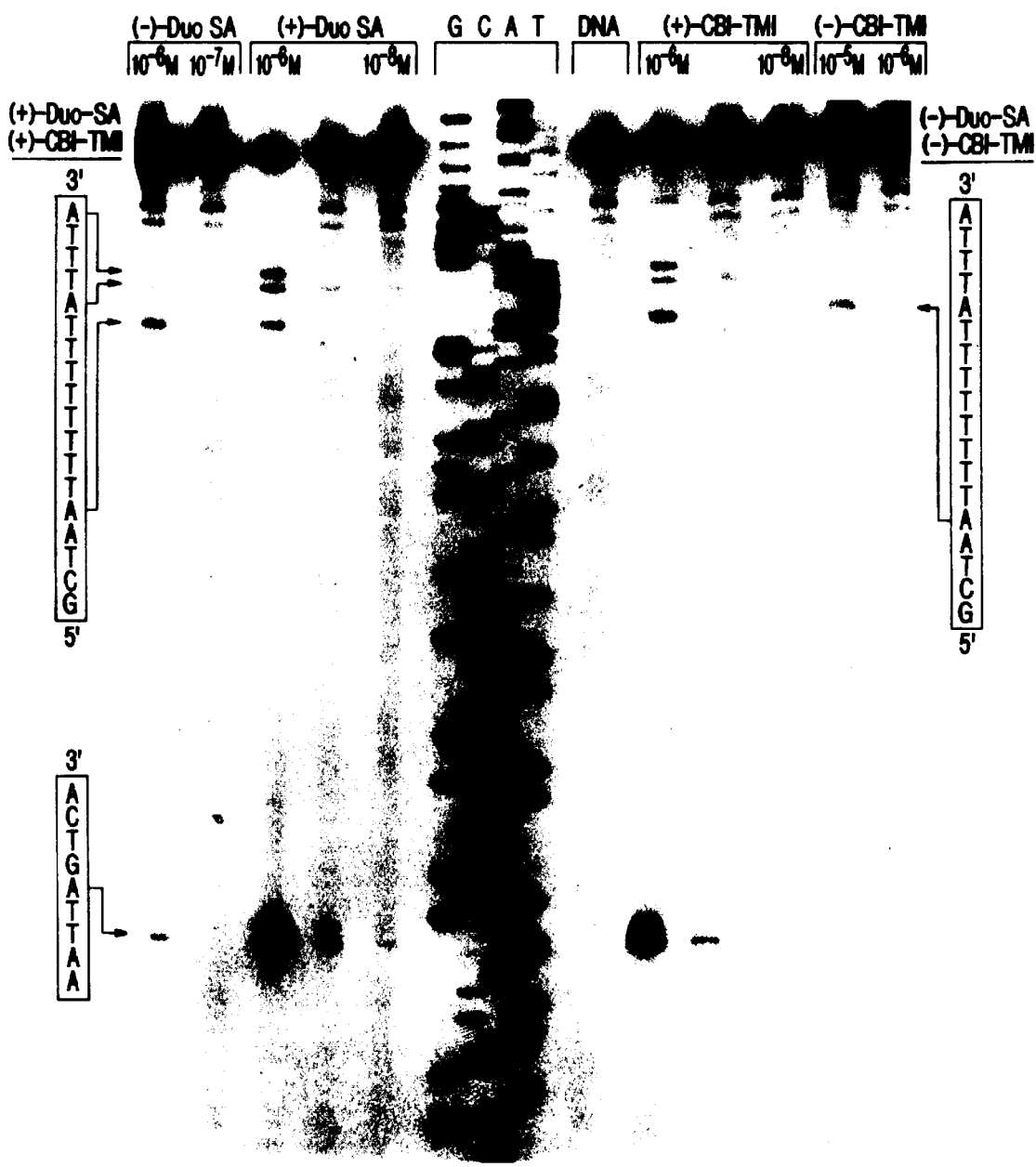

FIG. 22 illustrates the thermally-induced strand clealvage of 5' end-labeled duplex DNA (clone w794, 144 bp, nucleotide no 138-5238). Incubation of agent-DNA at 25° C. (24 h) followed by removal of unbound agent and 30 min thermolysis at 100° C., denaturing 8% PAGE, and autoradiography. Lanes 1–2, ent-(-)-duocarmycin SA ((-)-2, $1\times10^{-6}$ and $1\times10^{-7}$ M); lanes 3–5, (+)-duocarmycin SA, ((+)-2, $1\times10^{-6}$–$1\times10^{-8}$ M); lanes 6–9, G, C, A and T sequencing reactions; lane 10, control labeled w794 DNA; lanes 11–13, (+)-CBI-TMI ((+)-29, $1\times10^{-6}$–$1\times10^{-8}$ M); lanes 14–15, ent-(-)-CBI-TMI ((-)-29, $1\times10^{-5}$ and $1\times10^{-6}$ M).

Figure 23A:
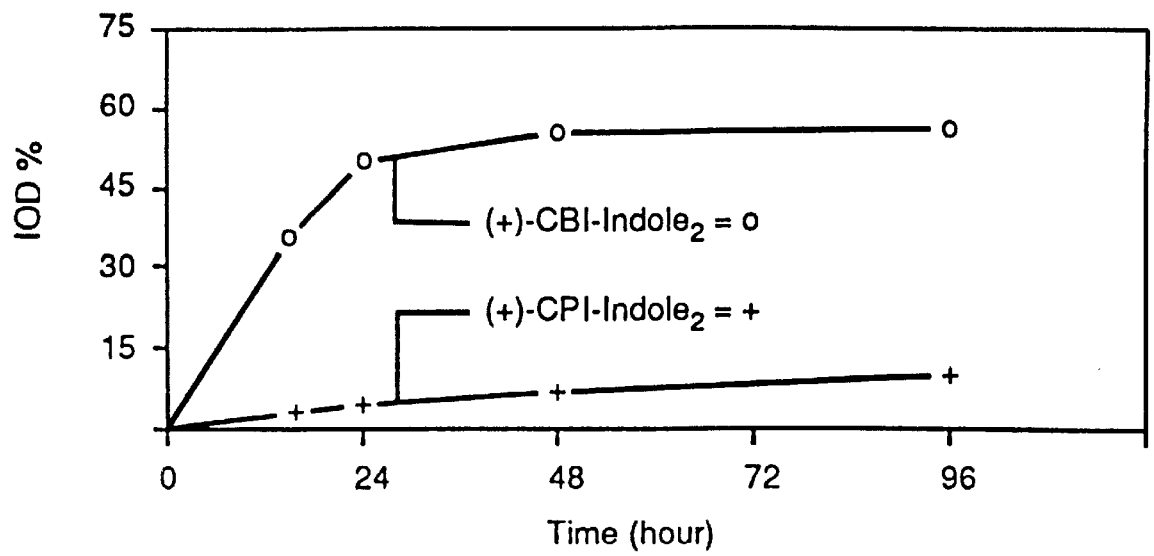
Figure 23B:
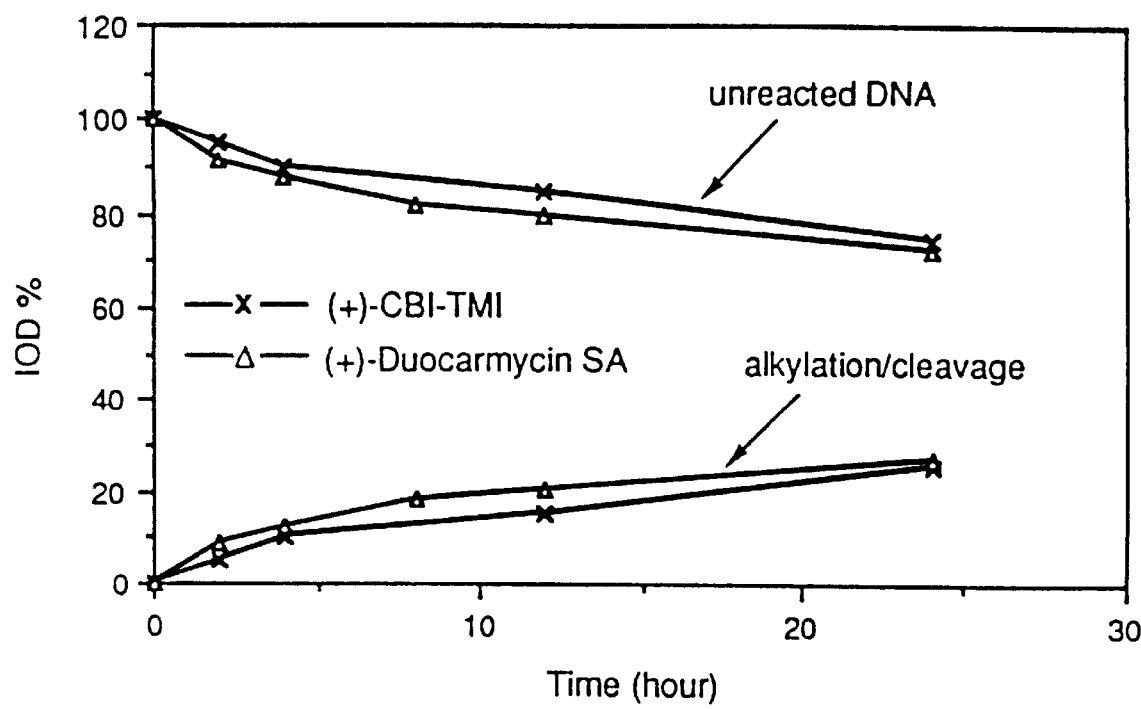
Figure 24A:
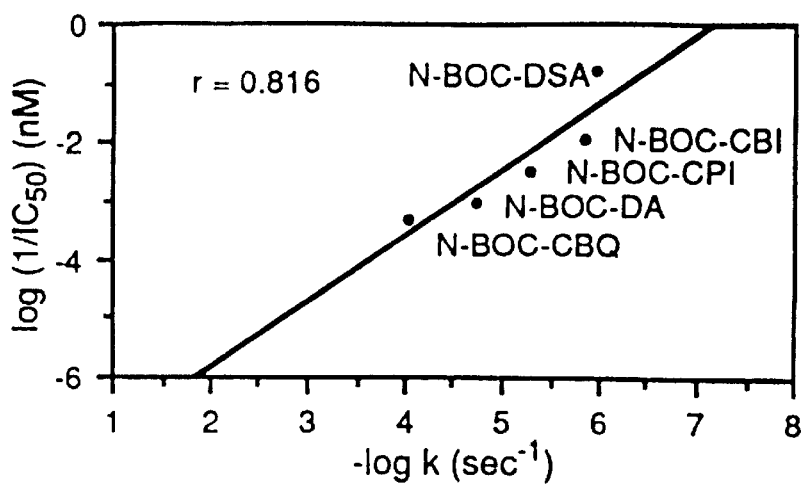
Figure 24B:
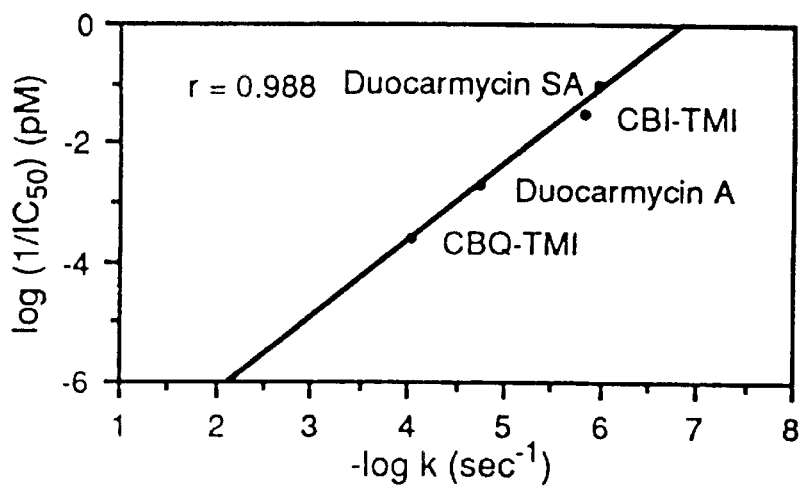
Figure 24C:
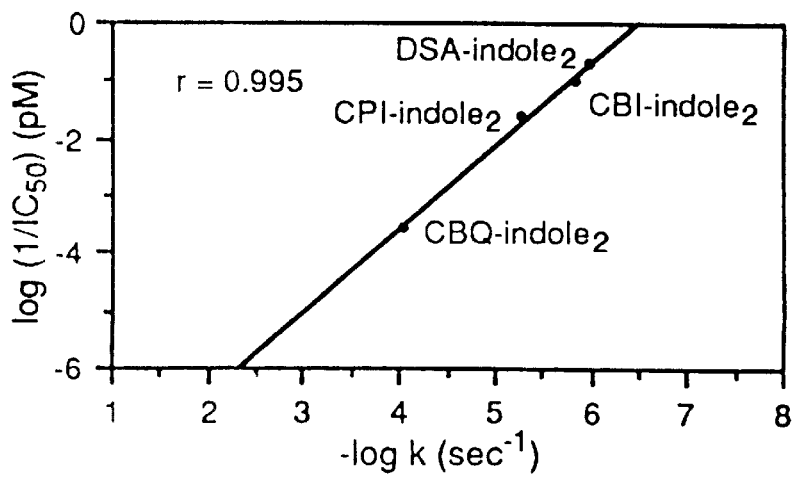
Figure 24D:
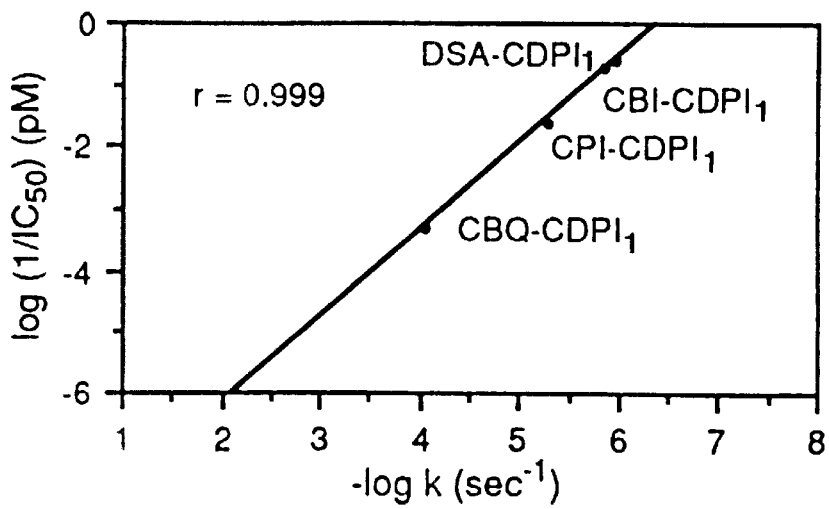
Figure 24E:
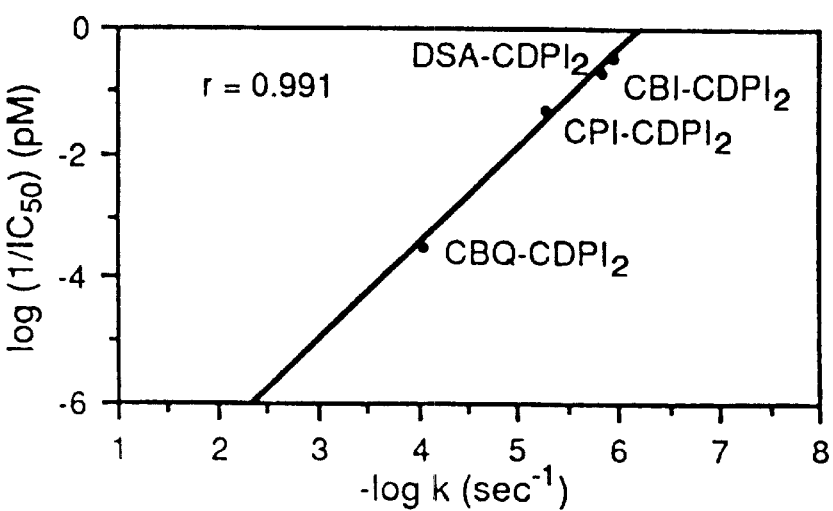

FIGS. 23A–23B represent the following: Top: Plot of % integrated optical density (% IOD) versus time established through autoradiography of 5' $^{32}$P end-labeled DNA and used to monitor the relative rate of w794 alkylation at the 5'-AATTA high affinity site for (+)-CBI-indole$_2$ (27) and (+)-CPI-indole$_2$ (4); 37° C., 0–5 d, $1\times10^{-5}$ M agent. Bottom: Plot of % integrated optical density (% IOD) versus time established through autoradiography of 5' $^{32}$P end-labeled DNA and used to monitor the relative rate of w794 alkylation at the 5'-AATT$\underline{A}$ high affinity site for (+)-duocarmycin SA (2) and (+)-CBI-TMI (29); 4° C., 0–24 h, 1×10$^{-6}$ M agent.

FIGS. 24A–24E illustrate the data for 4–6 available classes of agents that bear five different DNA binding subunits which we have examined and although this relationship is undoubtedly a second order polynomial indicative of a parabolic relationship that will exhibit an optimal stability-reactivity/potency, the agents employed in the figure lie in a near linear range of such a plot. What is unmistakable in the comparisons, is the fundamental direct correlation between functional (solvolytic) stability and cytotoxic potency.

Figure 25:
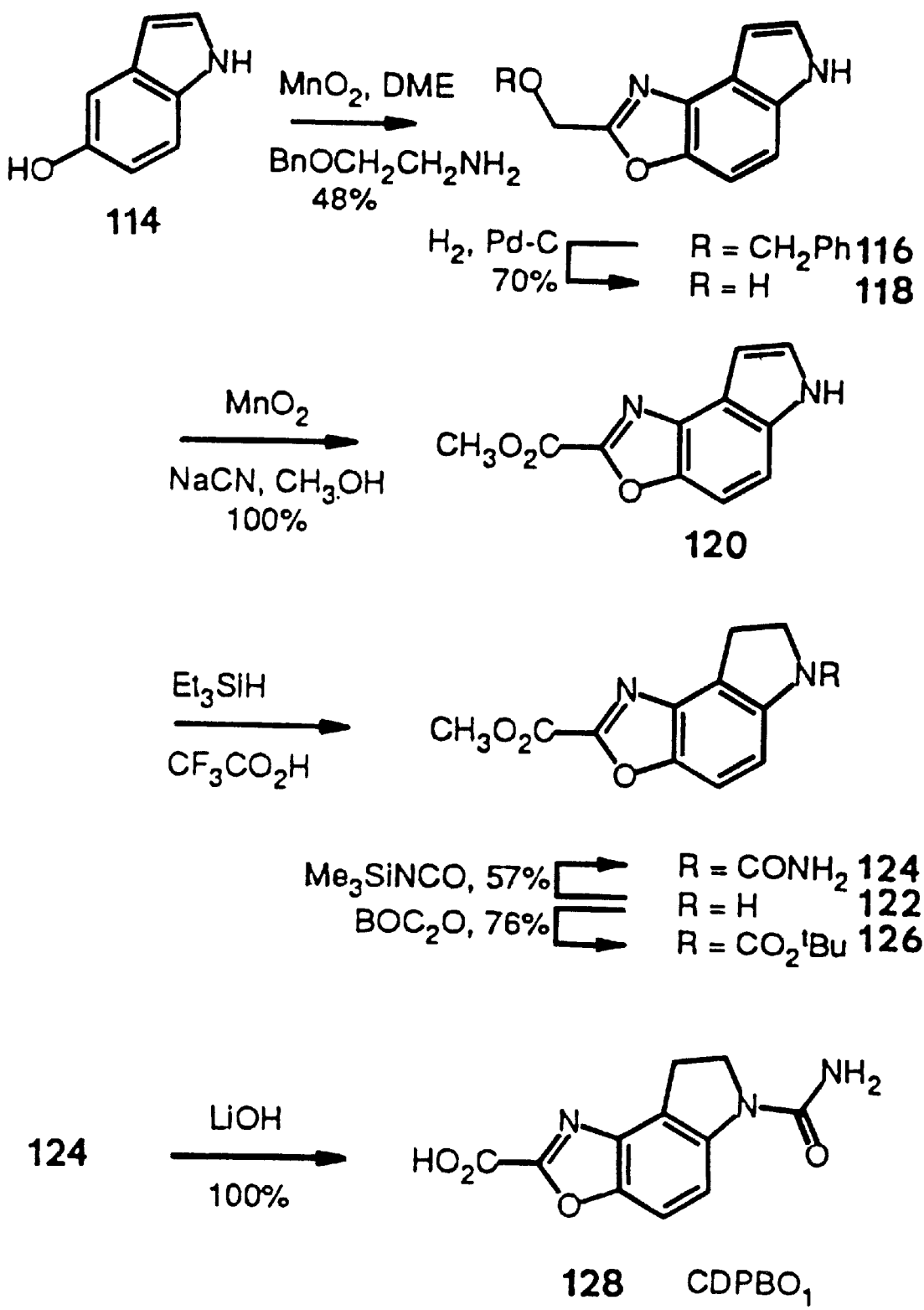

FIG. 25 illustrates the synthesis of compound 128 with the indicated intermediates, substrates, and intermediate steps.

Figure 26:
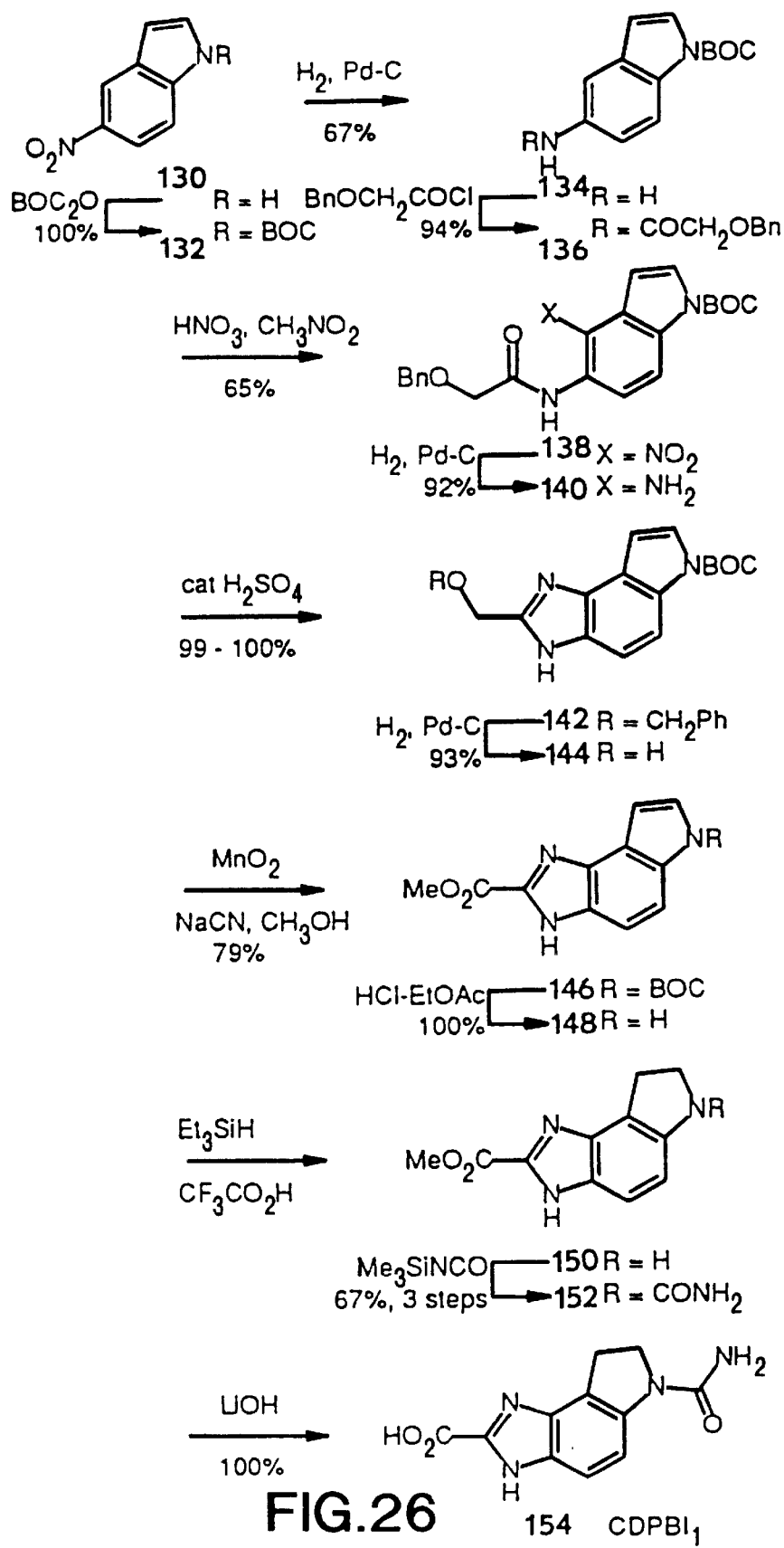

FIG. 26 illustrates the synthesis of compound 154 with the indicated intermediates, substrates, and intermediate steps.

Figure 27:
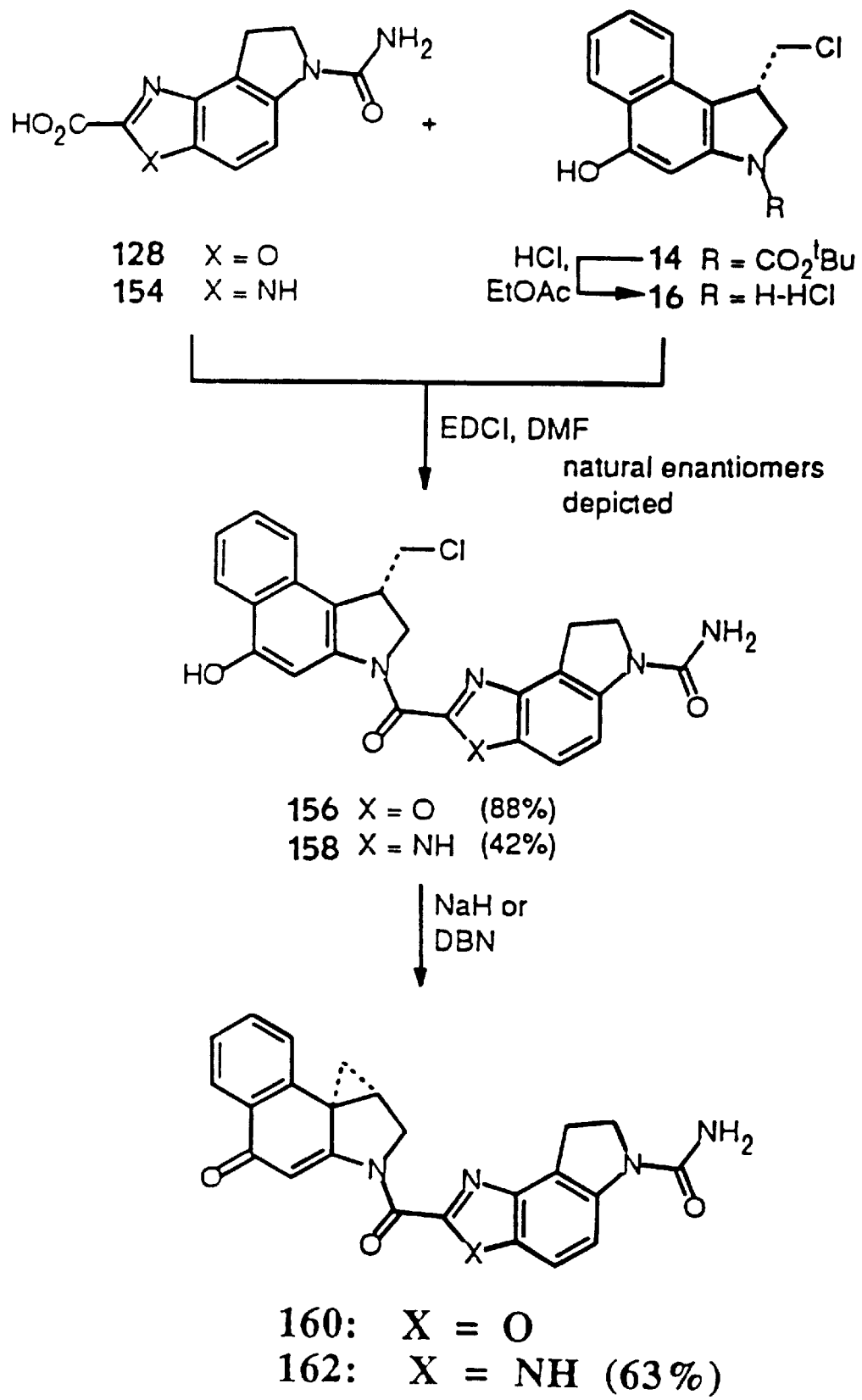

FIG. 27 illustrates the synthesis of compounds 160 and 162 with the indicated intermediates, substrates, and intermediate steps.

Figure 28B:
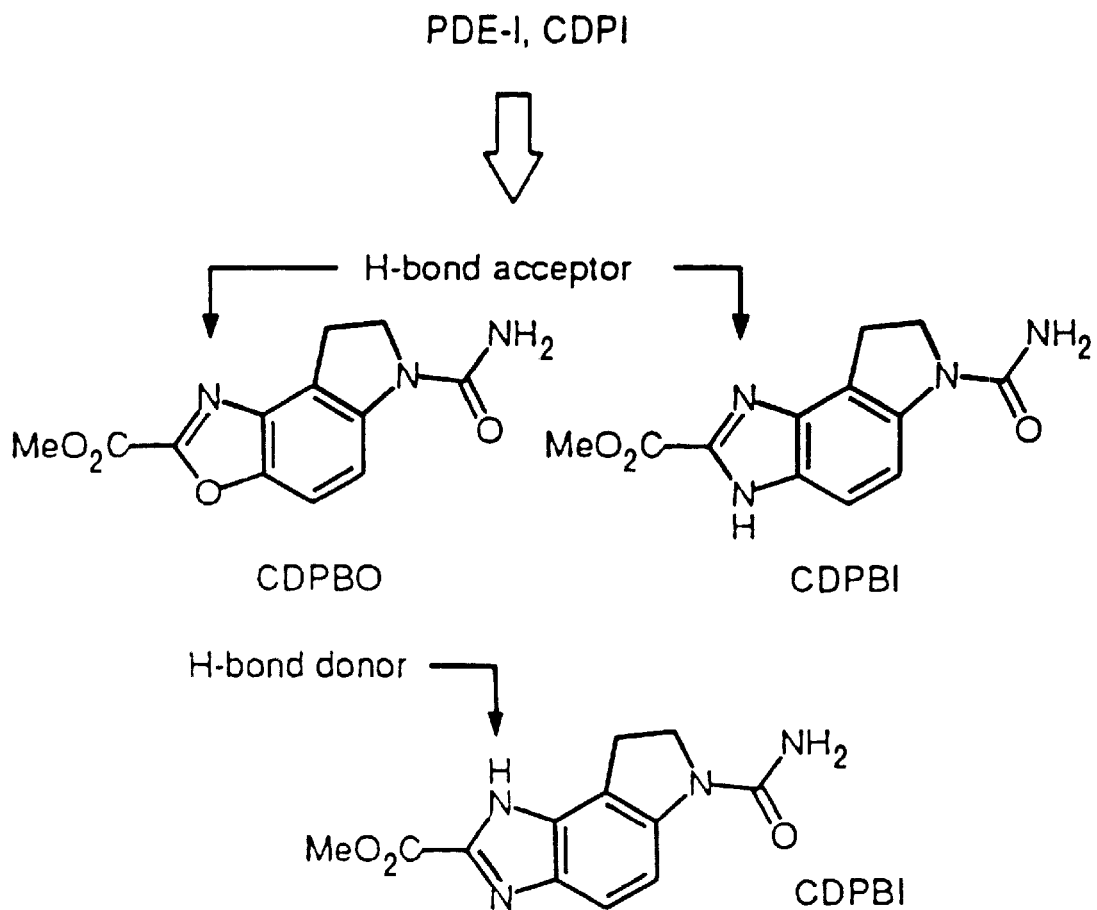

FIGS. 28A–28B illustrate the structures of CBI analogs (+)-160, intermediate 156, (+)-162 and intermediate 158, and indicates functional groups on the CDPBO and CDPBI analogs which are H-bond acceptor and donor, respectively.

Figure 29:
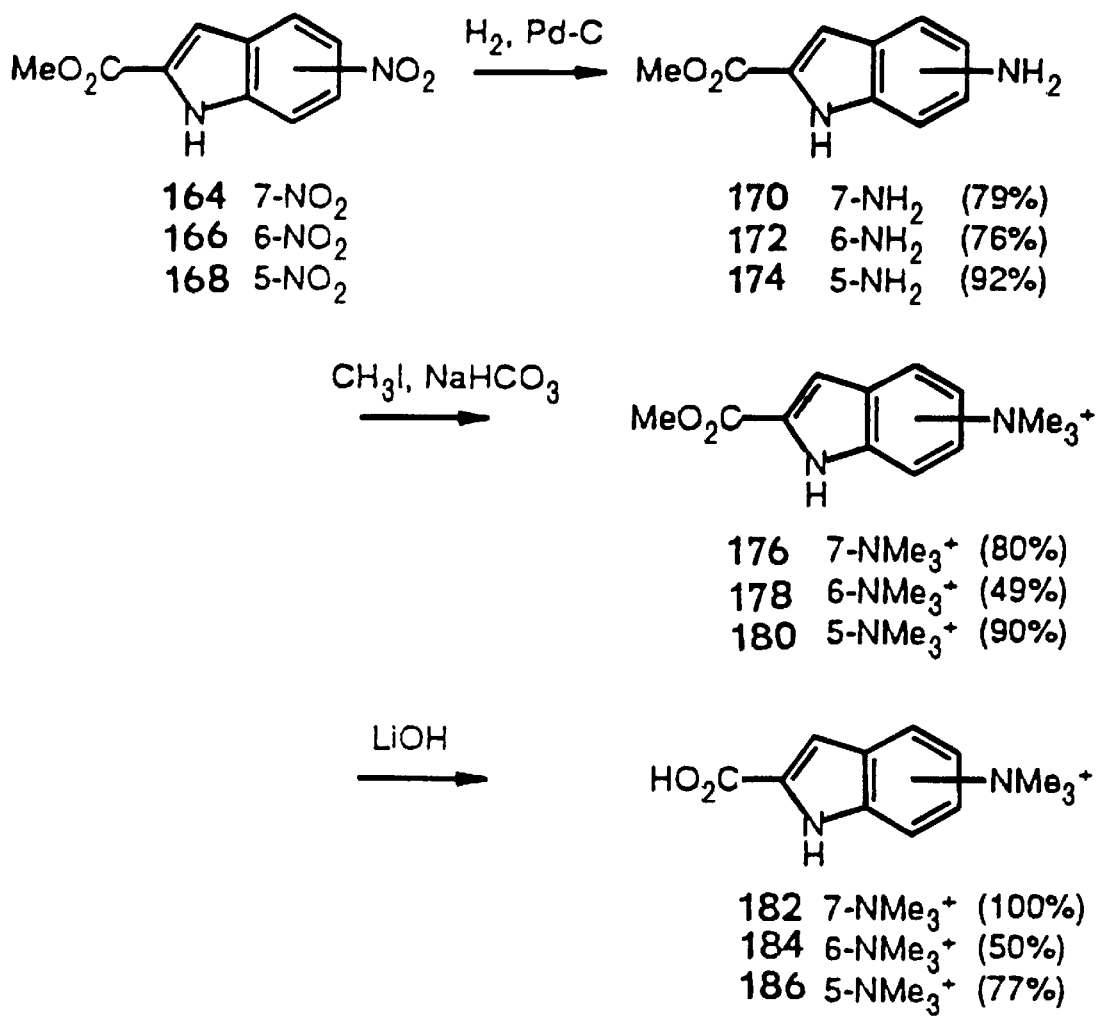

FIG. 29 illustrates the synthesis of compounds 182, 184 and 186 with the indicated intermediates, substrates, and intermediate steps.

Figure 30:
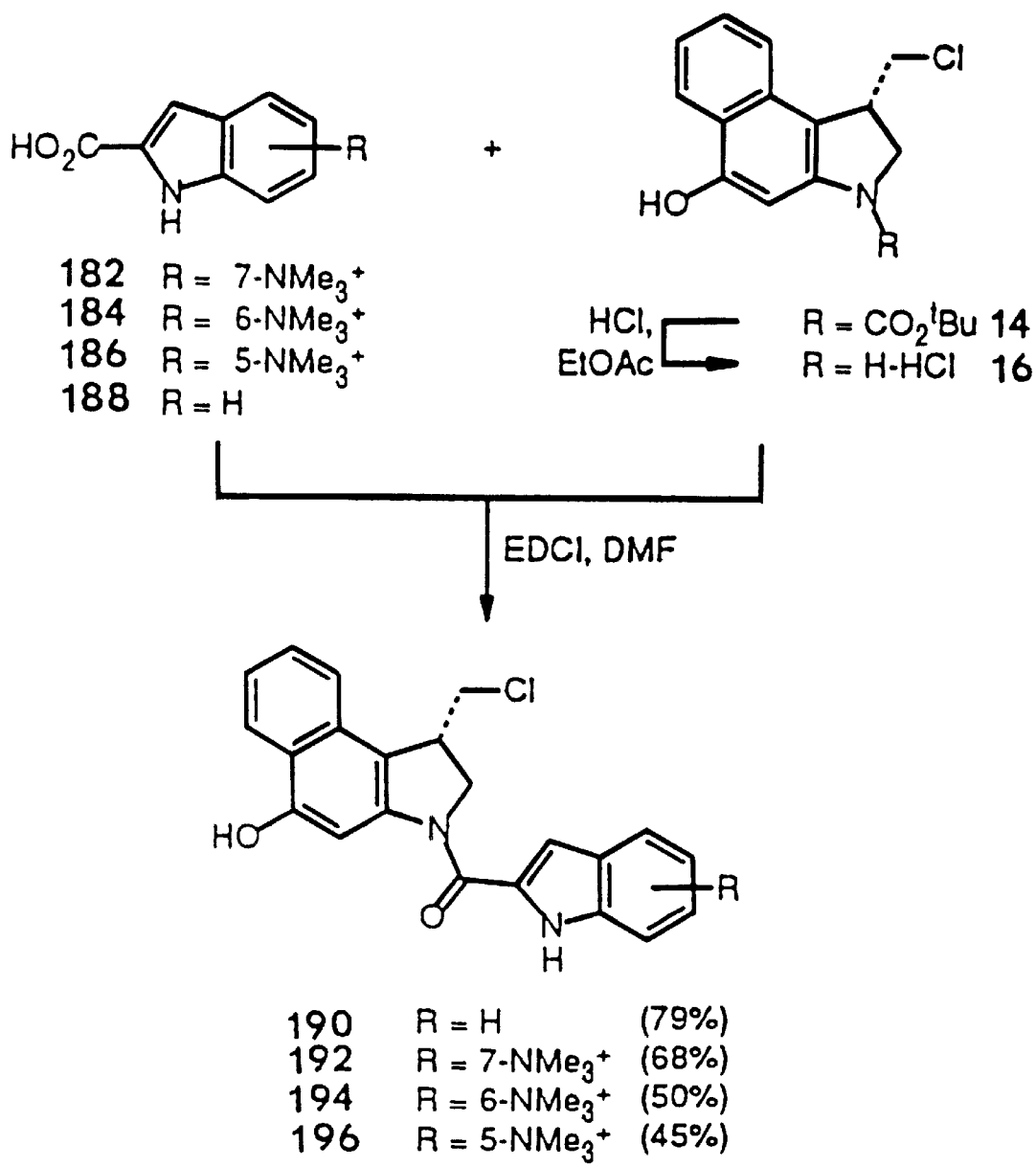

FIG. 30 illustrates the synthesis of compounds 190, 192, 194, and 196 with the indicated intermediates, substrates, and intermediate steps.

SYNTHETIC METHODS

Preparation of N-(tert-Butyloxycarbonyl)-4-benzyloxy-1-iodo-2-naphthyl-amine (4)

Figure 1:
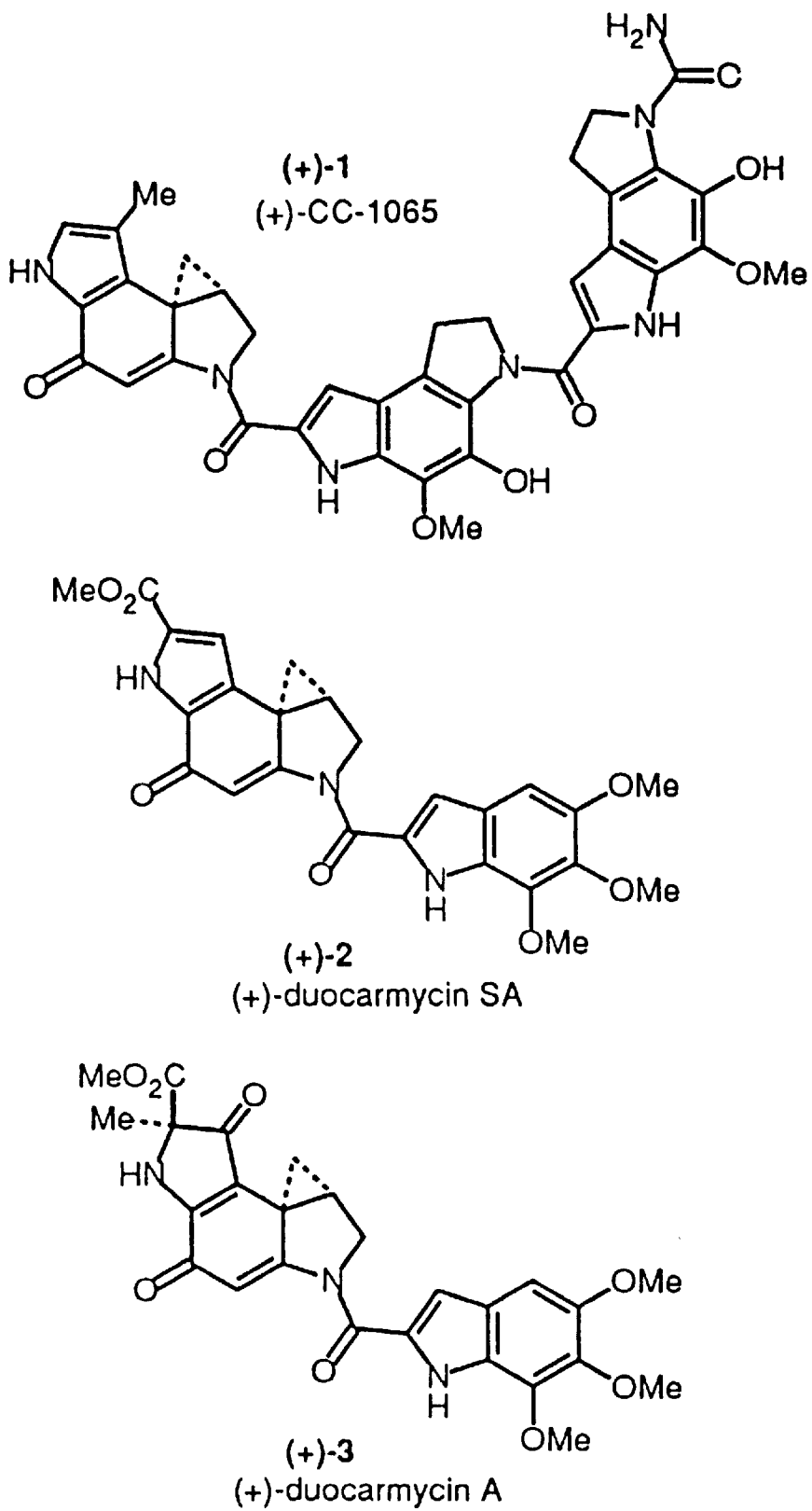
FIG. 1 illustrates the structures of (+)-CC-1065 (+)-1b, (+)-duocarmycin SA (+)-2, (+)-duocarmycin A and (+)-3.
Figure 3:
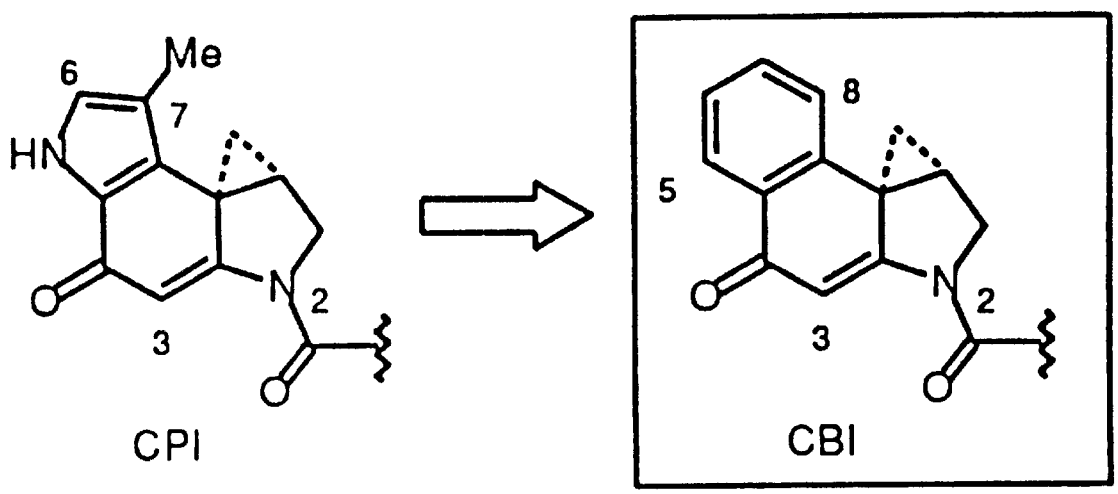
FIG. 3 illustrates the structures of CBI analogs which are based on CPI analogs.
Figure 4:
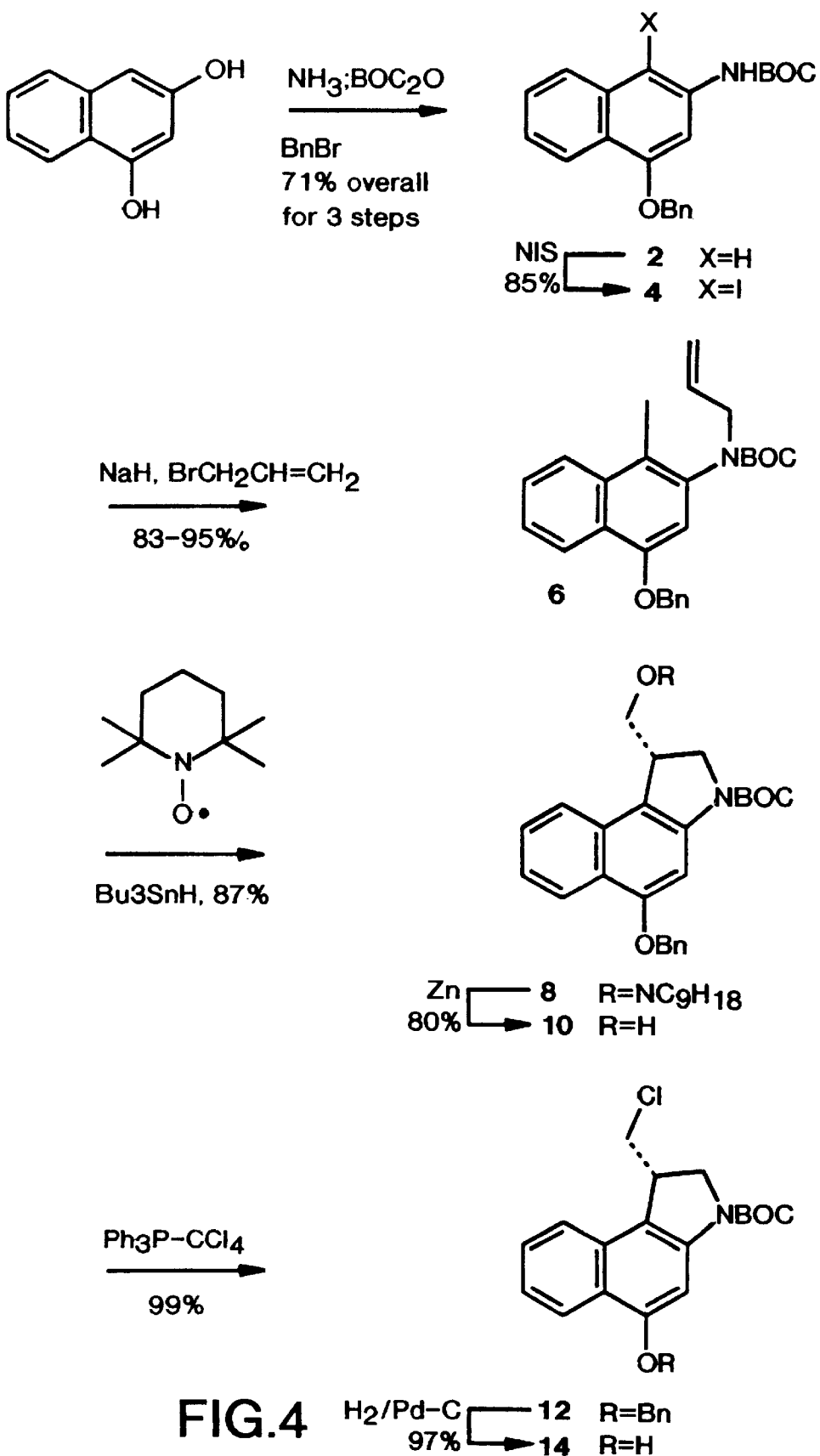
FIG. 4 illustrates the synthesis of compound 14 with the indicated intermediates, substrates, and intermediate steps.

Compound 4 (Illustrated in FIG. 4). A solution of 2 (as prepared in three steps from commercially available 1,3-dihydroxynaphthalene (71% overall), by Boger et. al. *J. Org. Chem.* 1992, 2873) (1.28 g, 3.66 mmol) in 60 mL of a 1:1 mixture of tetrahydrofuran-CH$_3$OH was cooled to −78° C. and 20 μL of H$_2$SO$_4$ (or 20 mg P-toluenesulfonic acid H$_2$O) in 0.5 mL of tetrahydrofuran was added. N-Iodosuccinimide (910 mg, 4.03 mmol) in 5 mL of tetrahydrofuran was then introduced by cannula over 5 min. Upon complete reaction (ca. 3 h at −78° C.), 10 mL of saturated aqueous NaHCO$_3$ and 50 mL of Diethyl ether were added. The reaction mixture was warmed to 25° C. and solid NaCl was added to saturate the aqueous layer. The organic layer was separated and the aqueous layer was extracted with Diethyl ether (2×10 mL). The organic layers were combined, washed with saturated aqueous NaHCO$_3$ (1×10 mL) and saturated aqueous NaCl (2×10 mL), dried (Na$_2$SO$_4$), and concentrated. The crude product was purified by elution through a short column of SiO$_2$ (2×4 cm, 20% Ethylacetate-hexane) to provide 4 (1.48 g, 85%) as a white, crystalline solid: mp 111–112° C.; $^1$H NMR (CDCl$_3$, 400 MHz) 8.21 (dd, 1H, J=8.4, 0.8 Hz), 8.03 (s, 1H), 8.01 (d, 1H, J=7.6 Hz), 7.55–7.33 (m, 7H), 7.30 (br s, 1H), 5.27 (s, 2H), 1.56 (s, 9H); $^{13}$C NMR (CDCl$_3$, 100 MHz) 155.7, 152.8, 138.3, 136.6, 134.8, 131.2, 128.7, 128.6, 128.5, 128.1, 127.8, 124.5, 123.7, 122.7, 100.0, 81.2, 70.4, 28.4; IR (film) 3384, 2974, 2923, 1739, 1617, 1598, 1567, 1515, 1494, 1444, 1392, 1366, 1332, 1226, 1152, 1107, 1082 cm$^{-1}$; FABHRMS (NBA-CsI) m/z 607.9715 (C$_{22}$H$_{22}$INO$_3$+Cs$^+$ requires 607.9699). Anal. Calcd for C$_{22}$H$_{22}$INO$_3$: C, 55.59; H, 4.67; N, 2.95. Found: C, 55.85; H, 4.43; N, 2.97.

Preparation of 2-[N-(tert-Butyloxycarbonyl)-N-(2-propenyl)]amino-4-benzyloxy-1-iodonaphthalene (6) (Illustrated in FIG. 4)

A solution of 4 (1.38 g, 2.90 mmol) in 25 mL of dimethylformamide at 0° C. was treated with NaH (60% dispersion in oil, 139 mg, 3.5 mmol) in several portions over 15 min. After 45 min, allyl bromide (1.05 g, 8.70 mmol) was added and the reaction mixture was warmed to 25° C. and stirred for 3 h. The reaction mixture was quenched by addition of 20 mL saturated aqueous NaHCO$_3$ and the aqueous layer was extracted with Ethylacetate (4×15 mL). The combined organic layers were washed with saturated aqueous NaCl (2×10 mL), dried (Na2SO$_4$), and concentrated under reduced pressure. Centrifugal thin layer chromatography (2 mm Chromatotron plate, 20–50% CH$_2$Cl$_2$-hexanes) provided 6 (1.24 g, 83%, typically 80–95%) as a colorless oil (mixture of amide rotamers in CDCl$_3$): $^1$H NMR (CDCl$_3$, 400 MHz) (major rotamer) 8.30 (d, 1H, J=8.2 Hz), 7.29 (d, 1H, J=8.2 Hz), 7.60–7.29 (m, 7H), 6.67 (s, 1H), 5.96–5.86 (m, 1H), 5.27–4.96 (m, 4H), 4.52 (dd, 1H, J=15.0, 5.7 Hz), 3.79 (dd, 1H, J=15.0, 7.2 Hz, 1.29 (s, 9H); $^{13}$C NMR (CDCl$_3$, 100 MHz) (major rotamer) 154.9, 153.8, 143.0, 136.4, 135.3, 133.5, 132.7, 128.7, 128.6, 128.4, 128.1, 127.2, 126.1, 122.4, 117.9, 108.0, 95.0, 80.3, 70.2, 52.1, 28.3; IR (film) 3048, 2976, 2923, 1703, 1590, 1403, 1367, 1326, 1251, 1147, 1105 cm$^{-1}$; FABHRMS (NBA-NaI) m/z 538.0855 (C$_{25}$H$_{26}$INO$_3$+Na$^+$ requires 538.0860).

Preparation of 5-(Benzyloxy)-3-(tert-butyloxycarbonyl)-1-(2',2',6',6'-tetramethylpiperidinyl-N-oxymethyl)-1,2-dihydro-3H-benz[e] indole (8) (Illustrated in FIG. 4)

A solution of 6 (1.85 g, 3.59 mmol) and Tempo (1.68 g, 10.8 mmol) in 120 mL of freshyl distilled benzene (Na/benzophenone) under N$_2$ was treated with Bu$_3$SnH (1.045 g, 3.59 mmol). The solution was warmed at 70° C. and three additional equivalents of Tempo (3×0.56 g) and Bu$_3$SnH (4×1.045 g) were added sequentially in four portions over the next 45 min. After 1 h, the solution was cooled to 25° C. and the volatiles were removed under reduced pressure. Centrifugal thinlayerchromatography (4 mm Chromatotron plate, 0–10% Ethylacetate-hexanes gradient elution) followed by recrystallization from hexanes provided 8 (1.71 g, 87%, typically 70–90%) as white needles: mp 170–172° C.; $^1$H NM (C$_6$D$_6$, 400 MHz) 8.56 (d, 1H, J=8.3 Hz), 8.38 (br s, 1H), 7.77 (d, 1H, J=8.4 Hz), 7.35 (ddd, 1H, J=8.3, 7.6, 1.2 Hz), 7.28 (d, 2H, J=7.0 Hz), 7.20 (t, 1H, J=7.6 Hz), 7.15 (t, 2H), 7.07 (t, 1H, J=7.2 Hz), 4.36 (m, 1H), 4.12 (dd, 1H, J=9.0, 4.5 Hz), 3.84 (m, 1H), 3.61 (m, 1H), 1.53 (s, 9H), 1.37–1.17 (m, 6H), 1.22 (s, 3H), 1.13 (s, 3H), 1.07 (s, 3H), 1.00 (s, 3H); $^{13}$C NMR (CDCl$_3$, 100 MHz) 154.1, 151.4, 140.0, 135.8, 129.4, 127.3, 126.7, 126.3, 125.8, 121.9, 121.6, 121.4, 121.1, 114.8, 95.3, 79.2, 69.0, 58.5, 51.5, 38.4, 38.3, 37.2, 31.9, 27.3, 18.9, 15.8; IR (film) 2973, 2930, 1704, 1626, 1582, 1460, 1406, 1381, 1367, 1328, 1266, 1144, 1037, 787, 759 cm$^{-1}$; FABHRMS (NBA-CsI) m/z 677.2340 (C$_{34}$H$_{44}$N$_2$O$_4$+Cs$^+$ requires 677.2355). Anal Calcd for C$_{34}$H$_{44}$N$_2$O$_4$: C, 74.97; H, 8.14; N, 5.14. Found: C, 74.68; H, 8.37; N, 5.19.

Preparation of 5-(Benzyloxy)-3-(tert-butyloxycarbonyl)-1-(hydroxy-methyl)-1,2-dihydro-3H-benz[e]indole (10) (Illustrated in FIG. 4)

A solution of 8 (1.61 g, 2.95 mmol) in 70 mL of a 3:1:1 mixture of HOAc-tetrahydrofuran-H$_2$O was treated with zinc powder (2.31 g, 35.4 g atoms) and the resulting suspension was warmed at 70° C. with vigorous stirring. After 2 h, the reaction mixture was cooled to 25° C. and the zinc was removed by filtration. The volatiles were removed under reduced pressure and the resulting residue was dissolved in 40 mL of Ethylacetate and filtered. The solution was concentrated and subjected to centrifugal thin layer chromatography (4 mm Chromatotron plate, 15–35% Ethylacetate-hexanes gradient elution) to provide 10 (0.96 g, 1.19 g theoretical, 80%) identical in all respects with authentic material (see Boger et. al *J. Am. Chem. Soc.* 1992, 114, 5487.

Preparation of Compound 12 (Illustrated in FIG. 4)

A solution of 10 (1.0 equiv.) and triphenylphosphine (2.0 equiv.) in methylene chloride (0.2 Molar) at 24° C. under argon was treated with carbon tetrachloride (6.0 equiv.) and the reaction mixture was stirred for 10 h (24° C.). Flash chromatography and resolution as derived from the cooresponding mandelate ester (see Boger et. al *J. Org. Chem.,* 1990, 55, 5830, expt. 31), affords the enantiomerically pure compound 12.

Preparation of compound 14 (Illustrated in FIG. 4)

A solution of 12 (1.0 equiv.) in 0.05 Molar tetrahydrofuran at 0° C. under argon was treated sequentially with a 25% aqueous ammonium formate (0.5 M) and 10% palladium/carbon (0.10 equiv.) and the reaction mixture stirred vigorously for 2.5 h (0° C.). Ether was mixed with the reaction mixture, and the mixture was dried (Magnesium sulphate). The solid was removed by filtration through Celite (ether wash). Concentration of the filtrate in vacuo afforded 14 as colorless needles.

Figure 5B:
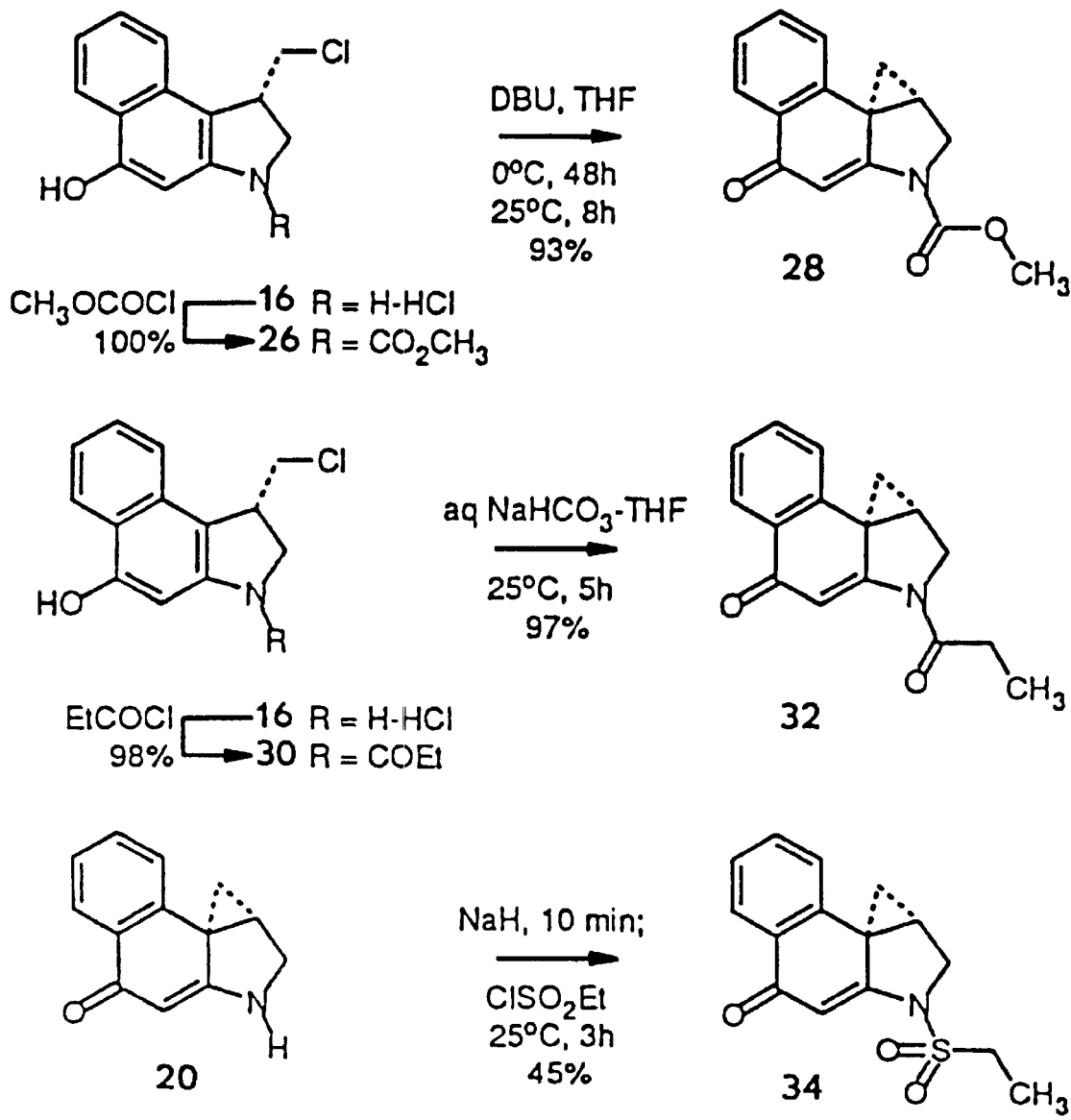
Figure 6:
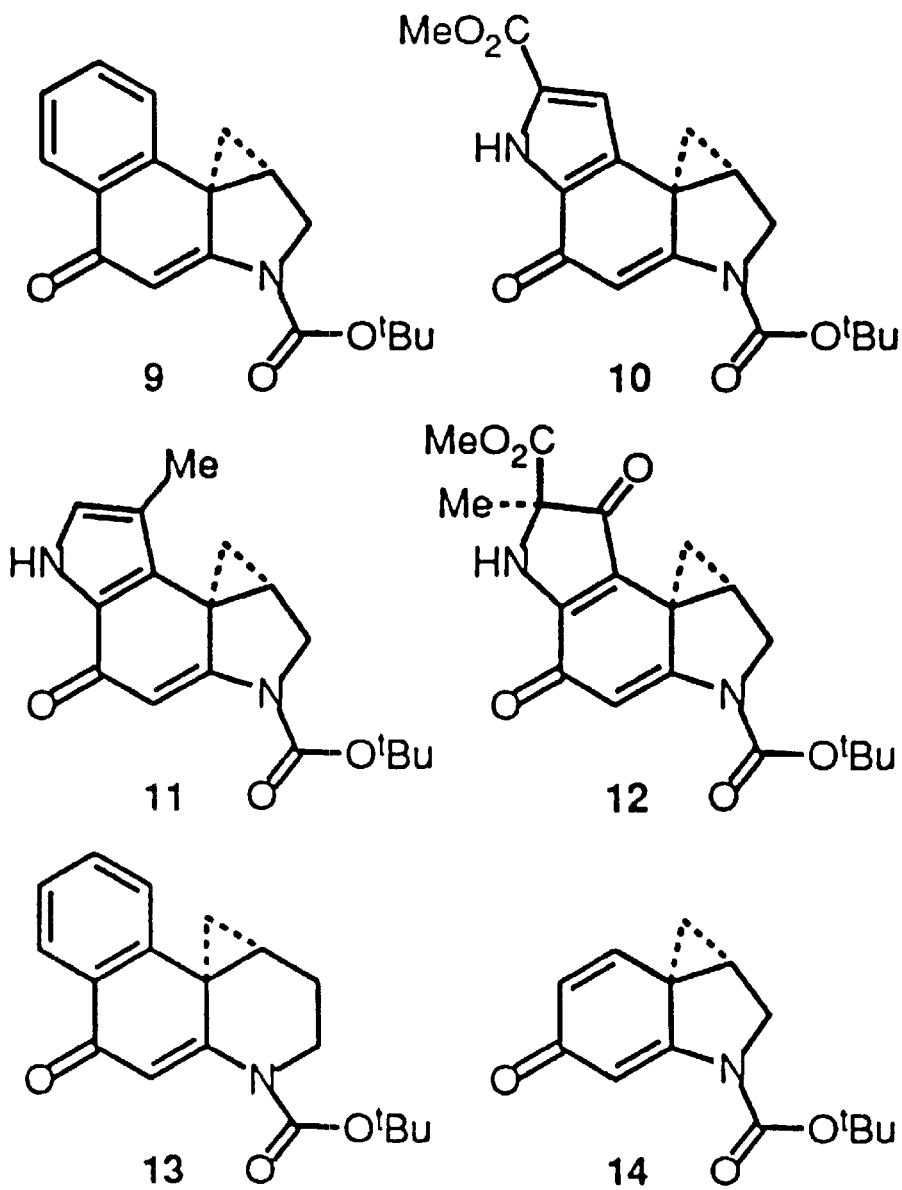
FIG. 6 illustrates the structures of compounds 9, 10, 11, 12, and 14 with the indicated rate constant k ($s^{-1}$, pH 3) of acid-catalyzed solvolysis, half life $t_{1/2}$ in solution and cytotoxic activity $IC_{50}$ (L1210 cells).

Preparation of Compound 16 (Illustrated in FIGS. 5A–5B)

Compound 14 (1.0 equiv.) was treated with anhydrous 3N hydrochloric acid in ethyl acetate (0.033 M) at 24° C. for 20 min. The solvent was removed in vacuo to afford crude, unstable 16 (95%–100%). The crude product was directly carried on without purification (for a related procedure see Boger et. al. *J. Org. Chem.* 1990, 23, 5831 experimental 5).

Preparation of Compound 18 (Illustrated in FIGS. 5A–5B)

A solution of 14 (1.0 equiv.) in 0.01 M of tetrahydrofuran-dimethylformamide (1:1) was cooled to 0° C. and treated with NaH (1.5 equiv). The reaction mixture was slowly warmed to 24° C. and stirred for 3.5 h. The mixture was placed on a flash chromatography column ($SiO_2$, 0.5×3 mm), and eluted with 5–10% $CH_3OH$—$CHCl_3$ (gradient elution) to afford 18 as a bright yellow solid.

Preparation of Compound 20 (Illustrated in FIGS. 5A–5B)

A solution of 16 (1.0 equiv.) in tetrahydrofuran (0.02 M) was treated with 0.02 M of 5% aqueous $NaHCO_3$ and the two-phase mixture was stirred at 24° C. for 5 h under $N_2$. The reaction mixture was extracted with Ethylacetate (3×). The organic layer was dried ($Na_2SO_4$) and concentrated. Flash chromatography afforded 20 as a pale yellow solid. As an alternative, one can obtain compound 20 from compound 18 in trifluoroacetic acid (0.1 equiv.) and methylene chloride (0.02 M) at 0° C. for 2 hours (for a related procedure see Boger et. al. *J. Org. Chem.* 1990, 23, 5831 experimental 5).

Preparation of 1-(Chloromethyl)-5-hydroxy-3-[(methylaminocarbonyl]-1,2-dihydro-3H-benz[e] indole (22) (Illustrated in FIGS. 5A–5B)

Phenol 14 (6.9 mg, 21 μmol) was treated with anhydrous 3M HCl-Ethylacetate at 24° C. for 30 min under Ar. The solvent was removed in vacuo to afford crude, unstable 16 (quantitative). A solution of 16 and $NaHCO_3$ (5.2 mg, 62 μmol, 3 equiv) in tetrahydrofuran (0.3 mL) was cooled to 0° C. and treated with $CH_3NCO$ (2.4 μL, 41 μmol, 2 equiv). The reaction mixture was kept at 0° C. for 1 h under Ar before the solvent was removed under a stream of $N_2$. Flash chromatography ($SiO_2$, 0.5×3 cm, 50–80% Ethylacetate-hexane gradient elution) afforded 22 (5.0 mg, 6.0 mg theoretical, 83%) as a pale greenish solid: $^1H$ NMR ($CD_3OD$, 400 MHz) 8.11 (d, 1H, J =8.4 Hz, C6-H), 7.68 (s, 1H, C4-H), 7.65 (d, 1H, J=8.4 Hz, C9-H), 7.44 (t, 1H, J=8.2 Hz, C8-H), 7,24 (t, 1H, J=8.3 Hz, C7-H), 4.06–4.14 (m, 3H, C2-$H_2$, C1-H), 3.92 (d, 1H, J=11.4 Hz, CHHCl), 3.51–3.53 (m, 1H, CHHCl), 2.83 (s, 3H, $CH_3$); IR (film)$_{max}$ 3816, 1624, 1585, 1522, 1384, 1339, 1250, 1121 $cm^{-1}$; FAB-HRMS (NBA) m/e 290.0818 ($M^+$+H, $C_{15}H_{15}ClN_2O_2$ requires 290.0822). Natural (1S)-22: $[\alpha]^5$ −4.5 (c 0.36, $CH_3OH$). Ent-(1R)-22: $[\alpha]^5$ +5.7 (c 0.11, $CH_3OH$).

Preparation of $N^2$-[(Methylamino)carbonyl]-1,2,9,9a-tetrahydro-cyclo-propa-[c]benz[e]-indol-4-one (24) (Illustrated in FIGS. 5A–5B)

A solution of 22 (3.0 mg, 10.3 μmol) in dimethylformamide (0.9 mL) was cooled to 0° C. and treated with 1,8-DIZABICYCLO[5.4.0]UNDEC-7-ENE (3.2 μL, 21 μmol, 2 equiv) and the mixture was stirred at 4° C. for 2 d. The solvent was removed in vacuo and flash chromatography ($SiO_2$, 0.5×3 cm, 0–10% $CH_3OH$-Ethylacetate gradient elution) afforded 24 (2.3 mg, 2.6 mg theoretical, 90%) as a pale yellow solid: $^1H$ NMR ($CD_3OD$, 400 MHz) 8.08 (d, 1H, J=8.0 Hz, C5-H), 7.55 (t, 1H, J=7.7 Hz, C7-H), 7.40 (t, 1H, J=8.0 Hz, C6-H), 7.08 (d, 1H, J=7.7 Hz, C8-H), 6.93 (s, 1H, C3-H), 4.05 (dd, 1H, J=10.0, 5.1 Hz, C1-H), 3.95 (d, 1H, J=10.0 Hz, C1-H), 3.08 (m, 1H, C9a-H), 2.79 (s, 3H, $CH_3$), 1.73 (dd, 1H, J=7.8, 4.2 Hz, C9-H), 1.48 (t, 1H, J=4.6 Hz, C9-H); IR (neat)$_{max}$ 3358, 2920, 1680, 1622, 1594, 1539, 1466, 1458, 1410, 1281 $cm^{-1}$; UV ($CH_3OH$)$_{max}$ 311 (15000), 257 (7300), 217 (17000), 200 (17000) nm; UV (tetrahydrofuran)$_{max}$ 304 (11000), 248 (7200), 216 (17000), 208 (15000) nm; FABHRMS (NBA) m/e 255.1140 ($M^+$+H, $C_{15}H_{14}N_2O_4$ requires 255.1134). Natural (+)-24: $[\alpha]^3$ +183 (c 0.08, $CH_3OH$). Ent-(−)-24: $[\alpha]^5$ −184 (c 0.13, $CH_3OH$).

Preparation of 1-(Chloromethyl)-5-hydroxy-3-(methoxycarbonyl)-1,2-dihydro-3H-benz[e]indole (26) (Illustrated in FIGS. 5A–5B).

A solution of freshly prepared, crude 16 (52 μmol) and $NaHCO_3$ (13.2 mg, 157 μmol, 3 equiv) in tetrahydrofuran (0.5 mL) was cooled to 0° C. and treated with $ClCO_2CH_3$ (8.1 μL, 104 μmol, 2 equiv). The reaction mixture was warmed to 25° C. and stirred for 1.5 h before it was concentrated in vacuo. Flash chromatography ($SiO_2$, 1×10 cm, 20–40% Ethylacetate-hexane gradient elution) afforded 26 (15 mg, 15 mg theoretical, 100%) as a white solid: $^1H$ NMR ($CDCl_3$, 400 MHz) 8.59 (br s, 1H, OH), 8.25 (d, 1H, J=8.1 Hz, C6-H), 7.94 (br s, 1H, C4-H), 7.62 (d, 1H, J=8.3 Hz, C9-H), 7.50 (t, 1H, J=8.1 Hz, C8-H), 7.35 (t, 1H, J=8.2 Hz, C7-H), 4.31 (d, 1H, J=11.4 Hz, C2-H), 4.12 (apparent t, 1H, J=9.3 Hz, C2-H), 3.90–3.99 (m, 5H, C1-H, CHHCl, $CO_2CH_3$), 3.40 (t, 1H, J=10.5 Hz, CHHCl); IR (film)$_{max}$ 3275, 2918, 1678, 1442, 1388, 1335 $cm^{-1}$; FABHRMS (NBA) m/e 291.0664 (M$^+$, C$_{15}$H$_{14}$ClNO$_4$ requires 291.0662). Natural-(1S)-26: [α]$^3$ −30.3 (c 0.11, CH$_3$OH). Ent-(1R)-26: [α]$^3$ +31.8 (c 0.24, CH$_3$OH).

Preparation of N$^2$-(Methoxycarbonyl)-1,2,9,9a-tetrahydro-cyclopropa-[c]benz[e]-indol-4-one (28) (Illustrated in FIGS. 5A–5B)

A solution of 26 (10.0 mg, 34 μmol) in tetrahydrofuran (3 mL) was cooled to 0° C. and treated with 1,8-DIZABICYCLO[5.4.0]UNDEC-7-ENE (10.5 μL, 68 μmol, 2 equiv). The reaction mixture was stirred at 4° C. for 41 h and then warmed to 24° C. and stirred for 10 h.[61] The reaction mixture was treated with saturated aqueous NH$_4$Cl (3 mL) and extracted with CH$_2$Cl$_2$ (3×2 mL). The combined organic layer was dried (Na$_2$SO$_4$) and concentrated. Flash chromatography (SiO$_2$, 1×10 cm, 10–50% Ethylacetate-hexane gradient elution) afforded 28 (8.1 mg, 8.7 mg theoretical, 87%) as a yellow solid: $^1$H NMR (CDCl$_3$, 400 MHz) 8.21 (d, 1H, J=7.8 Hz, C5-H), 7.48 (t, 1H, J=7.6 Hz, C7-H), 7.39 (t, 1H, J=7.8 Hz, C6-H), 6.87 (s, 1H, C3-H), 6.86 (d, 1H, J=7.6 Hz, C8-H), 3.86–4.08 (m, 2H, CH$_2$N), 3.86 (s, 3H, CH$_3$), 2.79 (m, 1H, C9a-H), 1.56–1.59 (m, 1H, C9-H), 1.39 (t, 1H, J=4.8 Hz, C9-H); IR (neat)$_{max}$ 3283, 2984, 1728, 1626, 1559, 1436, 1405, 1380, 1328, 1277, 1246, 1195, 1118, 1077, 1021, 764 cm$^{-1}$; UV (CH$_3$OH)$_{max}$ 307 (32000), 255 (24000), 216 (32000), 200 (33000) nm; UV (tetrahydrofuran)$_{max}$ 296 (33000), 253 (23000), 217 (38000), 203 (44000) nm; FABHRMS (NBA) m/e 256.0986 (M$^+$+H, C$_{15}$H$_{13}$NO$_3$ requires 256.0974). Natural (+)-28: [α]$^3$ +198 (c 0.48, CH$_3$OH). Ent-(−)-28: [α]$^5$ −196 (c 0.14, CH$_3$OH).

Preparation of 1-(Chloromethyl)-5-hydroxy-3-propionyl-1,2-dihydro-3H-benz[e]indole (30) (Illustrated in FIGS. 5A–5B)

A solution of freshly prepared, crude 16 (45 μmol) and NaHCO$_3$ (11.3 mg, 135 μmol, 3 equiv) in tetrahydrofuran (0.4 mL) was cooled to 0° C. and treated with ClCOEt (8 μL, 90 μmol, 2 equiv). The reaction mixture was warmed to 24° C. and stirred for 5 h under N$_2$. The solvent was removed under a stream of N$_2$. Flash chromatography (SiO$_2$, 1×10 cm, 10–40% Ethylacetate-hexane gradient elution) afforded 30 (12.8 mg, 13 mg theoretical, 98%) as a white solid: 1H NMR (CDCl$_3$, 400 MHz) 9.70 (br s, 1H, OH), 8.39 (s, 1H, C4-H), 8.32 (d, 1H, J=8.0 Hz, C6-H), 7.66 (d, 1H, J=8.3 Hz, C9-H), 7.52 (t, 1H, J=8.3 Hz, C8-H), 7.39 (t, 1H, J=8.3 Hz, C7-H), 4.32 (dd, 1H, J=2.0, 10.9 Hz, C2-H), 4.23 (d, 1H, J=10.8 Hz, C2-H), 4.04 (m, 1H, C1-H), 3.97 (dd, 1H, J=2.9, 11.3 Hz, CHHCl), 3.41 (t, 1H, J=10.8 Hz, CHHCl), 2.59–2.72 (m, 2H, CH$_2$CH$_3$), 1.39 (t, 3H, J=7.4 Hz, CH$_2$CH$_3$); IR (film)$_{max}$ 3170, 2918, 1628, 1582, 1427, 1389 cm$^{-1}$; FABHRMS (NBA) m/e 290.0953 (M$^+$+H, C$_{16}$H$_6$ClNO$_2$ requires 290.0953). Natural (1S)-30: [α]$^5$ −4 (c 0.08, tetrahydrofuran). Ent-(1R)-30: [α]$^5$ +59 (c 0.13 tetrahydrofuran).

Preparation of N$^2$-(Propionyl)-1,2,9,9a-tetrahydro-cyclopropa[c]benz[e]-indol4-one (32) (Illustrated in FIGS. 5A–5B)

A solution of 30 (5.0 mg, 17 μmol) in tetrahydrofuran (0.9 mL) was treated with 0.9 mL of 5% aqueous NaHCO$_3$ and the two-phase mixture was stirred at 24° C. for 5 h under N$_2$. The reaction mixture was extracted with Ethylacetate (3×3 mL). The organic layer was dried (Na$_2$SO$_4$) and concentrated. Flash chromatography (Florisil, 1×5 cm, 60% Ethylacetate-hexane) afforded 32 (4.2 mg, 4.3 mg theoretical, 97%) as a pale yellow solid: $^1$H NMR (CDCl$_3$, 400 MHz) 8.22 (d, 1H, J=7.8 Hz, C5-H), 7.51 (t, 1H, J=7.5 Hz, C7-H), 7.40 (t, 1H, J=7.9 Hz, C6-H), 6.89 (br s, 1H, C3-H), 6.88 (d, 1H, J=7.8 Hz, C8-H), 4.13–4.16 (m, 1H, C1-H), 4.03 (dd, 1H, J=10.6, 4.9 Hz, C1-H), 2.76–2.81 (m, 1H, C9a-H), 2.54–2.56 (m, 2H, CH$_2$CH$_3$), 1.67 (dd, 1H, J=7.6 Hz, 4.5 Hz, C9-H), 1.43 (t, 1H, J=4.8 Hz, C9-H), 1.22 (t, 3H, J=7.3 Hz, CH$_3$); IR (neat)$_{max}$ 2924, 1698, 1626, 1599, 1562, 1461, 1406, 1241 cm$^{-1}$; UV (CH$_3$OH)$_{max}$ 311 (16000), 258 (9100), 218 (14000), 201 (19000) nm; UV (tetrahydrofuran)$_{max}$ 301 (15000), 253 (9400), 219 (15000), 204 (15000) nm; FABHRMS (NBA) m/e 254.1173 (M$^+$+H, C$_{16}$H$_{15}$NO$_2$ requires 254.1181).Natural (+)-32: +193 (c 0.03, CH$_3$OH). Ent-(−)-32: −197 (c 0.12, CH$_3$OH).

Preparation of N$^2$-(Ethylsulfonyl)-1,2,9,9a-tetrahydro-cyclopropa[c]-benz[e]indol-4-one (34) (Illustrated in FIGS. 5A–5B)

NaH (1.5 mg, 60% oil dispersion, 38 μmol, 2.5 equiv) in a flame-dried flask was treated with (+)-CBI (20, 3.0 mg, 15.2 μmol) in tetrahydrofuran (0.8 mL) and the mixture was stirred for 10 min at 24° C. under N$_2$. A premixed solution of Triethylamine (7 μL, 50 μmol, 3.3 equiv) and ClSO$_2$Et (10 μL, 106 μmol, 7 equiv) in tetrahydrofuran (0.8 mL) was added and the reaction mixture was stirred at 24° C. for 3 h before being concentrated. Flash chromatography (SiO$_2$, 0.5×3 cm, 40–60% Ethylacetate-hexane gradient elution) afforded 34 (2.0 mg, 4.4 mg theoretical, 45%) as a pale yellow solid: $^1$H NMR (CDCl$_3$, 400 MHz) 8.19 (d, 1H, J=7.8 Hz, C5-H), 7.49 (t, 1H, J=8.3 Hz, C7-H), 7.39 (t, 1H, J=7.8 Hz, C6-H), 6.85 (d, 1H, J=7.8 Hz, C8-H), 6.46 (s, 1H, C3-H), 4.09 (m, 2H, CH$_2$N), 3.21–3.28 (m, 2H, CH$_2$CH$_3$), 2.83 (m, 1H, C9a-H), 1.69 (dd, 1H, J=7.8, 4.6 Hz, C9-H), 1.54 (t, 1H, partially obscured by H$_2$O, C9-H), 1.43 (t, 3H, J=7.4 Hz, CH$_3$); IR (neat)$_{max}$ 2923, 1618, 1559, 1354, 1149 cm$^{-1}$; UV (CH$_3$OH)$_{max}$ 301 (12000), 248 (11000), 214 (15000) nm; UV (tetrahydrofuran)$_{max}$ 293 (13000), 248 (14000), 216 (16000), 208 (14000) nm; FABHRMS (NBA-NaI) m/e 290.0850 (M$^+$+H, C$_{15}$H$_{15}$NO$_3$S requires 290.0851). Natural (+)-34: +73 (c 0.10, CHCl$_3$). Ent-(−)-34: −70 (c 0.12, CHCl$_3$).

Preparation of Solvolytic Reactivity of 24,28,32,34 (Illustrated in FIGS. 5A–5B)

The compounds 24,28,32,34 were dissolved in CH$_3$OH (1.5 mL). The CH$_3$OH solution was mixed with aqueous buffer (pH=3, 1.5 mL). The buffer contained 4:1:20 (v/v/v) 0.1 M citric acid, 0.2 M Na$_2$HPO$_4$, and H$_2$O, respectively. After mixing, the solvolysis solutions were stoppered and kept at 25° C. in the dark. The UV spectrum of the solutions was measured 3–4 times in the first two days and twice a day for 24 weeks for 24,28,32 and 3 months for 34. The UV monitoring was continued until no further change was detectable. The long-wavelength absorption at 316 nm (24, 28,32) or 306 nm (34) and short-wavelength absorption at 256 nm (24,28,34) or 248 nm (32) were monitored. The solvolysis rate constant and half-life were calculated from the data recorded at the short wavelength (256 nm for 24,28,32 and 248 nm for 34) from the least square treatment (r=0.995, 24; r=0.997, 28; r=0.985, 32; r=0.994, 34) of the slopes of plots of time versus 1−[(A−A$_{initial}$)/A$_{final}$−A$_{initial}$)].

Figure 10:
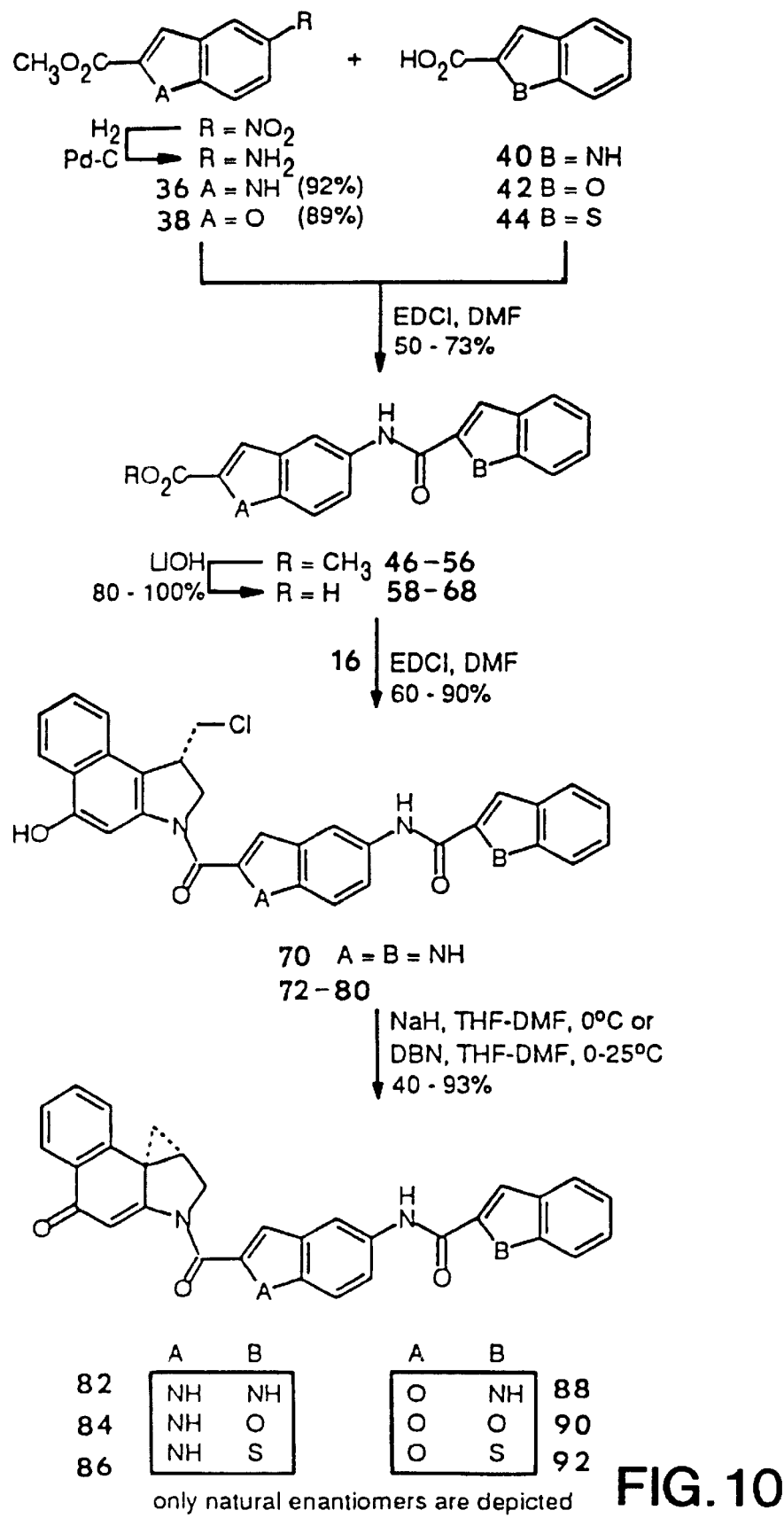
FIG. 10 illustrates the synthesis of compounds 82, 84, 86, 88, 90 and 92 with the indicated intermediates, substrates, and intermediate steps.
Figure 14:
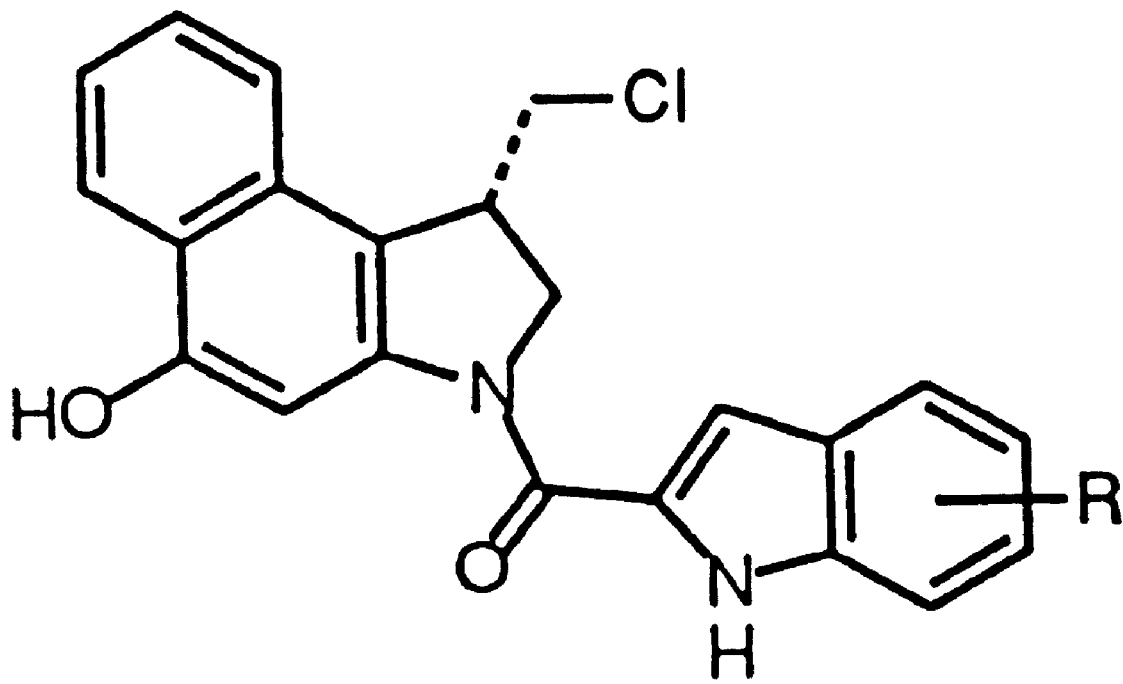
FIG. 14 illustrates the structures of CBI intermediate analogs 33, 66, 67 and 68.

Preparation of Methyl 5-Nitrobenzofuran-2-carboxylate (Illustrated in FIG. 10)

5-Nitrobenzofuran-2-carboxylic acid from Transworld chemicals inc. (500 mg, 2.4 mmol) in 20 mL of CH$_3$OH was treated with 5 drops of $H_2SO_4$. The reaction mixture was stirred at 24° C. for 24 h and warmed at 50° C. for 2 h. The mixture was cooled to 24° C., diluted with $H_2O$ (20 mL) and saturated aqueous $NaHCO_3$ (20 mL), and extracted with Ethylacetate (3×30 mL). The combined organic phase was dried ($Na_2SO_4$) and concentrated in vacuo. Flash chromatography ($SiO_2$, 2×20 cm, 40–60% Ethylacetate-hexane) afforded the methyl ester (469 mg, 534 mg theoretical, 88%) as a white solid: mp >230° C. (dec); $^1H$ NMR ($CDCl_3$, 400 MHz) 8.64 (d, 1H, J=2.3 Hz, C4-H), 8.37 (dd, 1H, J=2.3, 9.2 Hz, C6-H), 7.69 (d, 1H, J=9.1 Hz, C7-H), 7.64 (s, 1H, C3-H), 4.02 (s, 3H, $CH_3$); $^{13}C$ NMR ($CDCl_3$-$CD_3OD$, 100 MHz) 157.8 (C), 122.7 (CH), 120.9 (C), 119.4 (CH), 118.5 (C), 114.1 (CH), 112.7 (CH), 112.0 (C), 109.2 (C), 52.4 ($CH_3$); IR (film)$_{max}$ 3383, 3108, 1731, 1620, 1571, 1521, 1441, 1349, 1270, 1177, 827, 750 cm$^{-1}$; FABHRMS (NBA) m/e 222.0405 ($M^++H$, $C_{10}H_7NO_5$ requires 222.0402).

Preparation of Compound Methyl 5-Nitrobenzoimidazol-2-carboxylate (36) (Illustrated in FIG. 10)

Condensation of 3-nitrobenzaldehyde with methyl 2-azidoacetate (8 equiv, 6 equiv $NaOCH_3$, $CH_3OH$, −23 to 0° C., 6 h, 88%) followed by thermolysis of the resulting methyl 2-azidocinnamate (xylene, reflux, 4.5 h, 81%) provided a readily separable mixture (4:1) of methyl 5- and 7-nitroindole-2-carboxylate. For methyl 5-nitroindole-2-carboxylate: $^1H$ NMR (DIMETHYLSULFOXIDE-$d_6$, 400 MHz) 12.65 (br s, 1H, NH), 8.73 (d, 1H, J=2.3 Hz, C4-H), 8.14 (dd, 1H, J=2.0, 8.0 Hz, C6-H), 7.60 (d, 1H, J=8.0 Hz, C7-H), 7.45 (d, 1H, J=0.7 Hz, C3-H), 3.90 (s, 3H, $CO_2CH_3$); IR (film)$_{max}$ 3316, 1701, 1614, 1531, 1435, 1343, 1261, 1203, 992, 746 cm$^{-1}$. Catalytic hydrogenation of the 5-$NO_2$ group (1 atm $H_2$, 0.1 wt equiv 10% Pd—C, Ethylacetate, 25° C., 4–5 h) provided the corresponding amine. (36): 92%, mp 150–152° C. ($CH_2Cl_2$); $^1H$ NMR ($CDCl_3$, 400 MHz) 8.72 (br s, 1H, NH), 7.23 (d, 1H, J=8.6 Hz, C7-H), 7.03 (dd, 1H, J=1.0, 2.1 Hz, C3-H), 6.93 (dd, 1H, J=1.0, 2.0 Hz, C4-H), 6.81 (dd, 1H, J=2.0, 8.6 Hz, C6-H), 3.93 (s, 3H, $CO_2CH_3$), 3.57 (br s, 2H, NH); $^{13}C$ NMR ($CDCl_3$, 100 MHz) 160.0 (C), 150.3 (C), 145.6 (C), 143.0 (C), 127.7 (C), 117.7 (CH), 113.5 (CH), 112.6 (CH), 106.1 (CH), 52.2 ($CH_3$); IR (film)$_{max}$ 3320, 1691, 1628, 1531, 1437, 1376, 1337, 1232, 1034, 997, 766 cm$^{-1}$; FABHRMS (NBA) m/e 190.0746 ($M^+$H, $C_{10}H_{10}N_2O_2$ requires 190.0742).

Preparation of Methyl 5Aminobenzofuran-2-carboxylate (38) (Illustrated in FIG. 10)

A solution of methyl 5-nitrobenzofuran-2-carboxylate (469 mg, 2.12 mmol) in 50 mL of Ethylacetate was treated with 10% Pd—C (235 mg, 0.5 wt equiv), placed under 1 atm of $H_2$, and stirred at 25° C. (12 h). The catalyst was removed by filtration through Celite, and the solvent was removed in vacuo. Flash chromatography ($SiO_2$, 2×20 cm, 40–60% Ethylacetate-hexane) afforded 38 (360 mg, 404 mg theoretical, 89%) as a pale yellow solid: mp 109–111° C. ($CH_2Cl_2$, pale yellow fine needles); $^1H$ NMR ($CDCl_3$, 400 MHz) 7.36 (s, 1H, C3-H), 7.36 (d, 1H, J=8.1 Hz, C7-H), 6.89 (d, 1H, J=2.4 Hz, C4-H), 6.83 (dd, 1H, J=2.4, 8.9 Hz, C6-H), 3.94 (s, 3H, $CH_3$), 3.45 (br s, 2H, $NH_2$); IR (film)$_{max}$ 3359, 1725, 1562, 1488, 1434, 1331, 1301, 1222, 1158 cm$^{-1}$; FABHRMS (NBA) m/e 192.0663 ($M^++H$, $C_{10}H_9NO_3$ requires 192.0661).

General Procedure for the Preparation of 46,48,50,52,54,56 (Illustrated in FIG. 10)

Methyl 5-aminoindole-2-carboxylate (36), or methyl 5-aminobenzofuran-2-carboxylate (38), 1-(3-DIMETHYLAMINOPROPYL)-3-ETHYLCARBODIMIDE HYDROCHLORIDE (EDCI) (3 equiv) and indole-2-carboxylic acid (40) Aldrich company, benzofuran-2-carboxylic acid (42) Aldrich company or benzo[b]thiophene-2-carboxylic acid (44) Aldrich company (1 equiv) were stirred in dimethylformamide (0.04–0.06 M) at 24° C. under Ar for 12 h. The solvent was removed in vacuo, and the dry residue was mixed with $H_2O$ and stirred for 30 min. The precipitate was collected by centrifugation and washed with 1N aqueous HCl, saturated aqueous $NaHCO_3$, and $H_2O$. Drying the solid in vacuo afforded desired aqueous methyl esters 46,48,50,52,54,56 in typical yields of 50–73%.

Methyl 5-[((1H-Indol-2'-yl)carbonyl)amino]-1H-indole-2-carbox-ylate (46)

5 h, 61%; mp>270° C. (dec); $^1H$ NMR (DIMETHYLSULFOXDE-$d_6$, 400MHz) 11.92 (s, 1H, NH), 11.69 (s, 1H, NH), 10.16 (s, 1H, NH), 8.16 (d, 1H, J=1.6 Hz, C4-H), 7.67 (d, 1H, J=8.0 Hz, C4'-H), 7.60 (dd, 1H, J=2.0, 8.9 Hz, C6-H), 7.47 (d, 1H, J=8.3 Hz, C7'-H), 7.45 (d, 1H, J=9.0 Hz, C7-H), 7.41 (s, 1H, C3-H), 7.21 (t, 1H, J=8.2 Hz, C6'-H), 7.18 (s, 1H, C3'-H), 7.07 (t, 1H, J=7.1 Hz, C5'-H), 3.88 (s, 3H, $CH_3$); IR (neat)$_{max}$ 3277, 1700, 1652, 1553, 1535, 1310, 1247, 1225, 1022, 999, 742 cm$^{-1}$; FABHRMS (NBA-NaI) m/e 356.1004 ($M^+$ Na, $C_{19}H_{15}N_3O_3$ requires 356.1011).

Methyl 5-[((Benzofuro-2'-yl)carbonyl)amino]-1H-indole-2-carboxylate (48): 5 h, 73%; mp>230° C.; $^1H$ NMR (DIMETHYLSULFOXIDE-$d_6$, 400 MHz) 11.91 (br s, 1H, NH), 10.48 (br s, 1H, NH), 8.18 (d, 1H, J=1.8 Hz, C4-H), 7.83 (d, 1H, J=7.8 Hz, C4'-H), 7.76 (s, 1H, C3'-H), 7.72 (d, 1H, J=8.4 Hz, C7'-H), 7.61 (dd, 1H, J=1.9, 8.9 Hz, C6-H), 7.50 (t, 1H, J=8.4 Hz, C6'-H), 7.44 (d, 1H, J=8.8 Hz, C7-H), 7.37 (t, 1H, J=7.6 Hz, C5'-H), 7.18 (s, 1H, C3-H), 3.88 (s, 3H, $CH_3$); IR (film)$_{max}$ 3333, 1695, 1658, 1591, 1535, 1442, 1303, 1255, 746 cm$^{-1}$; FABHRMS (NBA) m/e 335.1036 (($M^++H$, $C_{19}H_{14}N_2O_4$ requires 335.1032).

Methyl 5-[((Benzo[b]thieno-2'-yl)carbonyl)amino]-1H-indole-2-carboxylate (50): 7 h, 62%; mp>230° C.; $^1H$ NMR (DIMETHYLSULFOXIDE-$d_6$, 400 MHz) 11.93 (br s, 1H, NH), 10.47 (br s, 1H, NH), 8.35 (s, 1H, C3'-H), 8.13 (d, 1H, J=1.9 Hz, C4-H), 8.05 (d, 1H, J=7.0 Hz, C7'-H), 7.99 (d, 1H, J=6.7 Hz, C4'-H), 7.57 (dd, 1H, J=2.0, 8.9 Hz, C6-H), 7.44–7.50 (m, 2H, C6'-H, C5'-H), 7.44 (d, 1H, J=9.0 Hz, C7-H), 7.17 (s, 1H, C3-H), 3.87 (s, 3H, $CH_3$); $^{13}C$ NMR (DIMETHYLSULFOXIDE-$d_6$, 100MHz) 161.7, 160.1, 140.5, 140.4, 139.2, 134.6, 131.6, 127.7, 126.6, 126.4, 125.3 (two CH), 125.0, 122.8, 119.9, 113.2, 112.6, 107.9, 51.8; IR (film)$_{max}$ 3336, 1694, 1633, 1532, 1455, 1336, 1309, 1257, 1232 cm$^{-1}$; FABHRMS (NBA) m/e 351.0810 ($M^++H$, $C_{19}H_{14}N_2O_3S$ requires 351.0803).

Methyl 5-[((1H-Indol-2'-yl)carbonyl)amino]benzofuran-2-carboxylate (52): 8 h, 52%; mp>230° C.; $^1H$ NMR (DIMETHYLSULFOXIDE-$d_6$, 400 MHz) 11.75 (s, 1H, NH), 10.36 (s, 1H, NH), 8.34 (d, 1H, J=2.1 Hz, C4-H), 7.84 (dd, 1H, J=2.1, 9.0 Hz, C6-H), 7.83 (s, 1H, C3-H), 7.73 (d, 1H, J=9.0 Hz, C7-H), 7.68 (d, 1H, J=8.0 Hz, C4'-H), 7.47 (d, 1H, J=8.3 Hz, C7'-H), 7.43 (s, 1H, C3'-H), 7.22 (t, 1H, J=7.1 Hz, C6'-H), 7.07 (t, 1H, J=7.1 Hz, C5'-H), 3.89 (s, 3H, $CH_3$); IR (film)$_{max}$ 3346, 1712, 1643, 1577, 1543, 1308, 1289, 1234, 745 cm$^{-1}$; FABHRMS (NBA) m/e 335.1040 ($M^++H$, $C_{19}H_{14}N_2O_4$ requires 335.1032).

Methyl 5-[((Benzofuro-2'-yl)carbonyl)amino]benzofuran-2-carboxylate (54): 12 h, 62%; mp>230° C.; $^1H$ NMR ($CDCl_3$, 400 MHz) 8.44 (br s, 1H, NH), 8.28

(apparent t, 1H, J=1.3 Hz, C4-H), 7.69 (d, 1H, J=7.7 Hz, C4'-H), 7.60 (d, 1H, J=0.8 Hz, C3-H or C3'-H), 7.54–7.56 (apparent d, 3H, J=8.4 Hz), 7.51 (s, 1H, C3-H or C3'-H), 7.45 (t, 1H, J=7.2 Hz, C6'-H), 7.31 (t, 1H, J=7.9 Hz, C5'-H), 3.97 (s, 3H, $CH_3$); $^{13}C$ NMR ($CDCl_3$, 100MHz) 159.8 (C), 156.7 (C), 154.8 (C), 152.8 (C), 148.3 (C), 146.3 (C), 133.3 (C), 127.6 (C), 127.4 (C), 127.3 (CH), 124.0 (CH), 122.9 (CH), 121.0 (CH), 114.1 (CH), 114.0 (CH), 112.7 (CH), 111.8 (CH), 111.7 (CH), 52.5 ($CH_3$); IR (film)$_{max}$ 3382, 1729, 1663, 1562, 1541, 1475, 1431, 1291, 1204, 1151, 1103 $cm^{-1}$; FABHRMS (NBA) m/e 336.0878 ($M^+$+H, $C_{19}H_{13}NO_5$ requires 336.0872).

Methyl 5-[((Benzo[b]thieno-2'-yl)carbonyl)amino]benzofuran-2-carboxylate (56): 8h, 50%; mp>230° C.; $^1H$ NMR (DIMETHYLSULFOXIDE-$d_6$, 400 MHz) 10.67 (s, 1H, NH), 8.38 (s, 1H, C3'-H), 8.31 (d, 1H, J=2.0 Hz, C4-H), 8.06 (dd, 1H, J=1.7, 6.9 Hz, C7'-H), 8.00 (dd, 1H, J=1.8, 6.9 Hz, C4'-H), 7.83 (s, 1H, C3-H), 7.80 (dd, 1H, J=2.1, 9.0 Hz, C6-H), 7.74 (d, 1H, J=9.0 Hz, C7-H), 7.50 (dt, 1H, J=1.7, 7.1 Hz, C6'-H), 7.47 (dt, J=2.0, 7.1 Hz, C5'-H), 3.89 (s, 3H, $CH_3$); IR (film)$_{max}$ 3287, 1728, 1657, 1546, 1473, 1436, 1296, 1216, 1154 $cm^{-1}$; FABHRMS (NBA) m/e 352.0650 ($M^+$+H, $C_{19}H_{13}NO_4S$, requires 352.0644).

General Procedure for the Preparation of 58,60,62,64,66,68 (Illustrated in FIG. 10).

A solution of one the methyl esters 46,48,50,52,54 or 56 prepared as above in tetrahydrofuran-$CH_3OH$—$H_2O$ (3:1:1) was treated with 4 equiv of LiOH $H_2O$. The reaction mixture was stirred at 24° C. for 4–6 h. The solvent was removed and the dry residue was mixed with $H_2O$, acidified with 1N aqueous HCl to pH 1. The precipitate was collected by centrifuigation and washed with $H_2O$ (2×). Drying the solid in vacuo afforded the desired acid 58,60,62,64,66,68 with yields 80–100%.

5-[((1H-Indol-2'-yl)carbonyl)amino]-1H-indole-2-carboxylic Acid (58): 3 h, 89%; mp>270° C. (dec); $^1H$ NMR (DIMETHYLSULFOXIDE-$d_6$, 400 MHz) 11.82(s, 1H, NH), 11.23 (br s, 1H, NH), 10.14 (s, 1H, NH), 7.99 (s, 1H, C4-H), 7.66 (d, 1H, J=7.6 Hz, C4'-H), 7.48 (d, 1H, J=8.0 Hz, C6-H), 7.41 (s, 1H, C3-H), 7.39–7.41 (m, 2H, C7'-H and C7-H), 7.20 (t, 1H, J=7.6 Hz, C6'-H), 7.06 (t, 1H, J=7.2 Hz, C5'-H), 6.69 (br s, 1H, C3'-H); IR (film)$_{max}$ 3413, 3354, 3315, 1665, 1596, 1532, 1463, 1444, 1409, 1306, 1222, 1159, 1080 $cm^{-1}$; FABHRMS (NBA) m/e 320.1041 ($M^+$+H, $C_{18}H_{13}N_3O_3$ requires 320.1035).

5-[((Benzofuro-2'-yl)carbonyl)amino]-1H-indole-2-carboxylic Acid (60): 5 h, 77%; mp>230° C.; $^1H$ NMR (DIMETHYLSULFOXIDE-$d_6$, 400 MHz) 11.62 (br s, 1H, NH), 10.43 (s, 1H, NH), 8.12 (s, 1H, C4-H), 7.83 (d, 1H, J=7.6 Hz, C4'-H), 7.75 (s, 1H, C3'-H), 7.73 (d, 1H, J=8.4 Hz, C7'-H), 7.55 (d, 1H, J=9.2 Hz, C6-H), 7.50 (t, 1H, J=8.4 Hz, C6'-H), 7.40 (d, 1H, J=8.8 Hz, C7-H), 7.37 (t, 1H, J=7.2 Hz, C5'-H), 7.00 (br s, 1H, C3-H); IR (film)$_{max}$ 3297, 1661, 1594, 1537, 1299, 1258, 1229, 743 $cm^{-1}$; FABHRMS (NBA) m/e 321.0880 ($M^+$+H, $C_{18}H_{12}N_2O_4$ requires 321.0875).

5-[((Benzo [b]thieno-2'-yl)carbonyl)amino]-1H-indole-2-carboxylic Acid (62): 3 h; 80%; mp>230° C.; $^1H$ NMR (DIMETHYLSULFOXIDE-$d_6$, 400 MHz) 11.63 (s, 1H, NH), 10.46 (s, 1H, NH), 8.36 (s, 1H, C3'-H), 8.08 (s, 1H, C4-H), 8.04 (d, 1H, J=6.8 Hz, C7'-H), 7.99 (d, 1H, J=6.6 Hz, C4'-H), 7.52 (d, 1H, J=8.9 Hz, C6-H), 7.44–7.48 (m, 2H, C6'-H, C5'-H), 7.41 (d, 1H, J=8.8 Hz, C7-H), 7.00 (s, 1H, C3-H); $^{13}C$ NMR (DIMETHYLSULFOXIDE-$d_6$, 100 MHz) 163.1, 160.0, 140.6, 140.4, 139.3, 134.2, 131.1, 126.9, 126.3, 125.3, 125.3 (CH and C), 125.0, 122.9, 118.9, 113.1, 112.4, 106.4; IR (film)$_{max}$ 3429, 3375, 1648, 1542, 1431, 1305, 1249, 739 $cm^{-1}$; FABHRMS (NBA) m/e 337.0654 ($M^+$+H, $C_{18}H_{12}N_2O_3S$ requires 337.0647).

5-[((1H-Indol-2'-yl)carbonyl)amino]benzofuran-2-carboxylic Acid (64): 4 h, 80%; mp>230° C.; $^1H$ NMR (DIMETHYLSULFOXIDE-$d_6$, 400 MHz) 13.54 (br s, 1H, $CO_2H$), 11.74 (s, 1H, NH), 10.34 (s, 1H, NH), 8.30 (d, 1H, J=1.8 Hz, C4H), 7.81 (dd, 1H, J=1.9, 9.0 Hz, C6-H), 7.72 (s, 1H, C3-H), 7.70 (d, 1H, J=7.6 Hz, C7-H), 7.68 (d, 1H, J=8.6 Hz, C4'-H), 7.47 (d, 1H, J=8.3 Hz, C7'-H), 7.43 (s, 1H, C3'-H), 7.22 (t, 1H, J=8.0 Hz, C6'-H), 7.06 (t, 1H, J=7.6 Hz, C5'-H); IR (film)$_{max}$ 3285, 1703, 1649, 1547, 1475, 1420, 1312, 1231, 1195, 1159, 744 $cm^{-1}$; FABHRMS (NBA) m/e 321.0870 ($M^+$+H, $C_{18}H_{12}N_2O_4$ requires 321.0875).

5-[((Benzofuro-2'-yl)carbonyl)amino]benzofuran-2-carboxylic Acid (66): 12 h, 100%; mp>230° C.; $^1H$ NMR (DIMETHYLSULFOXIDE-$d_6$, 400 MHz) 13.50 (br s, 1H, $CO_2H$), 10.61 (s, 1H, NH), 8.22 (d, 1H, J=1.7 Hz, C4-H), 7.83 (d, 1H, J=7.7 Hz, C4'-H), 7.78 (d, 1H, J=0.8 Hz, C3'-H), 7.73 (dd, 1H, J=0.7, 8.4 Hz, C7'-H), 7.72 (dd, 1H, J=2.1, 9.0 Hz, C6-H), 7.61 (d, 1H, J=8.9 Hz, C7-H), 7.50 (t, 1H, J=8.4 Hz, C6'-H), 7.37 (t, 1H, J=7.9 Hz, C5'-H), 7.35 (br s, 1H, C3-H); IR (film)$_{max}$ 3362, 1709, 1659, 1564, 1473, 1438, 1292, 1226, 1152, 790 $cm^{-1}$; FABHRMS (NBA) m/e 322.0720 ($M^+$+H, $C_{18}H_1NO_5$ requires 322.0715).

5-[((Benzo[b]thieno-2'-yl)carbonyl)amino]benzofuran-2-carboxylic Acid (68): 12 h, 82%; mp>230° C.; $^1H$ NMR (DIMETHYLSULFOXIDE-$d_6$, 400 MHz) 13.61 (br s, 1H, $CO_2H$), 10.67 (s, 1H, NH), 8.40 (s, 1H, C3'-H), 8.30 (d, 1H, J=1.9 Hz, C4-H), 8.09 (dd, 1H, J=1.7, 6.8 Hz, C7'-H), 8.05 (dd, 1H, J=1.8, 6.2 Hz, C4'-H), 7.79 (dd, 1H, J=2.0, 9.1 Hz, C6-H), 7.73 (d, 1H, J=9.0 Hz, C7-H), 7.70 (br s, 1H, C3-H), 7.53 (dt, 1H, J=1.6, 7.1 Hz, C6'-H), 7.50 (dt, 1H, J=1.5, 7.1 Hz, C5'-H); IR (film)$_{max}$ 3395, 1697, 1653, 1551, 1479, 1296, 1273, 1231, 1155, 1024, 991, 762 $cm^{-1}$; FABHRMS (NBA) m/e 338.0480 ($M^+$+H, $C_{18}H_{11}NO_4S$ requires 338.0487).

Preparation of compounds 70,72,74,76,78,80 (Illustrated in FIG. 10)—General Procedure for the Coupling of 16 with 58,60,62,64,66,68. Phenol 14 was treated with anhydrous 3M HCl-Ethylacetate at 24° C. for 30 min. The solvent was removed in vacuo to afford crude unstable 16 (quantitative). A solution of 16, one of the carboxylic acids 58,60,62,64, 66,68 (1 equiv), and 1-(3-DIMETHYLAMINOPROPYL)-3-ETHYLCARBODIIMIDE HYDROCHLORIDE (EDCI) (2–3 equiv) in dimethylformamide (0.04–0.06 M) was stirred at 24° C. under $N_2$ for 8–12 h. The reaction mixture was concentrated under vacuum and suspended in $H_2O$ and the precipitate was collected by centrifugation, and washed with $H_2O$ (2×). Flash chromatagraphy ($SiO_2$, 40–60% tetrahydrofuran-hexane) afforded 70 and 72,74,76,78,80 in yields of 60–90%.

3-[(5'-(((1H-Indol-2''-yl)carbonyl)amino)-1H-indol-2'-yl)carbonyl]-1-(chloromethyl)-5-hydroxy-1,2-dihydro-3H-benz[e]indole (70): 8.5 h, 73%; mp>255° C. (dec); $^1H$ NMR (dimethylformamide-$d_7$, 400 MHz) 11.76 (s, 1H, NH), 11.69 (s, 1H, NH), 10.58 (s, 1H, NH), 10.28 (s, 1H, OH), 8.40 (d, 1H, J=1.7 Hz, C4'-H), 8.25 (d, 1H, J=8.4 Hz, C6-H), 8.10 (br s, 1H, C4-H), 7.96 (d, 1H, J=8.3 Hz, C4''-H), 7.73 (d, 1H, J=2.0, 8.9 Hz, C6'-H), 7.70 (d, 1H, J=8.0 Hz, C9-H), 7.61 (d, 1H, J=8.2 Hz, C7''-H), 7.59 (d, 1H, J=8.8 Hz, C7'-H), 7.57 (t, 1H, J=8.1 Hz, C8-H), 7.53 (s, 1H, C3'-H), 7.41 (t, 1H, J=8.0 Hz, C7-H), 7.30 (s, 1H, C3''-H), 7.26 (t, 1H, J=8.0 Hz, C6''-H), 7.10 (t, 1H, J=7.9 Hz, C5''-H), 4.90 (apparent t, 1H, J=10.6 Hz, C2-H), 4.76 (dd, 1H, J=1.8, 10.9 Hz, C2-H), 4.30–4.34 (m, 1H, C1-H), 4.13 (dd, 1H, J=3.1, 11.0 Hz, CHHCl), 3.96 (dd, 1H, J=7.8, 11.0 Hz, CHHCl); IR (film)$_{max}$ 3258, 2923, 1659, 1624, 1578, 1512, 1411, 1395, 1233, 745 cm$^{-1}$; FABHRMS (NBA) m/e 535.1526 (M$^+$+H, C$_{31}$H$_{23}$ClN$_4$O$_3$ requires 535.1537). Natural (1S)-70: [ ]$^5$ +70 (c 0.17, dimethylformamide). Ent-(1R)-70: [α]$^5$ −70 (c 0.17, dimethylformamide).

3-[(5'-(((Benzofuro-2"-yl)carbonyl)amino)-1H-indol-2'-yl)carbonyl]-1-(chloromethyl)-5-hydroxy-1,2-dihydro-3H-benz[e]indole (72): 14 h, 60%; mp>230° C.; $^1$H NMR (DIMETHYLSULFOXIDE-d$_6$, 400 MHz) 11.73 (s, 1H, NH), 10.59 (s, 1H, NH), 10.56 (s, 1H, OH), 8.44 (d, 1H, J=1.0 Hz, C4'-H), 8;24 (d, 1H, J=8.4 Hz, C6-H), 8.10 (br s, 1H, C4-H), 7.94 (d, 1H, J=8.3 Hz, C4"-H), 7.85 (d, 1H, J=7.8 Hz, C7"-H), 7.80 (dd, 1H, J=2.0, 8.8 Hz, C6'-H), 7.78 (s, 1H, C3"-H), 7.68 (d, 1H, J=8.4 Hz, C9-H), 7.61 (d, 1H, J=8.6 Hz, C7'-H), 7.56 (t, 1H, J=7.0 Hz, C6"-H), 7.52 (t, 1H, J=8.4 Hz, C8-H), 7.40 (t, 1H, J=7.8 Hz, C5"-H or C7-H), 7.39 (t, 1H, J=7.7 Hz, C5"-H or C7-H), 7.32 (s, 1H, C3'-H), 4.90 (apparent t, 1H, J=10.8 Hz, C2-H), 4.75 (dd, 1H, J=2.0, 10.8 Hz, C2-H), 4.32–4.34 (m, 1H, C1-H), 4.13 (dd, 1H, J=3.2, 11.2 Hz, CHHCl), 3.96 (dd, 1H, J=7.6, 11.2 Hz, CHHCl); $^{13}$C NMR (tetrahydrofuran-d$_8$, 100 MHz) 161.1 (C), 156.9 (C), 155.9 (C), 155.7 (C), 151.2 (C), 143.6 (C), 134.8 (C), 132.8 (C), 132.6 (C), 131.3 (C), 129.0 (two C), 128.0 (CH), 127.4 (CH), 124.5 (CH), 124.4 (CH), 123.7 (C), 123.6 (CH), 123.4 (CH), 123.1 (CH), 119.9 (CH), 116.0 (C), 114.1 (CH), 112.5 (CH), 112.4 (CH), 110.9 (CH), 106.7 (CH), 101.4 (CH), 56.1 (CH), 47.2 (CH$_2$), 43.9 (CH$_2$); IR (film)$_{max}$ 3272, 2954, 1610, 1585, 1513, 1408, 1253, 1135, 741 cm$^{-1}$; FABHRMS (NBA) m/e 536.1390 (M$^+$+H, C$_{31}$H$_{22}$ClN$_3$O$_4$ requires 536.1377). Natural (1S)-72: [α]$^3$ +56 (c 0.23, tetrahydrofuran).

3-[(5'-(((Benzo[b]thieno-2"-yl)carbonyl)amino)-1H-indol-2'-yl)carbonyl]-1-(chloromethyl)-5-hydroxy-1,2-dihydro-3H-benz[e]indole (74): 11 h, 68%; mp>230° C.; $^1$H NMR (DIMETHYLSULFOXIDE-d$_6$, 400 MHz) 11.80 (s, 1H, NH), 10.52 (s, 1H, NH), 10.48 (s, 1H, OH), 8.40 (s, 1H, C3"-H), 8.20 (d, 1H, J=1.6 Hz, C4'-H), 8.15 (d, 1H, J=8.2 Hz, C6-H), 8.08 (d, 1H, J=6.9 Hz, C7"-H), 8.03 (d, 1H, J=6.7 Hz, C4"-H), 8.01 (br s, 1H, C4-H), 7.88 (d, 1H, J=8.4 Hz, C9-H), 7.60 (dd, 1H, J=1.9, 8.9 Hz, C6'-H), 7.48–7.57 (m, 4H, C5"-H, C8-H, C7'-H), 7.39 (t, 1H, J=8.1 Hz, C7-H), 7.25 (s, 1H, C3'-H), 4.85 (apparent t, 1H, J=10.8 Hz, C2-H), 4.60 (dd, 1H, J=1.8, 11.0 Hz, C2-H), 4.24–4.28 (m, 1H, C1-H), 4.06 (dd, 1H, J=3.1, 11.1 Hz, CRHCl), 3.91 (dd, 1H, J=7.3, 11.1 Hz, CHHCl); IR (film)$_{max}$ 3286, 1655, 1628, 1587, 1518, 1409, 1262, 1239 cm$^{-1}$; FABHRMS (NBA) m/e 552.1152 (M$^+$+H, C$_{31}$H$_{22}$ClN$_3$O$_3$S requires 552.1149). Natural (1S)-74: [α]$^3$ +111 (c 0.15, dimethylformamide).

3-[(5'-(((1H-Indol-2"-yl)carbonyl)amino)benzofuro-2'-yl)carbonyl]-1-(chloromethyl)-5hydroxy-1,2-dihydro-3H-benz[e]indole (76): 13 h, 80%; mp>230° C.; $^1$H NMR (DIMETHYLSULFOXIDE-d$_6$, 400 MHz) 11.78 (s, 1H, NH), 10.51 (s, 1H, NH), 10.38 (s, 1H, OH), 8.35 (d, 1H, J=2.0 Hz, C4'-H), 8.12 (d, 1H, J=8.3 Hz, C6-H), 7.92 (br s, 1H, C4-H), 7.86 (d, 1H, J=8.8 Hz, C9-H), 7.84 (dd, 1H, J=2.1, 9.0 Hz, C6'-H), 7.80 (s, 1H, C3'-H), 7.76 (d, 1H, J=9.0 Hz, C7'-H), 7.69 (d, 1H, J=8.0 Hz, C4"-H), 7.53 (t, 1H, J=8.2 Hz, C8-H), 7.48 (d, 1H, J=8.4 Hz, C7"-H), 7.45 (s, 1H, C3"-H), 7.38 (t, 1H, J=8.0 Hz, C7-H), 7.23 (t, 1H, J=8.0 Hz, C6"-H), 7.07 (t, 1H, J=7.7 Hz, C5"-H), 4.79 (apparent t, 1H, J=9.8 Hz, C2-H), 4.58 (d, 1H, J=9.9 Hz, C2-H), 4.24 (m, 1H, C1-H), 4.01 (dd, 1H, J=3.1, 11.1 Hz CHHCl), 3.89 (dd, 1H, J=7.4, 11.1 Hz, CHHCl); IR (film)$_{max}$ 3274, 2928, 1655, 1621, 1579, 1546, 1414, 1390, 1329, 1240 cm$^{-1}$; FABHRMS (NBA) n/e 536.1360 (M$^+$+, C$_{31}$H$_{22}$ClN$_3$O$_4$ requires 536.1377). Natural (1S-76: [α]$^3$ +26 (c 0.36, dimethylformamide).

3-[(5'-(((Benzofuro-2"-yl)carbonyl)amino)benzofuro-2'-yl)carbonyl]1-(chloromethyl)-5-hydroxy-1,2-diliydro-3H-benz[e]indole (78): 11 h, 88%; mp>230° C.; $^1$H NMR (DIMETHYLSULFOXIDE-d$_6$ 400 MHz) 10.72 (s, 1H, NH), 10.48 (s, 1H, OH), 8.38 (d, 1H, J=2.0 Hz, C4'-H), 8.14 (d, 1H, J=8.3 Hz, C6H), 7.71–7.95 (m, 7H), 7.54 (t, 1H, J=7.2 Hz, C8-H), 7.52 (t, 1H, J=7.4 Hz, C6"-H), 7.39 (t, 2H, J=7.9 Hz, C7-H and C5"-H), 4.79 (apparent t, 1H, J=10.6 Hz, C2-H), 4.59 (d, 1H, J=9.8 Hz, C2-H), 4.25 (m, 1H, C1-H), 4.02 (dd, 1H, J=3.0, 11.1 Hz, CHHCl), 3.90 (dd, J=7.4, 11.1 Hz, CHHCl); IR (film)$_{max}$ 3267, 2923, 1664, 1581, .1554, 1410, 1390, 1328, 1256 cm$^{-1}$; FABHRMS (NBA) m/e 537.1210 (M$^+$+, C$_{31}$H$_{21}$ClN$_2$O$_5$ requires 537.1217). Natural (1S)-78: [α]$^3$ +26 (c 0.28, dimethylformamide).

3-[(5'-(((benzo[b]thieno-2"-yl)carbonyl)amino)benzofuro-2'-yl)carbonyl]-1-(chloromethyl)-5-hydroxy-1,2-dihydro-3H-benz[e]indole (80): 18 h, 68%; mp>230° C.; $^1$H NMR (DIMETHYLSULFOXIDE-d$_6$, 400 MHz) 10.69 (s, 1H, NH), 10.52 (s, 1H, OH), 8.40 (s, 1H, C3"-H), 8.32 (d, 1H, J=1.9 Hz, C4'-H), 8.13 (d, 1H, J=8.3 Hz, C6-H), 8.07 (d, 1H, J=8.7 Hz, C7"-H), 8.03 (d, 1H, J=6.2 Hz, C4"-H), 7.94 (br s, 1H, C4-H), 7.86 (d, 1H, J=8.3 Hz, C9-H), 7.82 (dd, 1H, J=2.0, 9.0 Hz, C6'-H),7.80 (s, 1H, C3'-H), 7.77 (d, 1H, J=9.0 Hz, C7'-H), 7.45–7.55 (m, 3H, C8-H, C6"-H, C5"-H), 7.38 (t, 1H, J=7.9 Hz, C7-H), 4.79 (apparent t, J=10.0 Hz, C2-H), 4.59 (d, 1H, J=10.0 Hz, C2-H), 4.22–4.26 (m, 1H, C1-H), 4.02 (dd, 1H, J=3.0, 11.1 Hz, CHHCl), 3.88 (dd, 1H, J=7.4, 11.0 Hz, CHHCl); IR (film)$_{max}$ 3259, 2923, 1659, 1630, 1583, 1549, 1413, 1392, 1336, 1244, 1211 cm$^{-1}$; FABHRMS (NBA) m/e 553.0985 (M$^+$+H, C$_{31}$H$_{21}$ClN$_2$O$_4$S requires 553.0989). Natural (1S)-80: [α]$^3$ +30 (c 0.33, dimethylformamide).

Preparation of compounds 82 and 84,86,88,90,92 (Illustrated in FIG. 10)—General Procedures for the Spirocyclization and Preparation of 82 and 84,86,88,90,92. Method A: A suspension of NaH (60% oil dispersion, 2 equiv) in tetrahydrofuran at 0° C. under Ar was treated with a solution of 70, 72,74,76,78,80 prepared above in tetrahydrofuran-dimethylformamide (1:1, ca. 0.015 M reaction concentration). The reaction mixture was stirred at 0° C. for 30 min–1 h. The solvent was removed in vacuo and the solid residue was washed with H$_2$O and dried in vacuo. Flash chromatography (SiO$_2$, 50–70% tetrahydrofuran-hexane) afforded 82, 84,86,88,90,92 in 50–93% yield.

Method B: A solution of compounds 70, 72,74,76,78,80 in tetrahydrofuran-dimethylformamide (2:1, ca. 0.015 M) was cooled to 0° C. and treated with 1,5-diazabicyclo [4.3.0] non-5-ene (DBN, 2 equiv). The reaction mixture then was allowed to warm to 24° C. and stirred for 2–4 h. The solvent was removed in vacuo, and flash chromatography (SiO$_2$, 50–70% tetrahydrofuran-hexane) afforded 82, 84,86,88,90, 92 with 40–75% yield.

Method C: A sample of 70 (1.6 mg, 0.0030 mmol) in tetrahydrofliran (0.20 mL) was treated with the phosphazene base P$_4$-t-Bu (3.3 μL, 1 M solution in hexane, 1.1 equiv) at −78° C. The mixture was stirred under Ar at −78° C. for 40 min, at 0° C. for 6 h, and at 25° C. for 2 h. The crude mixture was purified directly by chromatography (SiO$_2$, 60% tetrahydrofuran-hexane) to provide 82 (1.4 mg, 1.5 mg theoretical, 93%) as a yellow solid.

N$^2$-[5'-(((1H-Indol-2"-yl)carbonyl)amino)-1H-indol-2'-yl)carbonyl]-1,2,9,9a-tetrahydrocyclopropa[c]benz[e]indol-4-one (82, CBI-indole$_2$): Method A, 93%; method B, 75%; method C, 93%; mp>240° C.; $^1$H NMR (DIMETHYLSULFOXIDE-d$_6$, 300 MHz) 11.86 (br s, 1H, NH), 11.73 (br s, 1H, NH), 10.19 (s, 1H, NH), 8.24 (d, 1H, J=2.6 Hz, C4'-H), 8.02 (d, 1H, J=8.0 Hz, C5-H), 7.67 (d, 1H, J=7.8 Hz, C4"-H), 7.63 (m, 2H, C6-H and C7-H), 7.47 (m, 4H), 7.29 (s, 1H, C3'-H or C3"-H), 7.25 (m, 2H, C8-H and C6''-H), 7.07 (t, 1H, J=7.3 Hz, C5''-H), 6.98 (s, 1H, C3-H), 4.65 (dd, 1H, J=4.9, 10.2 Hz, C1-H), 4.53 (apparent d, 1H, J=10.2 Hz, C1-H), 3.20 (m, 1H, obscured by H$_2$O, C9a-H), 1.77 (dd, 1H, J=4.2, 7.4 Hz, C9-H), 1.73 (t, 1H, J=4.2 Hz, C9-H); IR (KBr)$_{max}$ 3432, 1648, 1522, 1384, 1266, 1126, 744 cm$^{-1}$UV (dimethylformamide)$_{max}$ 316(=45000), 274 nm (25000); FABHRMS (NBA) m/e 499.1792 (M$^+$+H, C$_{31}$H$_{22}$N$_4$O$_3$ requires 499.1770). Natural (+)-82: [α]$^3$+114 (c 0.03, dimethylformamide), [α]$^5$ +81 (c 0.12, tetrahydrofuran). Ent (−)-82: [α]$^5$ −120 (c 0.1, dimethylformamide), [α]$^5$ −81 (c 0.12, tetrahydrofuran).

N$^2$-[(5'-(((Benzofuro-2''-yl)carbonyl)amino)-1H-indol-2'-yl)carbonyl]-1,2,9,9a-tetrahydrocyclopropa[c]benz[e]indol-4-one (84): Method A, 60%; method B, 49%; mp>230° C.; $^1$H NMR (DIMETHYLSULFOXDE-d$_6$, 400 MHz) 11.89 (s, 1H, NH), 10.51 (s, 1H, NH), 8.25 (d, 1H, J=1.4 Hz, C4'-H), 8.04 (d, 1H, J=7.8 Hz, C5-H), 7.85 (d, 1H, J=7.7 Hz, C4''-H), 7.79 (s, 1H, C3''-H), 7.75(d, 1H, J=8.3 Hz, C7''-H), 7.66 (dd, 1H, J=1.8, 8.9 Hz, C6'-H), 7.63 (t, 1H, J=7.4 Hz, C7''-H), 7.53 (t, 1H, J=8.3 Hz, C6''-H), 7.50 (d, 1H, J=8.7 Hz, C7'-H), 7.46 (t, 1H, J=7.2 Hz, C6-H), 7.39 (t, 1H, J=7.4 Hz, C5''-H), 7.31 (s, 1H, C3'-H), 7.28 (d, 1H, J=7.8 Hz, C8-H), 7.00 (s, 1H, C3-H), 4.66 (dd, 1H, J=5.0, 10.3 Hz, C1-H), 4.53 (d, 1H, J=10.3 Hz, C1-H), 3.28–3.32 (m, 1H, C9a-H), 1.79 (dd, 1H, J=4.1, 7.6 Hz, C9-H), 1.73 (apparent t, 1H, J=4.4 Hz, C9-H); $^{13}$C NMR (tetrahydrofuran-d$_8$, 100 MHz) 185.2 (C), 162.3 (C), 160.7 (C), 157.0 (C), 155.9 (C), 151.1 (C), 141.4 (C), 135.2 (C), 134.1 (C), 132.8 (C), 132.2 (CH), 131.6 (C), 128.7 (C), 127.5 (CH), 127.1 (CH), 126.9 (CH), 124.5 (CH), 123.4 (CH), 122.5 (CH), 120.5 (CH), 114.1 (CH), 112.7 (CH), 112.4 (two CH), 110.9 (CH), 108.4 (C), 107.9 (CH), 55.3 (CH$_2$), 33.2 (C), 29.9 (CH) 28.5 (CH$_2$): IR (film)$_{max}$ 3299,1654, 1595, 1517, 1388, 1262, 1127, 744 cm$^{-1}$; FABHRMS (NBA) m/e 500.1610 (M$^+$+H, C$_{31}$H$_{21}$N$_3$O$_4$ requires 500.1610). Natural (+)-84: [α]$^3$ +91 (c 0.13, tetrahydrofuran).

N$^2$-[(5'-(((Benzo [b]thieno-2''-yl)carbonyl)amino)-1H-indol-2'-yl)carbonyl]-1,2,9,9a-tetrahydrocyclopropa[c]benz [e]indol-4-one (86): Method A, 50%; method B, 46%; mp>230° C.; $^1$H NMR (DIMETHYLSULFOXIDE-d$_6$, 400 MHz) 11.88 (s, 1H, NH), 10.50 (s, 1H, NH), 8.36 (s, 1H, C3''-H), 8.18 (s, 1H, C4'-H), 8.06 (d, 1H, J=6.7 Hz, C7''-H), 8.01 (d, 2H, J=7.2 Hz, C4''-H, C5-H), 7.61 (t, 1H, J=8.2 Hz, C7-H), 7.59 (d, 1H, J=8.9 Hz, C6'-H), 7.42–7.51 (m, 4H, C6-H, C6''-H, C5''-H, C7'-H), 7.28 (s, 1H, C3'-H), 7.26 (d, 1H, J=7.8 Hz, C8-H), 6.98 (s, 1H, C3-H), 4.65 (dd, 1H, J=5.0, 10.3 Hz, C1-H), 4.51 (d, 1H, J=10.2 Hz, C1-H), 3.28 (m, 1H, partially obscured by H$_2$O, C9a-H), 1.76 (dd, 1H, J=4.2, 7.6 Hz, C9-H), 1.71 (apparent t, 1H, J=4.8 Hz, C9-H); IR (film)$_{max}$ 3321, 1652, 1593, 1554, 1516, 1386, 1256, 1121 cm$^{-1}$; FABHRMS (NBA) m/e 516.1391 (M$^+$+H, C$_{31}$H$_{21}$N$_3$O$_3$S requires 516.1382). Natural (+)-86: +73 (c 0.05, dimethylformamide).

N$^2$-[(5'-(((1H-Indol-2''-yl)carbonyl)amino)benzofuran-2'-yl)carbonyl]-1,2,9,9a-tetrahydrocyclopropa[c]benz[e]indol-4-one (88): Method A, 63%; method B, 45%; mp>230° C.; $^1$H NMR (DIMETHYLSULFOXIDE-d$_6$, 400 MHz) 11.77 (s, 1H, NH), 10.38 (s, 1H, NH), 8.35 (d, 1H, J=2.0 Hz, C4'-H), 8.01 (d, 1H, J=7.8 Hz, C5-H), 7.87 (s, H, C3'-H), 7.85 (dd, H, J=2.1, 9.0 Hz, C6'-H), 7.75 (d, 1H, J=9.0 Hz, C7'-H), 7.68 (d, 1H, J=8.1 Hz, C4''-H), 7.61 (t, 1H, J=7.8 hz, C7-H), 7.47 (d, 1H, J=8.8 Hz, C7''-H), 7.44 (s, 1H, C3''-H), 7.44 (t, 1H, J=8.0 Hz, C6-H), 7.25 (d, 1H, J=7.0 Hz, C8-H), 7.22 (t, 1H, J=8.2 Hz, C6''-H), 7.07 (t, 1H, J=7.0 Hz, C5''-H), 6.91 (s, 1H, C3-H), 4.53–4.59 (m, 2H, C1-H$_2$), 3.27–328 (m, 1H, partially obscured by H$_2$O, C9a-H), 1.72–1.78 (m, 2H, C9-H$_2$); IR (film)$_{max}$ 3330, 1660, 1548, 1382, 1300, 1242, 1035 cm$^{-1}$; FABHRMS (NBA) m/e 500.1600 (M$^+$+H, C$_{31}$H$_{21}$N$_3$O$_4$ requires 500.1610). Natural (+)-88: +176 (c 0.09, dimethylformamide).

N$^2$-[(5'-(((Benzofuro-2''-yl)carbonyl)amino)benzofuro-2'-yl)carbonyl]-1,2,9,9a-tetrahydrocyclopropa[c]benz[e] indol-4-one (90): Method A, 93%; method B, 49%; mp>230° C.; $^1$H NMR (DIMETHYLSULFOXIDE-d$_6$, 400 MHz) 10.74 (s, 1H, NH), 8.39 (d, 1H, J=2.0 Hz, C4'-H), 8.04 (d, 1H, J=7.9 Hz, C5-H), 7.90 (s, 1H, C3'-H), 7.89 (dd, 1H, J=2.2, 9.0 Hz, C6'-H), 7.87 (d, 1H, J=7.8 Hz, C4''-H), 7.82 (s, 1H, C3''-H), 7.78 (d, 1H, J=9.0 Hz, C7'-H), 7.77 (d, 1H, J=8.4 Hz, C7''-H), 7.64 (t, 1H, J=7.5 Hz, C7-H), 7.54 (t, 1H, J=8.3 Hz, C6''-H), 7.47 (t, 1H, J=7.6 Hz, C6-H), 7.41 (t, 1H, J=8.0 Hz, C5''-H), 7.27 (d, 1H, J=7.6 Hz, C8-H), 6.94 (s, 1H, C3-H), 4.62 (dd, 1H, J=4.7, 10.5 Hz, C1-H), 4.57 (d, 1H, J=10.4 Hz, C1-H), 3.30 (m, 1H, partially obscured by H$_2$O, C9a-H), 1.80 (dd, 1H, J=4.1, 7.7 Hz, C9-H), 1.76 (t, 1H, J=4.6 Hz, C9-H); IR (film)$_{max}$ 3369, 2921, 1660, 1600, 1549, 1378, 1295, 1244, 1050 cm$^{-1}$; FABHRMS (NBA) m/e 501.1470 (M$^+$+H, C$_{31}$H$_{20}$N$_2$O$_5$ requires 501.1450). Natural (+)-90: [α]$^3$ +90 (c 0.10, dimethylformamide).

N$^2$-[(5'-(((Benzo[b]thieno-2''-yl)carbonyl)amino) benzofuro-2'-yl)carbonyl]-1,2,9,9a-tetrahydrocyclopropa [c]benz[e]indol-4-one (92): Method B, 50%; mp>230° C.; $^1$H NMR (DIMETHYLSULFOXIDE-d$_6$, 400 MHz) 10.72 (s, 1H, NH), 8.41 (s, 1H, C3''-H), 8.34 (d, 1H, J=2.2 Hz, C4'-H), 8.09 (d, 1H, J=7.0 Hz, C5-H), 8.05 (d, 1H, J=7.0 Hz, C7''-H), 8.04 (d, 1H, J=6.2 Hz, C4''-H), 7.90 (s, 1H, C3'-H), 7.85 (dd, 1H, J=2.0, 8.9 Hz, C6'-H), 7.78 (d, 1H, J=9.0 Hz, C7'-H), 7.64 (t, 1H, J=6.2 Hz, C7-H), 7.45–7.55 (m, 3H, C6-H, C6''-H, C5''-H), 7.27 (d, 1H, J=8.0 Hz, C8-H), 6.94 (s, 1H, C3-H), 4.58–4.62 (m, 2H, C1-H$_2$), 3.27–3.28 (m, 1H, obscured by H$_2$O, C9a-H), 1.76–1.80 (m, 2H, C9-H$_2$); IR (film)$_{max}$ 2920, 2851, 1661, 1599, 1555, 1466, 1381, 1297, 1243 cm$^{-1}$; FABHRMS (NBA) m/e 517.1233 (M$^+$+H, C$_{31}$H$_{20}$N$_2$O$_4$S requires 517.1222). Natural (+)-92: [α]$^3$ +69 (c 0.04, dimethylformamide).

Figure 16:
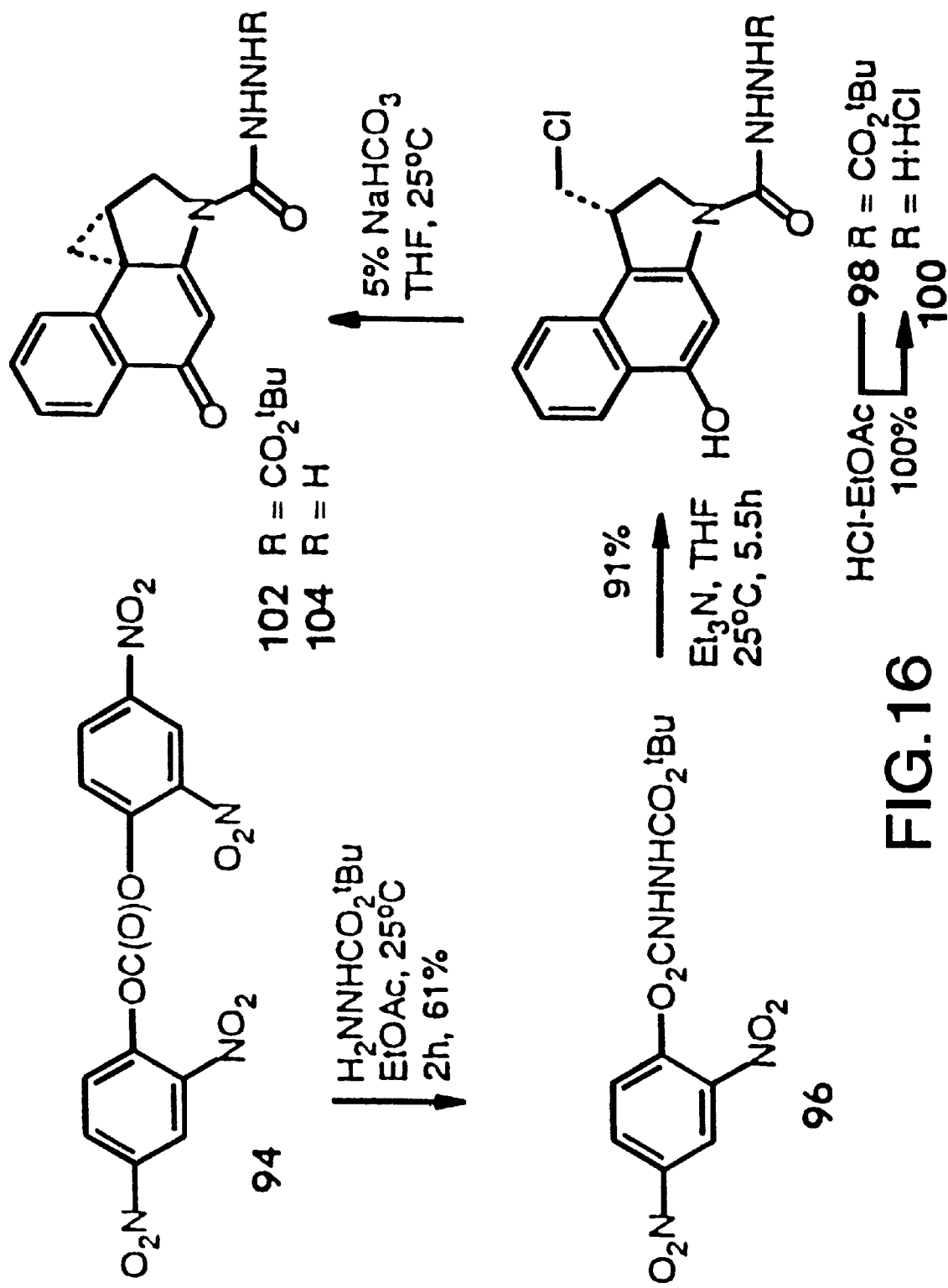
FIG. 16 illustrates the synthesis of compounds 102 and 104 with the indicated intermediates, substrates, and intermediate steps.

Preparation of 2,4-DinitrophenylN$^1$-[N$^2$-(tert-Butyloxycarbonyl)-hydrazino]-carboxylate (96)
(Illustrated in FIG. 16)

A suspension of bis(2,4-dinitrophenyl)carbonate (94, 394 mg, 1.0 mmol) as prepared by Gray et. al. *Tetrahedron*, 1977,33, 739, in 1.5 mL of Ethylacetate at 24° C. under N$_2$ was treated with a solution of tert-butylcarbazate from Aldrich company (132 mg, 1.0 mmol) in Ethylacetate (6 mL), and the reaction mixture was stirred for 2 h (24° C.). The reaction mixture was filtered through a glass filter. The filtrate was concentrated to 2 mL below 24° C. in vacuo and mixed with hexane (10 mL). The resulting precipitate was collected by filtration to afford 96 (271 mg, 72% pure as a mixture with 2,4-dinitrophenol) and a second crop of crystals was obtained from the mother liquor to afford pure 96 (12 mg) as colorless flakes: mp 105–107° C. (hexane, colorless flakes); $^1$H NMR (CDCl$_3$ 200 MHz) 8.93 (d, 1H, J=2.7 Hz, C3-H), 8.51 (dd, 1H, J=2.7, 9.0 Hz, C5-H), 7.62 (d, 1H, J=9.0 Hz, C6-H), 7.05 (br s, 1H, NH), 6.43 (br s, 1H, NH), 1.48 (s, 9H, C(CH$_3$)$_3$); IR (KBr)$_{max}$ 3414, 3268, 3112, 2978, 1754, 1738, 1612, 1538, 1484, 1394, 1364, 1240, 1166, 1070, 1024, 918, 858, 834, 752, 728, 642 cm$^{-1}$.

Preparation of 3-[N$^1$-[N$^2$-(tert-Butyloxycarbonyl) hydrazino]carbonyl]-1-chloromethyl-5-hydroxy-1,2-dihydro-3H-benz[e]indole (98) (Illustrated in FIG. 16). Phenol 14 (6.0 mg, 18 µmol) was treated with anhydrous 3N HCl-Ethylacetate (0.5 mL) at 24° C. for 20 min. the solvent was removed in vacuo to afford crude, unstable 16 quantitatively. A solution of 16 in tetrahydrofuran (0.4 mL) at 24°

C. under Ar was treated sequentially with 96 (11 mg, 72% pure, 23.4 μmol, 1.3 equi,) and Triethylamine (2.5 μL, 18 μmol, 1 equiv), and the reaction mixture was stirred for 5.5 h (24° C.). Flash chromatography (1.5×15 cm $SiO_2$, 66% Ethylacetate-hexane) afforded 98 (6.4 mg, 7.0 mg theoretical, 91%) as a white solid: mp 221° C.; $^1H$ NMR ($CDCl_3$-dimethylformamide-$d_7$, 200 MHz) 9.82 (s, 1H, OH), 8.25 (d, 1H, J=8 Hz, C6-H), 7.82 (s, 1H, C4-H), 7.64 (d, 1H, J=2 Hz, NH), 7.58 (d, 1H, J=8 Hz, C9-H), 7.46 (ddd, 1H, J=1.4, 7, 8 Hz, C8-H), 7.30 (ddd, 1H, J=1.4, 7, 8 Hz, C7-H), 6.86 (br s, 1H, NH, 4.24 (dd, 1H, J=3, 10 Hz, C2-H), 4.17 (t, 1, J=10 Hz, C2-H), 3.98 (m 1H, C1-H), 3.92 (dd, 1H, J=3, 11 Hz, CHHCl), 3.37 (t, 1H, J=11 Hz, CHHCl), 1.50 (s, 9H, $C(CH_3)_3$); IR $(KBr)_{max}$ 3408, 2926, 1718, 1654, 1584, 1522, 1476, 1394, 1246, 1160, 862, 758 cm$^{-1}$; UV (tetrahydrofuran)$_{max}$ 318 (=9500), 308 (8200), 260 (31000), 254 nm (32000); FABHRMS (DTT-DTE) m/e 392.1364 ($M^+$+H, $C_{19}H_{22}ClN_3O_4$ requires 392.1377).

Preparation of 1-(Chloromethyl)-3-(hydrazino)carbonyl-5hydroxy-1,2-dihydro-3H-benz[e]indole hydrochloride (100) (Illustrated in FIG. 16). A sample of 98 (1.0 mg, 2.6 μmol) was treated with anhydrous 3N HCl-Ethylacetate (1 mL) at 24° C. for 30 min. The solvent was removed in vacuo to afford 100 (0.9 mg, 0.87 mg theoretical, 100%) as a white solid: mp 225° C. (dec); $^1H$ NMR ($CDCl_3$-DIMETHYLSULFOXIDE-$d_6$, 300 MHz) 10.00 (bs s, $N^+H_3$), 9.96 (s, 1H, OH), 9.77 (s, 1H CONH), 8.18 (d, 1H, J=8.3 Hz, C6-H), 7.78 (s, 1H, C4-H), 7.63 (d, 1H, J=8.3 Hz, C9-H), 7.48 (t, 1H, J=7.4 Hz, C8-H), 7.30 (t, 1H, J=7.5 Hz, C7-H), 4.26 (m, 2H, C2-H), 4.07 (m, 1H C1-H), 3.93 (dd, 1H, J=2, 11 Hz, CHHCl), 3.51 (t, 1H, J=10.2 Hz, CHHCl); IR $(KBr)_{max}$ 3400 (br), 3200 (br), 2926, 1670, 1632, 1584, 1520, 1478, 1420, 1394, 1352, 1242, 1154, 1126, 1074, 1024, 756 cm$^{-1}$; UV (dimethylformamide)$_{max}$ 322 (=9300), 310 (sh, 7900), 270 nm (23000); FABHRMS (DTT-DTE) m/e 292.0867 ($M^+$+H, $C_{14}H_{14}ClN_3O_2$ requires 292.0853).

Preparation of compounds 102 and 104 (Illustrated in FIG. 16). A solution of 98 or 100 (1.0 equiv) in tetrahydrofuran (0.02 molar) was treated with 0.02 molar of 5% aqueous $NaHCO_3$ and the two-phase mixture was stirred at 24° C. for 5 h under $N_2$. The reaction mixture was extracted with Ethylacetate (3x). The organic layer was dried ($Na_2SO_4$) and concentrated. Flash chromatography affords 102 and 104 as a pale yellow solid.

Figure 17:
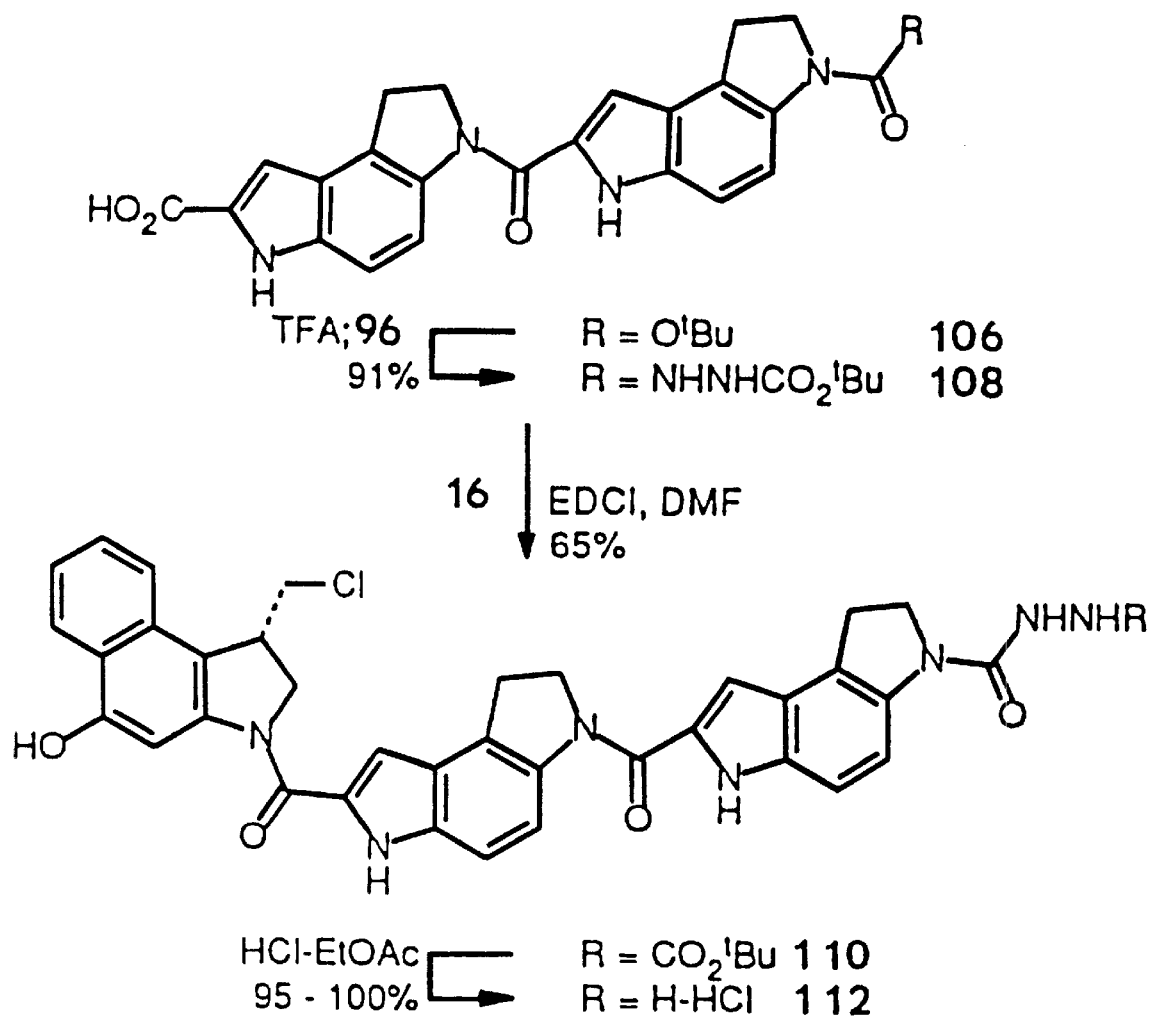
FIG. 17 illustrates the synthesis of compound 112 with the indicated intermediates, substrates, and intermediate steps.
Figure 19A:
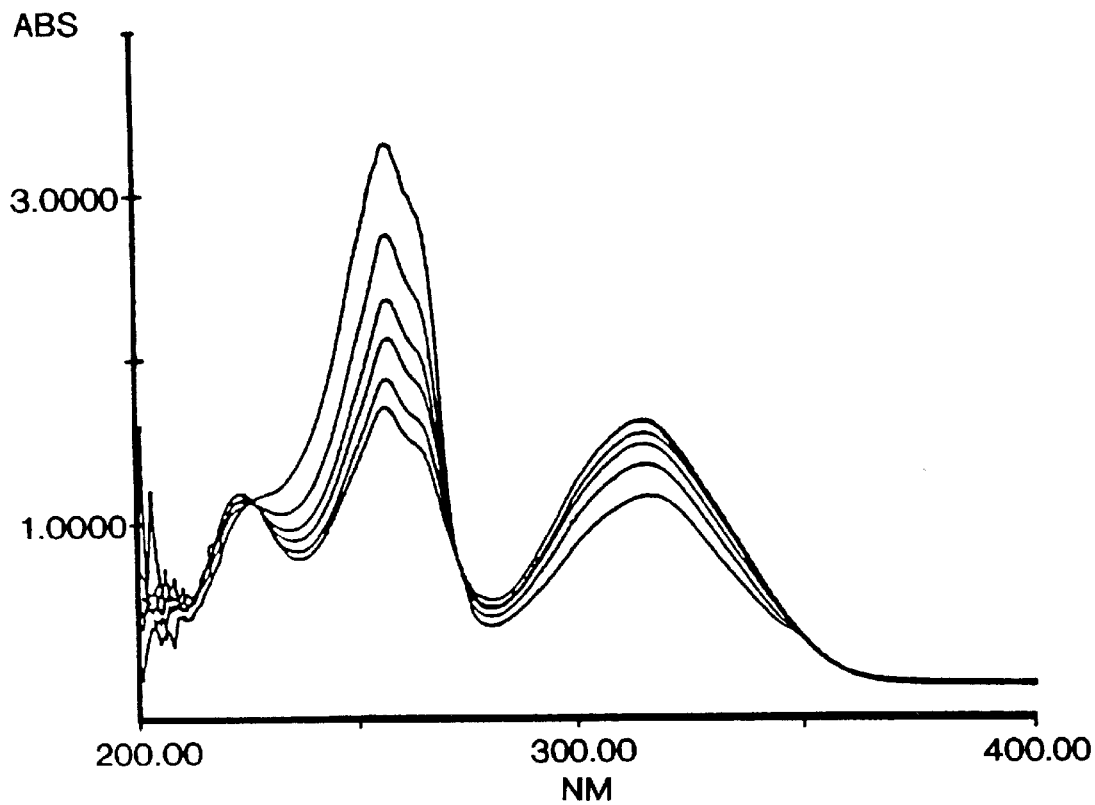
FIGS. 19A–19B illustrate the solvolysis of 23. Top: UV-visible spectra of 23 in 50% $CH_3OH$-aqueous buffer (pH 3) recorded at various time intervals (0, 21, 57, 84, 160, 371 h). Bottom: Plot of the disappearance of 23, $1-[(A-A_i)/(A_f-A_i)]$ versus time from which the first order solvolysis rate constant was derived.
Figure 19B:
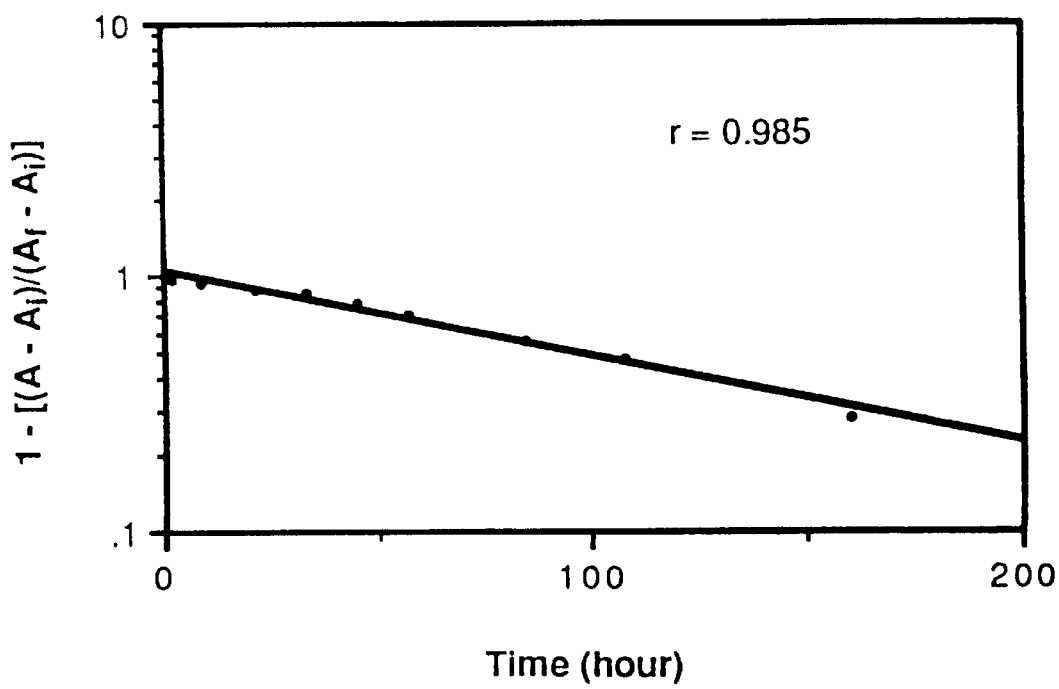
Figure 20A:
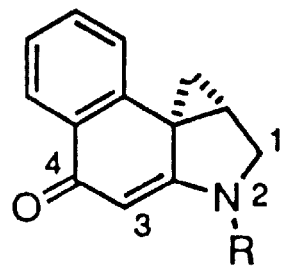
FIGS. 20A–20D illustrate the results of studies acid-catalyzed solvolysis studies of 21–24 conducted at pH 3 ($CH_3OH-H_2O$) were followed spectrophotometrically by UV with the disappearance of the characteristic long-wavelength absorption band of the CBI chromophore and with the appearance of a short-wavelength absorption band attributable to the seco-N-BOC-CBI derivative.
Figure 20B:
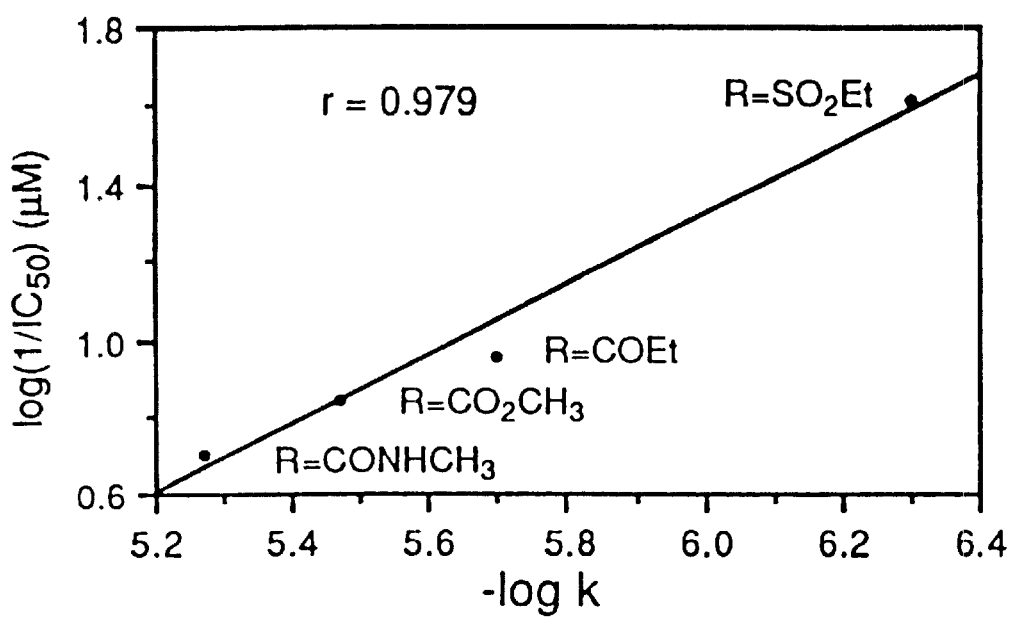
Figure 20C:
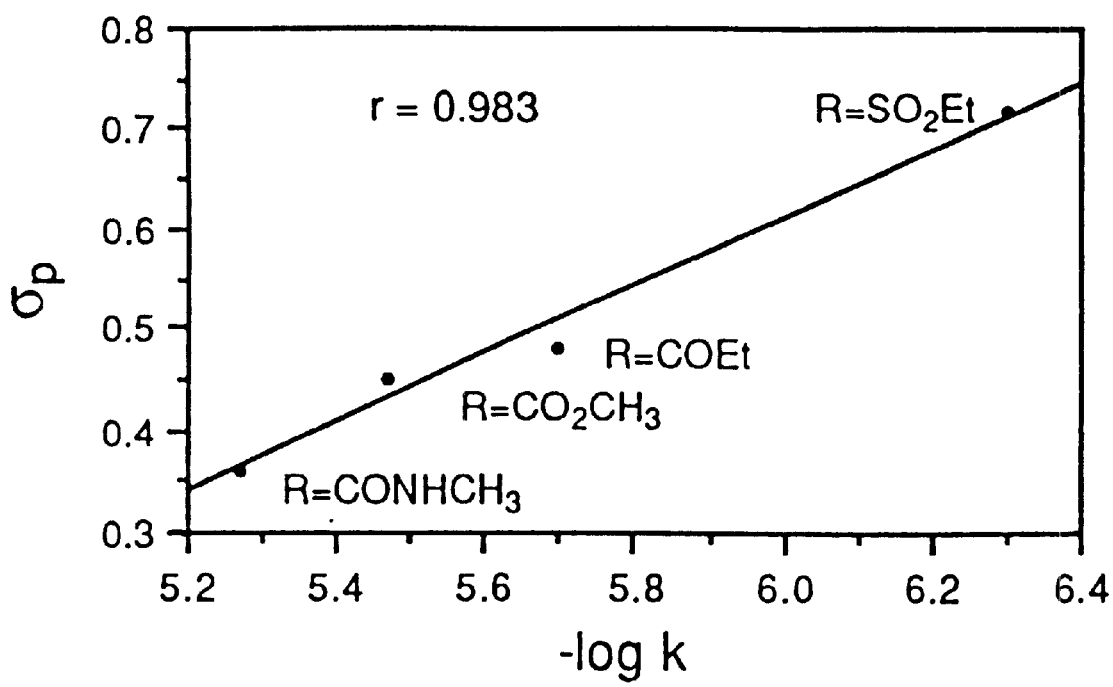
Figure 20D:
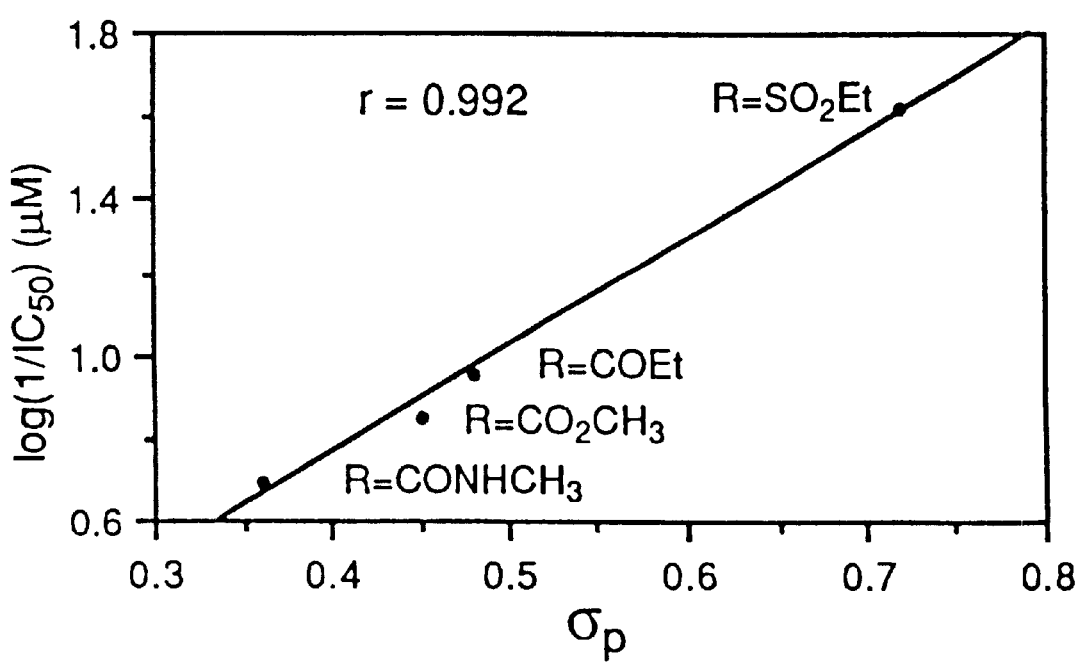

Preparation of $N^1$-[$N_2$-(tert-Butyloxycarbonyl)hydrazino] carbonyl-$CDPI_2$ (108) (Illustrated in FIG. 17). N-BOC-$CDPI_2$ (106, 6.2 mg, 12.8 μmol) as previously described in Boger et. al J. Org. Chem. 1987, 52, 1521, was treated with $CF_3CO_2H$ (0.5 mL) at 24° C. for 1 h. The $CF_3CO_2H$ was removed by a stream of $N_2$ and the residue was dried in vacuo. A solution of the crude salt in dimethylformamide (0.2 mL) at 24° C. under Ar was treated sequentially with 96 (72% pure in 2,4-dinitrophenol, 9.1 mg, 19.3 μmol, 1.5 equiv) and Triethylamine (1.8 μL, 12.8 pmol, 1 equiv) and the reaction mixture was stirred for 19 h (24° C.). The solvent was removed in vacuo and the residue was washed with saturated aqueous $NAHCO_3$ (1 mL), $H_2O$ (0.5 mL), 10% aqueous citric acid (1 mL), and $H_2O$ (4×1 mL). Drying the solid in vacuo afforded 108 (6.3 mg, 6.9 mg theoretical, 91%) as a pale yellow solid: mp 257° C. (dec); $^1H$ NMR (DIMETHYLSULFOXIDE-$d_6$, 300 MHz) 11.84 (s, 1H, NH), 11.61 (s, 1H, NH), 8.62 (s, 1H, CONH), 8.42 (s, 1H, CONH), 8.28 (br d, 1H, J=9 Hz, C4-H), 7.94 (d, H, J=8.9 Hz, C4'-H), 7.32 (d, 1H, J=9 Hz, C5-H), 7.26 (d, 1H, J=8.9 Hz, C5'-H), 7.06 (s, 1H, C8'-H), 6.98 (s, 1H, C8-H), 4.64 (t, 2H, J=8.3 Hz, C2-$H_2$), 4.02 (t, 2H, J=8.3 Hz, C2'-$H_2$), 3.2–3.6 (m, 4H, partly obscured by $H_2O$, C1-$H_2$, C1'-H), 1.43 (s, 9H, $C(CH_3)_3$); IR $(KBr)_{max}$ 3424, 1686, 1508, 1438, 1372, 1160, 800, 684 cm$^{-1}$.

Preparation of $N^1$[$N^2$-(tert-Butyloxycarbonyl)hydrazino] carbonyl-seco-CBI-$CDPI_2$ (110) (Illustrated in FIG. 17). A slurry of crude 16 freshly prepared from 14 (3.7 mg, 11.1 μmol), 1-(3-DIMETHYLAMINOPROPYL)-3-ETHYLCARBODIIMIDE HYDROCHLORIDE (EDCI) (6.4 mg, 33 μmol, 3 equiv), and 108 (6.0 mg, 11.1 μmol, 1 equiv) in dimethylformamide (0.2 mL) at 24° C. under Ar was vigorously stirred for 10 h. The solvent was removed in vacuo and the residue was washed with $H_2O$ (2×2 mL) and dried in vacuo. Flash chromatography (0.5×5 cm $SiO_2$, 0–66% dimethylformamide-toluene gradient elution) afforded 110 (5.5 mg, 8.4 mg theoretical, 65%) as a pale yellow solid: mp 250° C. (dec); $^1H$ NMR (DIMETHYLSULFOXIDE-$d_6$, 300 Mz) 11.83 (s, 1H, NH), 11.63 (s, 1H, NH), 10.45 (s, 1H, OH), 8.63 (s, 1H, CONH), 8.43 (s, 1H, CONH), 8.29 (br d, 1H, J=9 Hz, C4'-H), 8.13 (d, 1H, J=8.5 Hz, C6-H), 7.99 (s, 1H, C4-H), 7.95 (d, 1H, J=8.9 Hz, C4"-H), 7.87 (d, 1H, J=8.3 Hz, C9-H), 7.54 (t, 1H, J=7.6 Hz, C8-H), 7.40 (d, 1H, J=9.3 Hz, C5'-H), 7.38 (t, 1H, J=7.7 Hz, C7-H), 7.27 (d, 1H, J=8.9 Hz, C4"-H), 7.19 (s, 1H, C8'-H), 7.01 (s, 1H, C8"-H), 4.85 (t, 1H, J=10 Hz, C2-H), 4.68 (t, 2H, J=8 Hz, C2'-$H_2$), 4.59 (d, 1H, J=10 Hz, C2-H), 4.26 (m, 1H, CHHCl), 4.03 (t, 2H, J=8 Hz, C2"-$H_2$), 3.9–4.0 (m, 2H, C1-H), CHHCl), 3.2–3.6 (m, 4H, partly obscured by $H_2O$, C1'-$H_2$, C1"-$H_2$), 1.44 (s, 9H, $C(CH_3)_3$); IR $(KBr)_{max}$ 3410, 3315, 2962, 2927, 1664, 1610, 1582, 1508, 1416, 1370, 1340, 1262, 1158, 1098, 802, 762, 528 cm$^{-1}$; UV (dimethylformamide)$_{max}$ 340 (=43000), 310 (44000), 270 nm (26000); FABHRMS (DTT-DTE) m/e 760.2635 ($M^+$+H, $C_{41}H_{38}ClN_7O_6$ requires 760.2650).

Preparation of Compound 112 (Illustrated in FIG. 17)

A sample of 110 (1.0 equiv.) is treated with anhydrous 3N HCl-Ethylacetate (0.25 M) at 24° C. for 30 min. The solvent is then removed in vacuo to afford 112 as a white solid.

Preparation of 2-[(Benzyloxy)methyl]pyrrolo[3,2-e] benzoxazole (116) (Illustrated in FIG. 25). A solution of 5-hydroxyindole 114 (499 mg, 3.75 mmol) from Aldrich company and 2-(benzyloxy)ethylamine (1.13 g, 7.50 mmol, 2 equiv) monobenzylated from Aldrich company in anhydrous ethylene glycol dimethyl ether (DME, 120 mL) was cooled to 0° C. and activated $MnO_2$ (15 g, 30 wt equiv) was added. The reaction mixture was allowed to stir at 24° C. for 14 h before filtration through a Celite pad to remove $MnO_2$. The solvent was removed in vacuo. Flash chromatography ($SiO_2$, 2.5×25 cm, 40–50% Ethylacetate-hexane gradient elution) afforded 116 (500 mg, 1.04 g theoretical, 48%) as a pale orange-yellow oil: $^1H$ NMR ($CDCl_3$, 400 MHz) 8.98 (br s, 1H, NH), 7.27–7.40 (m, 8H, ArH), 6.92–6.93 (m, 1H, ArH), 4.84 (s, 2H, $PhCH_2$), 4.70 (s, 2H, C2-$CH_2$); $^{13}C$ NMR ($CDCl_3$, 100 MHz) 161.4 (C), 146.1 (C), 137.1 (C), 133.7 (C), 128.5 (two CH), 128.1 (two CH), 128.05 (CH), 127.8 (C), 125.3 (CH), 119.4 (C), 109.3 (CH), 104.8 (CH), 100.1 (CH), 73.2 ($CH_2$), 64.6 ($CH_2$); IR (neat)$_{max}$ 3265, 2862, 1671, 1452, 1367, 1212, 1089, 738, 698 cm$^{-1}$; FABHRMS (NBA) m/e 279.1140 ($M^+$+H, $C_{17}H_{14}N_2O_2$ requires 279.1134).

Preparation of 2-(Hydroxymethyl)pyrrolo[3,2-e] benzoxazole (118) (Illustrated in FIG. 25). A solution of 116 (67 mg, 0.24 mmol) in Ethanol (4 mL) was treated with 3 drops of conc HCl followed by 10% Pd—C (34 mg, 0.5 wt equiv). The reaction mixture was stirred at 24° C. under 1 atm of $H_2$ for 30 min, and neutralized with the addition of Triethylamine. The mixture was filtered through a Celite pad to remove the catalyst and the solvent was removed in vacuo. Flash chromatography (SiO$_2$, 1.0×20 cm, 60–80% Ethylacetate-hexane gradient elution) afforded 118 (31.5 mg, 45.1 mg theoretical, 70%) as a white crystalline solid: mp 169–171.5° C. (CH$_3$OH—CH$_2$Cl$_2$); $^1$H NMR (CD$_3$OD, 400 MHz) 7.42 (dd, 1H, J=0.8, 8.8 Hz, ArH), 7.36 (d, 1H, J=3.1 Hz, C7-H), 7.32 (d, 1H, J=8.8 Hz, ArH), 6.78 (dd, 1H, J=0.8, 3.1 Hz, C8-H), 4.82 (s, 2H, CH$_2$OH); $^{13}$C NMR (CD$_3$OD, 100 MHz) 165.5 (C), 147.0 (C), 135.6 (C), 133.3 (C), 126.8 (CH), 120.3 (C), 110.6 (CH), 105.0 (CH), 99.7 (CH), 58.2 (CH$_2$); IR (film)$_{max}$ 3266, 1566, 1438, 1364, 1221, 1083, 1037, 775, 735, 668 cm$^{-1}$; FABHRMS (NBA) m/e 189.0668 (M$^+$+H, C$_{10}$H$_8$N$_2$O$_2$ requires 189.0664). Anal. Calcd for C$_{10}$H$_8$N$_2$O$_2$: C, 63.81; H, 4.29; N, 14.89. Found: C, 63.50; H, 4.20; N, 14.50.

Preparation of methyl Pyrrolo[3,2-e]benzoxazole-2-carboxylate (120) (Illustrated in FIG. 25). A solution containing NaCN (42 mg, 0.85 mmol, 5 equiv) and activated MnO$_2$ (148 mg, 1.7 mmol, 10 equiv) in 10.5 mL of CH$_3$OH was treated with a solution of 118 (32 mg, 0.17 mmol) in CH$_3$OH (5.5 mL) at 0° C. under Ar. The reaction mixture was allowed to warm to 24° C. and was stirred for 4 h. The reaction mixture was filtered through a Celite pad (2×30 mL Ethylacetate wash) to remove MnO$_2$ and the combined organic layer was washed with H$_2$O, saturated aqueous NaCl, dried (Na$_2$SO$_4$), and concentrated in vacuo. Flash chromatography (SiO$_2$, 1×15 cm, 40% Ethylacetate-hexane) afforded 120 (37 mg, 37 mg theoretical, 100%) as an off-white solid: mp 207–208° C. (Ethylacetate-hexane); $^1$H NMR (CDCl$_3$, 400 MHz) 8.69 (br s, 1H, NH), 7.57 (d, 1H, J=8.9 Hz, ArH), 7.46 (d, 1H, J=8.9 Hz, ArH), 7.39 (t, 1H, J=2.8 Hz, C7-H), 7.05–7.06 (m, 1H, C-8H), 4.09 (s, 3H, CH$_3$); $^{13}$C NMR (CDCl$_3$, 100 MHz) 157.2 (C), 151.1 (C), 146.7 (C), 133.9 (C), 133.2 (C), 125.8 (CH), 119.8 (C), 113.0 (CH), 104.7 (CH), 100.4 (CH), 53.5 (CH$_3$); IR (film)$_{max}$ 3356, 2921, 1738, 1537, 1437, 1371, 1148 cm$^{-1}$; FABHRMS (NA) m/e 217.0610 (M$^+$+H, C$_{11}$H$_8$N$_2$O$_3$ requires 217.0613). Anal. Calcd for C$_{11}$H$_8$N$_2$O$_3$: C, 61.10; H, 3.73; N, 12.96. Found: C, 60.92; H, 3.71; N, 12.79.

Preparation of Methyl 1,2-Dihydro-3H-pyrrolo[3,2-e]benzoxazole-7-carboxylate (122) (Illustrated in FIG. 25). Compound 120 (47.6 mg, 0.22 mmol) was dissolved in CF$_3$CO$_2$H (1 mL) and cooled to 0° C. The mixture was stirred for 10 min before Et$_3$SiH (355 μL, 2.20 mmol, 10 equiv) was added to the reaction mixture. The mixture was warmed to 24° C. and stirred for 4.5 h. The solvent was removed under a stream of N$_2$ and the residue was dissolved in CH$_2$Cl$_2$ (10 mL), and washed with saturated aqueous NAHCO$_3$ (10 mL). The organic layer was dried (Na$_2$SO$_4$) and concentrated in vacuo to afford crude 9 as a yellow solid which was used directly in the next step without further purification due to its propensity to air oxidize back to starting material. For crude 122: $^1$H NMR (CDCl$_3$, 400 MHz) 7.25 (d, 1H, J=8.7 Hz, C5-H), 6.80 (d, 1H, J=8.7 Hz, C4-H), 4.01 (s, 3H, CH$_3$), 3.65 (t, 2H, J=8.6 Hz, C2-H$_2$), 3.31 (t, 2H, J=8.6 Hz, C1-H$_2$); FABHRMS (NBA) m/e 219.0768 (M$^+$ +H, C$_{11}$H$_{10}$N$_2$O$_3$ requires 219.0770).

Preparation of Methyl 3-Carbamoyl-1,2-dihydro-3H-pyrrolo[3,2-e]benzoxazole-7-carboxylate (124) (Illustrated in FIG. 25). A solution of crude 122 (from 0.22 mmol of 120) in anhydrous CH$_2$Cl$_2$ (2 mL) was treated with 85% trimethylsilyl isocyanate (Me$_3$SiNCO, 174 μL, 1.10 mmol, 5 equiv) and the mixture was stirred at 24° C. under N$_2$ for 4 h. The resulting insoluble residue was collected by centrifugation and washed with CH$_2$Cl$_2$ (2×3 mL) and CH$_3$OH (3 mL). Drying the solid in vacuo afforded pure 124 (32.7 mg, 57.4 mg theoretical, 57% from 120) as a pale yellow solid: mp>230° C. (dec); $^1$H NMR (DIMETHYLSULFOXIDE-d$_6$, 400MHz) 8.20 (d, 1H, J=9.0 Hz, C4-H), 7.57 (d, 1H, J=9.0 Hz, C5-H), 6.35 (br s, 2H, NH$_2$), 4.04 (t, 2H, J=8.9 Hz, C2-H$_2$), 3.96 (s, 3H, CH$_3$), 3.38 (t, 2H, J=8.9 Hz, C1-H$_2$); $^{13}$C NMR (DIMETHYLSULFOXIDE-d$_6$, 100 MHz) 156.5 (C), 155.9 (two C), 146.1 (C), 143.0 (C), 136.9 (C), 122.0 (C), 115.2 (CH), 109.3 (CH), 53.4 (CH$_3$), 48.2 (CH$_2$), 25.2 (CH); IR (film)$_{max}$ 3448, 3179, 1727, 1675, 1606, 1543, 1487, 1423, 1321, 1229, 1155, 1140, 1028, 818 cm$^{-1}$; FABHRMS (NBA) m/e 262.0830 (M$^+$+H, C$_{12}$H$_{11}$N$_3$O$_4$ requires 262.0828). Anal. Calcd for C$_{12}$H$_{11}$N$_3$O$_4$: C, 55.16; H, 4.25; N, 16.09. Found: C, 54.93; H, 4.17; N, 15.95.

Preparation of Methyl 3-(tert-Butyloxycarbonyl)-1,2-dihydro-3H-pyrrolo[3,2-e]benzoxazole-7-carboxylate (126) (Illustrated in FIG. 25). A solution of crude 122 (1.8 mg, 0.008 mmol) dissolved in tetrahydrofuran (100 L) was treated with di-tert-butyl dicarbonate (3.6 mg, 3.8 μL, 0.016 mmol, 2 equiv). The reaction mixture was stirred at 24° C. for 2 h and 4° C. for 24 h. The solvent was removed in vacuo and flash chromatography (SiO$_2$, 20–40% Ethylacetate-hexane gradient elution) afforded 126 (2.0 mg, 2.6 mg theoretical, 76%) as a pale yellow solid: $^1$H NMR (CDCl$_3$, 400 MHz) 8.17 (br s, 1H, C4-H), 7.43 (d, 1H, J=9.0 Hz, C5-H), 4.13 (t, 2H, J=8.8 Hz, C2-H$_2$), 4.07 (s, 3H, CH$_3$), 3.41 (t, 2H, J=8.8 Hz, C1-H$_2$), 1.56 (s, 9H, C(CH$_3$)$_3$); FABHRMS (NBA) m/e 319.1290 (M$^+$+H, C$_{16}$H$_{18}$N$_2$O$_5$ requires 319.1294).

Preparation of 3Carbamoyl-1,2-dihydro-3H-pyrrolo[3,2-e]benzoxazole-7-carboxylic Acid (128) (Illustrated in FIG. 25). A suspension of 124 (27 mg, 0.103 mmol) and LIOH H$_2$O (8.8 mg, 0.21 mmol, 2 equiv) in tetrahydrofuran-CH$_3$OH—H$_2$O (3:1:1, 2.5 mL) was stirred at 24° C. for 4 h. The solvent was removed under a stream of N$_2$ and the residual solid was suspended in H$_2$O (2 mL) and acidified with 1N aqueous HCl to pH 1. The insoluble residue was collected by centrifigation and washed with H$_2$O (2×3 mL). Drying the solid in vacuo afforded 128 (25 mg, 25 mg theoretical, 100%) as a pale yellow powder: mp>230° C. (dec); $^1$H NMR (CF$_3$CO$_2$D, 400 MHz) 8.31 (d, 1H, J=9.4 Hz, C4-H), 7.76 (d, 1H, J=9.4 Hz, C5-H), 4.41 (t, 1H, J=8.4 Hz, C2-H$_2$), 3.73 (t, 1H, J=8.4 Hz, C1-H$_2$); $^{13}$C NMR (DIMETHYLSULFOXIDE-d$_6$, 100 MHz) 155.9 (C), 154.8 (two C), 145.2 (C), 142.0 (C), 136.3 (C), 120.9 (C), 112.2 (CH), 108.4 (CH), 48.1 (CH$_2$), 25.2 (CH$_2$); IR (film)$_{max}$ 3476, 3174, 1677, 1606, 1481, 1419, 1369, 1234, 1061, 815 cm$^{-1}$; FABHRMS (NBA) m/e 248.0674 (M$^+$+H, C$_{11}$H$_9$N$_3$O$_4$ requires 248.0671).

Preparation of 1-(tert-Butyloxycarbonyl)-5-nitroindole (132) (Illustrated in FIG. 26)

A solution of 5-nitroindole (130, 2.0 g, 12.3 mmol) from Aldrich company and 4-DIMETHYLAMINOPYRIDINE (226 mg, 1.85 mmol, 0.15 equiv) in dioxane (90 mL) was treated with di-tert-butyl dicarbonate (5.38 g, 24.7 mmol, 2 equiv), and the reaction mixture was stirred at 24° C. for 10–15 min before the solvent was removed in vacuo. Flash chromatography (SiO$_2$, 2.5×25 cm, 20–50% Ethylacetate-hexane gradient elution) afforded 132 (3.17 g, 3.17 g theoretical, 100%) as an off-white solid: mp 135–137° C. (CH$_2$Cl$_2$, off-white fine needles); $^1$H NMR (CDCl$_3$, 400 MHz) 8.42 (d, 1H, J=2.1 Hz, C4-H), 8.21 (d, 1H, J=9.1 Hz, C7-H), 8.14 (dd, 1H, J=2.1, 9.1, Hz, C6-H), 7.70 (d, 1H, J=3.8 Hz, C2-H), 6.67 (d, 1H, J=3.8 Hz, C3-H), 1.67 (s, 9H, C(CH$_3$)$_3$); $^{13}$C NMR (CDCl$_3$, 100 MHz) 148.9 (C), 143.6 (C), 138.2 (C), 130.2 (C), 128.8 (CH), 119.4 (CH), 117.2 (CH), 115.2 (CH), 107.8 (CH), 85.1 (C), 28.0 (three CH$_3$); IR(film)$_{max}$ 2982, 1737, 1515, 1462, 1329, 1285, 1254, 1156, 1027, 904, 768, 745 cm$^{-1}$; FABHRMS (NBA) m/e 263.1043 (M$^+$+H, C$_{13}$H$_{14}$N$_2$O$_4$ requires 263.1032). Anal. Calcd for C$_{13}$H$_{14}$N$_2$O$_4$: C, 59.52; H, 5.38; N, 10.69. Found: C, 59.53; H, 5.36; N, 10.53.

Preparation of 5-Amino-1-(tert-butyloxycarbonyl)indole (134) (Illustrated in FIG. 26). A solution of 132 (1.0 g, 3.81 mmol) in Ethylacetate (30 mL) was treated with 10% Pd—C (500 mg, 0.5 wt equiv) and the mixture was stirred under 1 atm of H$_2$ at 24° C. for 5 h. The catalyst was removed by filtration through Celite, and the solvent was removed in vacuo. Flash chromatography (SiO$_2$, 2×20 cm, 40–60% Ethylacetate-hexane gradient elution) afforded 134 (593 mg, 884 mg theoretical, 67%) as a pale brown oil: $^1$H NMR (CDCl$_3$, 400 MHz) 7.90 (br s, 1H, C7-H), 7.50 (br s, 1H, C2-H), 6.82 (d, 1H, J=2.3 Hz, C4-H), 6.70 (dd, 1H, J=2.3, 8.7 Hz, C6-H), 6.39 (d, 1H, J=3.6 Hz, C3-H), 3.43 (br s, 2H, NH$_2$), 1.65 (s, 9H, C(CH$_3$)$_3$); $^{13}$C NMR (CDCl$_3$, 100 MHz) 149.8 (C), 142.3 (C), 131.7 (C), 129.1 (C), 126.2 (CH), 115.7 (CH), 113.8 (CH), 106.9 (CH), 106.0 (CH), 83.2 (C), 28.3 (three CH$_3$); IR (neat)$_{max}$ 3359, 1725, 1477, 1454, 1380, 1357, 1343, 1285, 1229, 1166, 1150, 1132, 1024cm$^{-1}$; FABHRMS (NBA) m/e 232.1212 (M$^+$, C$_{13}$H$_{16}$N$_2$O$_2$ requires 232.1212).

Preparation of 5-(2-Benzyloxyacetyl)amino-1-(tert-butyloxy-carbonyl)-indole (136) (Illustrated in FIG. 26). A solution of 134 (991 mg, 4.27 mmol) and K$_2$CO$_3$ (400 mg, 5.12 mmol, 1.2 equiv) in tetrahydrofuran (75 mL) was cooled to 0° C. and stirred for 10 min before benzyloxyacetyl chloride (851 μL, 5.12 mmol, 1.2 equiv) was added. The reaction mixture then was allowed to warm to 24° C. and stirred under N$_2$ for 2 h. The mixture was diluted with H$_2$O (100 nL), extracted with Ethylacetate (3×150 mL), dried (Na$_2$SO$_4$) and concentrated. Flash chromatography (SiO$_2$, 2×20 cm, 40–50% Ethylacetate-hexane gradient elution) afforded 136 (1.53 g, 1.62 g theoretical, 94%) as a pale yellow oil: $^1$H NMR (CDCl$_3$, 400 MHz) 8.37 (br s, 1H, NH), 8.06 (br d, 1H, J=8.6 Hz, C7-H), 7.95 (d, 1H, J=2.0 Hz, C4-H), 7.56 (d, 1H, J=3.9 Hz, C2-H), 7.34–7.41 (m, 5H, C$_6$H$_5$), 7.27(dd, 1H, J=2.0, 8.6 Hz, C6-H), 6.51 (d, 1H, J=3.9 Hz, C3-H), 4.65 (s, 2H, PhCH$_2$), 4.11 (s, 2H, COCH$_2$), 1.65 (s, 9H, C(CH$_3$)$_3$); $^{13}$C NMR (CDCl$_3$, 62.5 MHz) 167.4 (C), 149.5 (C), 136.5 (C), 132.2 (two C), 130.9 (C), 128.7 (two CH), 128.3 (CH), 128.0 (two CH), 126.6 (CH), 116.9 (CH), 115.3 (CH), 112.1 (CH), 107.3 (CH), 83.6 (C), 73.7 (CH$_2$), 69.6 (CH$_2$), 28.1 (three CH$_3$); IR (neat)$_{max}$ 3381, 2978, 1732, 1688, 1537, 1473, 1372, 1131, 745, 699cm$^{-1}$; FABHRMS (NBA) m/e 381.1823 (M$^+$+H, C$_{22}$H$_{24}$N$_2$O$_4$ requires 381.1814).

Preparation of 5(2-Benzyloxyacetyl)amino-1-(tert-butyloxycarbonyl)-4-nitroindole (138) (Illustrated in FIG. 26). Compound 136 (783 mg, 2.06 mmol) was dissolved in CH$_3$NO$_2$ (38 mL), cooled to 0° C., and treated with 65% HNO$_3$ (1.1 mL). The mixture was warmed to 24° C. and stirred for 3 h before it was diluted with H$_2$O (50 mL) and extracted with CH$_2$Cl$_2$ (3×40 mL). The organic layer was dried (Na$_2$SO$_4$) and concentrated. Flash chromatography (SiO$_2$, 2×20 cm, 20–40% Ethylacetate-hexane gradient elution) afforded 138 (570 mg, 878 mg theoretical, 65%) as a bright yellow solid: mp 145–146.5° C. (CH$_2$Cl$_2$, light yellow flakes); $^1$H NMR (CDCl$_3$, 400 MHz) 11.40 (br s, 1H, NH), 8.63 (d, 1H, J=9.4 Hz, ArH), 8.40 (d, 1H, J=9.4 Hz, ArH), 7.71 (d, 1H, J=4.0 Hz, C2-H), 7.27–7.40 (m, 5H, C$_6$H$_5$), 7.17 (d, 1H, J=4.0 Hz, C3-H), 4.68 (s, 2H, PhCH$_2$), 4.10 (s, 2H, COCH$_2$), 1.62 (s, 9H, C(CH$_3$)$_3$); $^{13}$C NMR (CDCl$_3$, 100 MHz) 168.9 (C), 148.8 (C), 136.5 (C), 132.2 (C), 130.7 (C), 129.8 (CH), 129.6 (C), 128.6 (two CH), 128.2 (CH), 128.0 (two CH), 125.7 (C), 122.2 (CH), 117.9 (CH), 107.2 (CH), 85.2 (C), 73.8 (CH$_2$), 69.7 (CH$_2$), 28.1 (three CH$_3$); IR (film)$_{max}$ 3319, 1737, 1701, 1491, 1372, 1323, 1288, 1152, 1108 cm$^{-1}$; FABHRMS (NBA) m/e 425.1605 (M$^+$+H, C$_{22}$H$_{23}$N$_3$O$_6$ requires 425.1587). Anal. Calcd for C$_{22}$H$_{23}$N$_3$O$_6$: C, 62.09; H, 5.45; N, 9.88. Found: C, 61.84; H, 5.47; N, 9.99.

Preparation of 4-Amino-(2-benzyloxyacetyl)amino-1-(tertbutyloxy-carbonyl)-indole (140) (Illustrated in FIG. 26). Method A. Compound 138 (212 mg, 0.50 mmol) was dissolved in tetrahydrofuran (3.5 mL) and treated with a solution of Na$_2$S$_2$O$_4$ (870 mg, 5.0 mmol, 10 equiv) in H$_2$O (3.5 mL). The reaction mixture was stirred at 24° C. under N$_2$ for 20 h before it was diluted with H$_2$O (10 mL), and extracted with Ethylacetate (3×10 mL). The organic layer was dried (Na$_2$SO$_4$) and concentrated. Flash chromatography (SiO$_2$, 1.5×20 cm, 50–60% Ethylacetate-hexane gradient elution) afforded 140 (138 mg, 197 mg theoretical, 70%) as a pale yellow oil identical in all respects to the sample described below.

Method B. A solution of 138 (910 mg, 2.13 mmol) in Ethylacetate (45 mL) was treated with 10% Pd—C (455 mg, 0.5 wt equiv) and the mixture was stirred under 1 atm of H$_2$ at 24° C. for 3 h. The catalyst was removed by filtration through Celite, and the solvent was removed in vacuo. Flash chromatography (SiO$_2$, 2×25 cm, 60% Ethylacetate-hexane) afforded 140 (776 mg, 846 mg theoretical, 92%) as a pale yellow oil (no debenzylation product was detected): $^1$H NMR (CDCl$_3$, 400 MHz) 8.23 (br s, 1H, NH), 7.55 (d, 1H, J=8.7 Hz, ArH), 7.49 (d, 1H, J=3.8 Hz, C2-H), 7.34–7.39 (m, 5H, C$_6$H$_5$), 7.01 (d, 1H, J=8.7 Hz, ArH), 6.50 (d, 1H, J=3.8 Hz, C3-H), 4.67 (s, 2H, PhCH$_2$), 4.17 (s, 2H, COCH$_2$), 4.16 (br s, 2H, NH$_2$), 1.64 (s, 9H, C(CH$_3$)$_3$); $^{13}$C NMR (CDCl$_3$, 100 MHz) 168.4 (C), 149.8 (C), 136.8 (C), 134.6 (C), 134.5 (C), 128.8 (two CH), 128.4 (CH), 128.2 (two CH), 124.8 (CH), 122.7 (CH), 120.6 (C), 116.1 (C), 106.2 (CH), 103.9 (CH), 83.8 (C), 73.8 (CH$_2$), 69.7 (CH$_2$), 28.3 (three CH$_3$); IR (neat)$_{max}$ 3362, 2978, 1731, 1676, 1491, 1350, 1299, 1152, 1126cm$^{-1}$; FABHRMS (NBA-CsI) m/e 528.0878 (M$^+$+Cs, C$_{22}$H$_{25}$N$_3$O$_4$ requires 528.0899). Anal. Calcd for C$_{22}$H$_{25}$N$_3$O$_4$: C, 66.80; H, 6.38; N, 10.63. Found: C, 66.58; H, 6.34; N, 10.39.

Preparation of 2-[(Benzyloxy)methyl]-6-(tert-butyloxycarbonyl)-pyrrolo-3,2-e]benzimidazole (142) (Illustrated in FIG. 26). Compound 140 (192 mg, 0.484 mmol) was dissolved in tetrahydrofuran (25 mL) and treated with a solution of tetrahydrofuran (5 mL) containing 2 drops of conc H$_2$SO$_4$. The mixture was stirred at 24° C. under N$_2$ for 24 h before the reaction was neutralized with the addition of saturated aqueous NaHCO$_3$ (20 mL). The mixture was extracted with Ethylacetate (3×20 mL) and the organic layer was concentrated in vacuo. Flash chromatography (SiO$_2$, 1.5×20 cm, 40–50% Ethylacetate-hexane gradient elution) afforded 142 (181 mg, 183 mg theoretical, 99%) as a pale orange oil: $^1$H NMR (CDCl$_3$, 400 MHz) 8.15 (d, 1H, J=8.8 Hz, C5-H), 7.66 (d, 1H, J=3.5 Hz, C7-H), 7.45 (br d, 1H, J=8.8 Hz, C4-H), 7.32–7.36 (m, 5H, C$_6$H$_5$), 6.92 (br s, 1H, C8-H), 4.91 (s, 2H, PhCH$_2$), 4.65 (s, 2H, C2-CH$_2$), 1.69 (s, 9H, C(CH$_3$)$_3$); IR (neat) 2978, 1732, 1436, 1370, 1343, 1286, 1150, 1128 cm$^{-1}$; FABHRMS (NBA) m/e 378.1826 (M$^+$+H, C$_{22}$H23N$_3$O$_3$ requires 378.1818).

Preparation of 6-(tert-Butyloxycarbonyl)-2-(hydroxymethyl)pyrrolo[3,2-e]benzimidazole (144) (Illustrated in FIG. 26). A solution of 142 (677 mg, 1.79 mmol) in Ethanol (20 mL) was treated with 3 drops of conc HCl followed by 10% Pd—C (340 mg, 0.5 wt equiv). The reaction mixture was stirred at 24° C. under 1 atm of $H_2$ for 5 h before being quenched with the addition of several drops of Triethylamine. The catalyst was removed by filtration through Celite, and the solvent was removed in vacuo. Flash chromatography ($SiO_2$, 2×25 cm, 10–20% $CH_3OH$-Ethylacetate gradient elution) afforded 144 (481 mg, 516 mg theoretical, 93%) as an off-white powder: mp 152° C. (dec, $CH_3OH$—$CH_2Cl_2$); $^1H$ NMR ($CD_3OD$, 400 MHz) 8.10(d, 1H, J=9.0 Hz, C5-H), 7.67 (d, 1H, J=3.7Hz, C7-H), 7.44 (d, 1H, J=9.0 Hz, C4-H), 6.93 (d, 1H, J=3.7 Hz, C8-H), 4.87 (s, 2H, $CH_2OH$), 1.69 (s, 9H, $C(CH_3)_3$); $^{13}C$ NMR ($CD_3OD$—$CDCl_3$, 400 MHz) 154.0 (C), 150.9 (C), 133.2 (C), 132.7 (C), 132.0 (C), 126.1 (CH), 119.7 (C), 111.5 (CH), 110.9 (CH), 104.9(CH), 84.6 (C), 58.6 ($CH_2$), 28.4 (three $CH_3$); IR (film)$_{max}$ 3179, 2920, 1729, 1676, 1365, 1342, 1289, 1150, 1126 cm$^{-1}$; FABHRMS (NBA-NaI) m/e 310.1160 ($M^+$+Na, $C_{15}H_{17}N_3O_3$ requires 310.1168).

Methyl 6-(tert-Butyloxycarbonyl)pyrrolo[3,2-e] benzimidazole2-carboxylate (146) (Illustrated in FIG. 26). A solution containing NaCN (478 mg, 9.75 mmol, 5 equiv) and activated $MnO_2$ (1.69 g, 19.5 mmol, 10 equiv) in $CH_3OH$ (42 mL) was treated with a solution of 144 (560 mg, 1.95 mmol) in $CH_3OH$ (17 mL) at 0° C. under Ar. The reaction mixture was allowed to warm to 4° C. and was stirred for 8 h. The reaction mixture was filtered through a Celite pad (Ethylacetate wash) to remove $MnO_2$. Ethylacetate was added (150 mL total) and the combined organic layer was washed with $H_2O$ (100 mL), saturated aqueous NaCl, dried ($Na_2SO_4$), and concentrated in vacuo. Flash chromatography ($SiO_2$, 2×25 cm, 60–80% Ethylacetate-hexane gradient elution) afforded 146 (485 mg, 615 mg theoretical, 79%) as a light yellow foam: $^1H$ NMR ($CDCl_3$, 400 MHz) 8.26 (d, 1H, J=9.0 Hz, C5-H), 7.64 (d, 1H, J=3.6 Hz, C7-H), 7.49 (d, 1H, J=9.0 Hz, C4-H), 6.98 (br s, 1H, C8-H), 4.01 (s, 3H, $CO_2CH_3$), 1.62 (s, 9H, $C(CH_3)_3$); IR (film)$_{max}$ 3378, 1729, 1364, 1341, 1319, 1243, 1146, 1127 cm$^{-1}$; FABHRMS (NBA) m/e 316.1299 ($M^+$+H, $C_{16}H_{17}N_3O_4$ requires 316.1297). Anal. Calcd for $C_{16}H_{17}N_3O_4$: C, 60.93; H, 5.44; N, 13.33. Found: C, 60.84; H, 5.53; N, 12.97.

Preparation of Methyl Pyrrolo[3,2-e]benzimidazole-2-carboxylate (148) (Illustrated in FIG. 26). Compound 146 (100 mg, 0.32 mmol) was treated with anhydrous 3M HCl in Ethylacetate (10 mL) at 24° C. for 5 h. The reaction then was neutralized with saturated aqueous $NaHCO_3$ to pH 7–8 and extracted with Ethylacetate (2×10 mL) and $CH_3CN$ (2×15 mL). The combined organic layer was concentrated in vacuo to afford 148 as a yellow solid which was used in the next reaction without further purification. For 148: mp 182° C. (dec, $CH_3OH$—$CH_2Cl_2$, light yellow powder); $^1H$ NMR ($CD_3OD$, 400 MHz) 7.45 (d, 1H, J=8.8 Hz, ArH), 7.37 (d, 1H, J=8.8 Hz, ArH), 7.29 (d, 1H, J=3.0 Hz, C7-H), 6.85 (d, 1H, J=3.0 Hz, C8-H), 4.02 (s, 3H, $CO_2CH_3$);IR (film)$_{max}$ 3380, 1716, 1631, 1518, 1434, 1387, 1314, 1238 cm$^{-1}$; FABHRMS (NBA) m/e 216.0779 ($M^+$+H, $C_{11}H_9N_3O_2$ requires 216.0773).

Preparation of A Methyl 3-Carbamoyl-1,2-dihydro-3H-pyrrolo[3,2-e]benzimidazole-7-carboxylate (152) (Illustrated in FIG. 26). Crude 148 prepared above (0.32 mmol theoretical) was treated with $CF_3CO_2H$ (2.5 mL) and the mixture was stirred at 24° C. for 40 min. The reaction mixture was cooled to 0° C. before $Et_3SiH$ (510 µL, 3.17 mmol, 10 equiv) was added. The reaction mixture was warmed to 24° C. and stirred for 6 h. The solvent was removed under a stream of $N_2$ and the dry residue was dissolved in $CH_2Cl_2$ (20 mL). Several drops of $CH_3OH$ were added to help dissolve the residue. The organic solution was washed with saturated aqueous $NaHCO_3$ and concentrated in vacuo to afford 150 as a bright yellow solid which was used directly in the next reaction without further purification due to its propensity to air oxidize back to starting material. A solution of 150 dissolved in 10 mL of $CH_2Cl_2$-dimethylformamide (10:1) was treated with 85% $Me_3SiNCO$ (220 µL, 1.38 mmol, 5 equiv). The reaction mixture was stirred at 24° C. for 8 h. The solvent was removed in vacuo, and the dry residue was slurried in $CH_2Cl_2$ (5 mL). The sample was collected by centrifugation, washed with $CH_2Cl_2$ (2×) and $CH_3OH$ (1×) to afford pure 152 (55.4 mg, 82.5 mg theoretical, 67% from 146) as a light gray solid: mp>230° C. (dec); $^1H$ NMR ($CF_3CO_2D$, 400 MHz) 8.42 (d, 1H, J=9.4 Hz, C4-H), 7.78 (d, 1H, J=9.4 Hz, C5-H), 4.35 (t, 2H, J=8.4 Hz, C2-$H_2$), 4.21 (s, 3H, $CO_2CH_3$), 3.64 (t, 2H, J=8.4 Hz, C1-$H_2$), a doubling of the $^1H$ NMR signals was observed when the spectrum was recorded in DIMETHYLSULFOXIDE-$d_6$ which we attribute to the two accessible tautomeric forms of 152; $^{13}C$ NMR ($CF_3CO_2D$, 100 MHz) 160.8 (C), 156.6 (C), 145.7 (C), 139.4 (C), 130.5 (C), 130.3 (C), 121.9 (CH), 119.8 (C), 117.0 (CH), 57.5 ($CH_3$), 50.9 ($CH_2$), 27.0 ($CH_2$); IR (KBr)$_{max}$ 3406, 3187, 3027, 1727, 1664, 1441, 1394, 1209, 769 cm$^{-1}$; FABHRMS (NBA) m/e 261.0993 ($M^+$+H, $C_{12}H_{12}N_4O_3$ requires 261.0988).

Preparation of 3-Carbamoyl-1,2-dihydro-3H-pyrrolo[3,2-e]benzimidazole-7-carboxylic Acid (154) (Illustrated in FIG. 26). A suspension of 152 (50 mg, 0.19 mmol) in 6 mL of tetrahydrofuran-$CH_3OH$—$H_2O$ (3:1:1) was treated with LiOH $H_2O$ (16 mg, 0.38 mmol, 2 equiv). The reaction mixture was stirred at 24° C. under $N_2$ for 6 h before the solvent was removed in vacuo. The residual solid was mixed with $H_2O$ (3 mL) and acidified with 1N aqueous HCl to pH 1. The precipitate was collected by centrifugation and washed with $H_2O$ (2×2 mL). Drying the solid in vacuo afforded 154 (47 mg, 47 mg theoretical, 100%) as a pale yellow fluffy solid: mp>230° C. (dec); $^1H$ NMR ($CF_3CO_2D$, 400 MHz) 8.45 (d, 1H, J=9.2 Hz, C4-H), 7.83 (d, 1H, J=9.2 Hz, C5-H), 4.40 (t, 1H, J=8.4 Hz, C2-$H_2$), 3.69 (t, 1H, J=8.4 Hz, C1-$H_2$); $^{13}C$ NMR ($CF_3CO_2D$, 100 MHz) 160.7 (C), 157.8 (C), 145.4 (C), 140.1 (C), 130.6 (C), 130.2 (C), 121.7 (CH), 119.8 (C), 116.9 (CH), 50.8 ($CH_2$), 26.9 ($CH_2$); IR (film)$_{max}$ 3183, 1665, 1587, 1496, 1448, 1247, 1119 cm$^{-1}$; FABHRMS (NBA) m/e 247.0838 ($M^+$+H, $C_{11}H_{10}N_4O_3$ requires 247.0831).

Preparation of 3-[3'-Carbamoyl-1',2'-dihydro-3'H-pyrrolo[3',2'-e]benzoxazol-yl)carbonyl]-1-(chloromethyl)-5-hydroxy-1,2-dihydro-3H-benz[e]indole (156) (Illustrated in FIG. 27). Phenol 14 (5.3 mg, 0.0159 mmol) was treated with anhydrous 3M HCl-Ethylacetate (2 mL) at 24° C. for 30 min. The solvent was removed in vacuo to afford crude unstable 16 (quantitative). A mixture of 16, [3-(dimethylamino)propyl]-ethylcarbodiimide hydrochloride (1-(3-DIMETHYLAMINOPROPYL)-3-ETHYLCARBODIIMIDE HYDROCHLORIDE (EDCI), 6.1 mg, 0.032 mmol, 2 equiv), and CDPBO 128 (3.7 mg, 0.015 mmol, 0.95 equiv) was stirred in dimethylformamide (400 µL) at 24° C. under Ar for 12 h. The solvent was removed in vacuo and the dry residue was mixed with $H_2O$ (1 mL) and stirred for 10 min. The precipitate was collected by centrifugation, and washed with $H_2O$ (2×1 mL) and dried in vacuo. Flash chromatography ($SiO_2$, 0.5×10 cm, 0–10% $CH_3OH$—$CHCl_3$ gradient elution) afforded 156 (6.4 mg, 7.3 mg theoretical, 88%) as a pale greenish powder: mp>230° C. (dec); $^1H$ NMR (DIMETHYLSULFOXIDE-$d_6$, 400 MHz) 10.57 (s, 1H, OH), 8.21 (d, 1H, J=9.0 Hz, C4'-H), 8.14 (d, 1H, J=8.3 Hz, C6-H), 8.02 (s, 1H, C4-H), 7.86 (d, 1H, J=8.4 Hz, C9-H), 7.61 (d, 1H, J=9.0 Hz, C5'-H), 7.55 (t, 1H, J=7.7 Hz, C8-H), 7.40 (t, 1H, J=7.8 Hz, C7-H), 6.36 (br s, 2H, NH$_2$), 4.90 (d, 1H, J=10.5 Hz, C2-H), 4.78 (dd, 1H, J=8.8, 11.9 Hz, C2-H), 4.23–4.25 (m, 1H, C1-H), 3.99–4.08 (m, 3H, CHHCl and C2'-H$_2$), 3.86 (dd, 1H, J=7.9, 10.9 Hz, CHHCl), 3.38–3.43 (m, 2H, C1'-H$_2$); $^{13}$C NMR (DIETHYLSULFOXIDE-d$_6$, 100 MHz) 156.1, 155.9, 154.4, 154.1, 145.4, 142.9, 141.3, 136.7, 129.8, 127.6, 123.8, 123.2, 123.1, 122.7, 121.8, 116.2, 114.5, 109.0, 100.0, 55.3, 48.2, 47.5, 41.2, 25.3; IR (film)$_{max}$ 3359, 3225, 1650, 1583, 1488, 1424, 1258, 1120, 1024, 764 cm$^{-1}$; FABHRMS (NBA) m/e 463.1182 (M$^+$+H, C$_{24}$H$_{19}$ClN$_4$O$_4$ requires 463.1173).Natural (1S)-156 [α]$^3$ +44 (c 0.12, dimethylformamide). Ent-(1R)-156: [α]$^3$ −41 (c 0.09, dimethylformamide).

Preparation of 3-[(3'-Carbamoyl-1',2'-dihydro-3'H-pyrrolo [3',2'-e]benzimidazol-7'-yl)carbonyl]-1-(chloromethyl)-5-hydroxy-1,2-dihydro-3H-benz[e]indole (158) (Illustrated in FIG. 27). Phenol 14 (4.6 mg, 0.0138 mmol) was treated with anhydrous 3M HCl-Ethylacetate (2 mL) at 24° C. for 40 min. The solvent was removed in vacuo to afford crude unstable 16 (quantitative). A mixture of 16, [3-(dimethylamino)propyl]-ethylcarbodiimide hydrochloride (1-(3-DIMETHYLAMINOPROPYL)-3-ETHYLCARBODIIMIDE HYDROCHLORIDE (EDCI), 5.3 mg, 0.028 mmol, 2 equiv) and CDPBI$_1$ 154 (3.4 mg, 0.14 mmol, 1 equiv) was stirred in dimethylformamide (400 μL) at 24° C. under N$_2$ for 6 h. The solvent was removed in vacuo. The dry residue was dissolved in 10% CH$_3$OH—CHCl$_3$ and loaded on a flash chromatography column (SiO$_2$, 0.8×10 cm) and eluted with 0–10% CH$_3$OH—CHCl$_3$ gradient elution to afford 158 (5.2 mg, 12.6 mg theoretical, 42%) as a light gray solid: mp>230° C. (dec); $^1$H NMR (DIMETHYLSULFOXIDE-d$_6$, 400 MHz) 13.16 (br s, 1H, NH), 10.49 (br s, 1H, OH), 8.09–8.14 (m, 2H, ArH), 8.03 (d, 1H, J=9.0 Hz, ArH), 7.86 (d, 1H, J=8.3 Hz, C9-H), 7.52–7.56 (apparent t, 2H, J=8.7 Hz, ArH), 7.38 (t, 1H, J=7.4 Hz, C7-H), 6.25 and 6.21 (two s, 2H, NH$_2$), 5.17 (d, 1H, J=10.4 Hz, C2-H), 4.83 (apparent t, 1H, J=9.2 Hz, C2-H), 4.24 (m, 1H, C1-H), 4.02 (t, 3H, J=8.7 Hz, CHHCl, C2'-H), 3.83–3.88 (m, 1H, CHHCl), 3.27–3.37 (m, 2H, obscured by H$_2$O, C1'-H$_2$); IR (film)$_{max}$ 3355, 3212, 2925, 1620, 1584, 1499, 1446, 1423, 1333, 1257, 1122, 1019cm$^{-1}$; FABHRMS (NBA) m/e462.1345 (M$^+$+H, C$_{24}$H$_{20}$ClN$_5$O$_3$ requires 462.1333) Natural (1S)-158: [α]$^3$ +49 (c 0.19, dimethylformamide).Ent-(1R)-158: [α]$^3$ −48 (c 0.04, dimethylformamide).

Preparation of N$^2$-[(3'-carbamoyl-1',2'-dihydro-3'H-pyrrolo[3',2'-e]benzimidazol-7'-yl)carbonyl]-1,2,9,9a-tetrahydro-cyclopropa-[c]-enz[e]-indol-4-one (162) or COMPOUND (160) (Illustrated in FIG. 27). A solution of 156 or 158 (1.4 mg, 3 μmol) in 300 μL of tetrahydrofuran-dimethylformamide (1:1) was cooled to 0° C. and treated with DBN (0.5 μL, 4.5 μmol, 1.5 equiv). The reaction mixture was slowly warmed to 24° C. and stirred for 3.5 h. The mixture was placed on a flash chromatography column (SiO$_2$, 0.5×3 mm), and eluted with 5–10% CH$_3$OH—CHCl$_3$ (gradient elution) to afford 160 or 162 (0.8 mg, 1.3 mg theoretical, 63%) as a bright yellow solid. Selected representative data for 162: mp>230° C.; $^1$H NMR (dimethylformamide-d$_7$, 400 MHz) 13.40 (br s, 1H, NH), 8.21 (d, 1H, J=8.9 Hz, C4'-H), 8.10 (d, 1H, J=7.8 Hz, C5-H), 7.64 (t, 1H, J=7.5 Hz, C7-H), 7.55 (d, 1H, J=8.9 Hz, C5'-H), 7.48 (t, 1H, J=8.0 Hz, C6-H), 7.31 (s, 1H, C4-H), 7.29 (d, 1H, J=7.8 Hz, C8-H), 6.29 (br s, 2H, NH$_2$), 5.33 (d, 1H, J=11.8 Hz, C1'-H), 4.77 (dd, 1H, J=5.0, 11.8 Hz, C1-H), 4.20 (t, 1H, J=8.8 Hz, C2'-H$_2$), 3.44 (t, 2H, partially obscured by H$_2$O, J=8.8 Hz, C1'-H$_2$), 3.31–3.35 (m, 1H, C9a-H), 1.76–1.80 (m, 2H, C9-H$_2$); IR (film)$_{max}$ 1656, 1620, 1589, 1495, 1442, 1406, 1272, 1125 cm$^{-1}$; FABHRMS (NBA) m/e 426.1545 (M$^+$+H, C$_{24}$H$_{19}$N$_5$O$_3$ requires 426.1566). Natural (+)-162: [α]$^3$ +95 (c 0.04, dimethylformamide). Ent-(−)-162: [α]$^4$ −94 (c 0.05, dimethylformamide).

DNA Alkylation Studies. General procedures, the preparation of singly $^{32}$P 5' end-labeled double-stranded DNA, the agent binding studies, gel electrophoresis, and autoradiography were conducted according to procedures described in full detail elsewhere. (Boger et. al Tetrahedron 1991, 47, 2661). Eppendorf tubes containing the 5' end-labeled DNA (9 μL, w794 and w836) in TE buffer (10 mM Tris, 1 mM EDTA, pH 7.5) were treated with the agent DIMETHYL-SULFOXIDE (1 μL at the specified concentration). The solution was mixed by vortexing and brief centrifugation and subsequently incubated at 25° C. for 3 days. The covalently modified DNA was separated from unbound agent by Ethanol precipitation and resuspended in TE buffer (10 μL). The solution of DNA in an Eppendorf tube sealed with parafilm was heated at 100° C. for 30 min to induce cleavage at the alkylation sites, allowed to cool to 25° C. and centrifuged. Formamide dye (0.33% xylene cyanol FF, 0.03% bromophenol blue, 8.7% Na$_2$EDTA 250 mM) was added (5 μL) to the supernatant. Prior to electrophoresis, the sample was denatured by warming at 100° C. for 5 min, placed in an ice bath, and centrifuged, before the supernatant (3 μL) was loaded directly onto the gel. Sanger dideoxynucleotide sequencing reactions were run as standards adjacent to the reaction samples. Polyacrylamide gel electrophoresis (PAGE) was run on an 8% sequencing gel under denaturing conditions (8 M urea) in TBE buffer (100 mM Tris, 100 mM boric acid, 0.2 mM Na$_2$EDTA) followed by autoradiography.

Preparation of Compounds 164,166,168 (Illustrated in FIG. 29)

Condensation of 3-nitrobenzaldehyde with methyl 2-azidoacetate (8 equiv, 6 equiv NaOCH$_3$, CH$_3$OH, −23 to 0° C., 6 h, 88%) both reagents commercially available from Aldrich, followed by thermolysis of the resulting methyl 2-azidocinnamate (xylene, reflux, 4.5 h, 81%) provided a readily separable mixture (4:1) of methyl 5- and 7-nitroindole-2-carboxylate. For methyl 7-nitroindole-2-carboxylate (164): mp 122–125° C. (CH$_2$Cl$_2$, light yellow fine needles); $^1$H NMR (CDCl$_3$, 400 MHz) 10.37 (br s, 1H, NH), 8.31 (d, 1H, J=8.0 Hz, C4-H), 8.06 (d, 1H, J=8.0 Hz, C6-H), 7.36 (d, 1H, J=2.4 Hz, C3-H), 7.28 (t, 1H, J=8.0 Hz, C5-H), 3.99 (s, 3H, CO$_2$CH$_3$); IR (film)$_{max}$ 3372, 1727, 1531, 1445, 1344, 1298, 1249, 1188, 1107, 830, 763 cm$^{-1}$; FABHRMS (NBA) m/e 221.0560 (M$^+$+H, C$_{10}$H$_8$N$_2$O$_4$ requires 221.0562). For methyl 5-nitroindole-2-carboxylate (168): $^1$H NMR (DIMETHYLSULFOXIDE-d$_6$, 400 MHz) 12.65 (br s, 1H, NH), 8.73 (d, 1H, J=2.3 Hz, C4-H), 8.14 (dd, 1H, J=2.0, 8.0 Hz, C6-H), 7.60 (d, 1H, J=8.0 Hz, C7-H), 7.45 (d, 1H, J=0.7 Hz, C3-H), 3.90 (s, 3H, CO$_2$CH$_3$); IR (film)$_{max}$ 3316, 1701, 1614, 1531, 1435, 1343, 1261, 1203, 992, 746 cm$^{-1}$. Similarly, condensation of 4-nitrobenzaldehyde with methyl 2-azidoacetate (8 equiv, 6 equiv NaOCH$_3$, CH$_3$OH, −23 to 0° C., 7 h, 84%) followed by thermolysis (xylene, reflux, 4 h, 83%) provided methyl 6-nitroindole-2-carboxylate (166): $^1$H NMR (CDCl$_3$, 400 MHz) 9.27 (br s, 1H, NH), 8.39 (d, 1H, J=2.0 Hz, C7-H), 8.04 (dd, 1H, J=2.0, 8.0 Hz, C5-H), 7.78 (d, 1H, J=8.0Hz, C4-H), 7.28 (d, 1H, J=2.3 Hz, C3-H), 4.00 (s, 3H, CO$_2$CH$_3$).

Preparation of Compounds 170,172,174 (Illustrated in FIG. 29)

Catalytic hydrogenation of 164,166 or 168 (1 atm H$_2$, 0.1 wt equiv 10% Pd—C, Ethylacetate, 25° C., 4–5 h) provided the corresponding amines. For methyl 7-aminoindole-2-carboxylate (170): 79%; mp 184° C. (dec, pale green crystals); $^1$H NMR (CDCl$_3$, 400 MHz) 9.47 (br s, 1H, NH), 7.21 (s, 1H, C3-H), 7.20 (d, 1H, J=7.4 Hz, C6-H), 6.99 (t, 1H, J=7.5 Hz, C5-H), 6.67 (d, 1H, J=7.4 Hz, C4-H), 3.97 (s, 3H, CO$_2$CH$_3$), 2.30 (br s, 2H, NH$_2$); IR (film)$_{max}$ 3205, 2815, 1693, 1547, 1437, 1345, 1247, 1211, 1112, 997, 827, 783, 734 cm$^{-1}$; FABHRMS (NBA) m/e 190.0747 (M$^+$+H, C$_{10}$H$_{10}$N$_2$O$_2$ requires 190.0742). For methyl 6-aminoindole-2-carboxylate (172): 76%, $^1$H NMR (CDCl$_3$, 400 MHz) 8.58 (br s, 1H, NH), 7.45 (d, 1H, J=8.4 Hz, C4-H), 7.11 (d, 1H, J=2.1 Hz, C3-H), 6.62 (d, 1H, J=1.9 Hz, C7-H), 6.59 (dd, 1H, J=1.9, 8.4 Hz, C5-H), 3.89 (s, 3H, CO$_2$CH$_3$), 3.79 (br s, 2H, NH$_2$); IR (film)$_{max}$ 3351, 2922, 1694, 1629, 1528, 1440, 1271, 1206, 1130, 999, 834, 736, 668 cm$^{-1}$; FABHRMS (NBA) m/e 190.0740 (M$^+$+H, C$_{10}$H$_{10}$N$_2$O$_2$ requires 190.0742). For methyl 5-aminoindole-2-carboxylate (174): 92%, mp 150–152° C. (CH$_2$Cl$_2$); $^1$H NMR (CDCl$_3$, 400 MHz) 8.72 (br s, 1H, NH), 7.23 (d, 1H, J=8.6 Hz, C7-H), 7.03 (dd, 1H, J=1.0, 2.1 Hz, C3-H), 6.93 (dd, 1H, J=1.0, 2.0 Hz, C4-H), 6.81 (dd, 1H, J=2.0, 8.6 Hz, C6-H), 3.93 (s, 3H, CO$_2$CH$_3$), 3.57 (br s, 2H, NH$_2$); $^{13}$C NMR (CDCl$_3$, 100 MHz) 160.0 (C), 150.3 (C), 145.6 (C), 143.0 (C), 127.7 (C), 117.7 (CH), 113.5 (CH), 112.6 (CH), 106.1 (CH), 52.2(CH$_3$);R (film)$_{max}$ 3320, 1691, 1628, 1531, 1437, 1376, 1337, 1232, 1034, 997, 766 cm$^{-1}$; FABHRMS (NBA) m/e 190.0746 (M$^+$+H, C$_{10}$H$_{10}$N$_2$O$_2$ requires 190.0742).

General Method for the Preparation of Trimethylammonium Substituted Indole-2-carboxylate Methyl Esters: Methyl 5-(Trimethylammonio)indole-2-carboxylate Iodides (176–180) (Illustrated in FIG. 29). Compound 174 (76 mg, 0.4 mmol) was dissolved in dimethylformamide (3 mL) and treated with NaHCO$_3$ (168 mg, 2.0 mmol, 5 equiv) and CH$_3$I (568 mg, 248 μL, 4.0 mmol, 10 equiv). The reaction mixture was stirred at 24° C. under N$_2$ for 4 h before the solvent was removed in vacuo. The dry residue was slurried in H$_2$O and precipitate was collected by centrifugation. Recrystallization from CH$_3$CN afforded 180 (129 mg, 144 mg theoretical, 90%) as a pale yellow solid: mp 228° C. (dec); $^1$H NMR (DIMETHYLSULFOXIDE-d$_6$, 400 MHz) 12.37 (br s, 1H, NH), 8.26 (d, 1H, J=2.6 Hz, C4-H), 7.89 (dd, 1H, J=2.6, 9.3 Hz, C6-H), 7.64 (d, 1H, J=9.3 Hz, C7-H), 7.29 (s, 1H, C3-H), 3.86 (s, 3H, CO$_2$CH$_3$), 3.65 (s, 9H, N(CH$_3$)$_3$); $^{13}$C NMR (DIMETHIMSULFOXIDE-d$_6$, 100 MHz) 161.4 (C), 140.6 (C), 136.4 (C), 129.7 (C), 125.9(C), 116.9 (CH), 114.1 (CH), 113.9 (CH), 108.9 (CH), 56.9 (three CH$_3$), 52.2 (CH$_3$); IR (film)$_{max}$ 3446, 1708, 1537, 1437, 1339, 1259, 1205, 995, 937, 770, 742 cm$^{-1}$; FABHRMS (NBA) m/e 233.1290 (M$^+$–I, C$_{13}$H$_{17}$IN$_2$O$_2$ requires 233.1290). Anal. Calcd for C$_{13}$H$_{17}$IN$_2$O$_2$: C, 43.35; H, 4.76; N, 7.78. Found: C, 42.99; H, 4.6; N, 7.51.

Methyl 7-(trimethylammonio)indole-2-carboxylate Iodide (176) procedure as above except with 170: mp 151.5° C. (dec, pale green fine needles); $^1$H NMR (CD$_3$CN, 400 MHz) 10.27 (br s, 1H, NH), 8.07 (d, 1H, J=8.0 Hz, C4-H), 7.81 (d, 1H, J=8.0 Hz, C6-H), 7.53 (s, 1H, C3-H), 7.41 (t, 1H, J=8.0 Hz, C5-H), 4.05 (s, 3H, CO$_2$CH$_3$), 3.89 (s, 9H, N(CH$_3$)$_3$); $^3$C NMR (CD$_3$OD, 100 MHz) 162.8 (C), 133.5 (C), 133.2 (C), 131.5 (C), 128.0 (C), 127.1 (CH), 121.7 (CH), 117.8 (CH), 111.2 (CH), 56.7 (three CH$_3$), 52.8 (CH$_3$); IR (film)$_{max}$ 3188, 1717, 1614, 1467, 1438, 1306, 1254, 1204, 1149, 944, 833, 731 cm$^{-1}$; FABHRMS (NBA) m/e 233.1297 (M$^+$–I, C$_{13}$H$_{17}$IN$_2$O$_2$ requires 233.1290). Anal. Calcd for C$_{13}$H$_{17}$IN$_2$O$_2$: C, 43.35; H, 4.76; N, 7.78. Found: C, 43.37; H, 4.73; N, 7.78.

Methyl 6-(Trimethylammonio)indole-2-carboxylate Iodide (178) procedure as above except with 172: mp 209° C. (dec, colorless crystals); $^1$H NMR (DIMETHYLSULFOXIDE-d$_6$, 400 MHz) 12.48 (br s, 1H, NH), 7.91 (d, 1H, J=9.0 Hz, C4-H), 7.80 (d, 1H, J=2.0 Hz, C7-H), 7.75 (dd, 1H, J=2.1, 9.1 Hz, C5-H), 7.25 (s, 1H, C3-H), 3.86 (s, 3H, CO$_2$CH$_3$), 3.68 (s, 9H, N(CH$_3$)$_3$); $^{13}$C NMR (DIETHYLSULFOXIDE-d$_6$, 100 MHz) 153.5 (C), 124.2 (C), 123.9 (C), 122.2 (C), 118.7 (C), 117.8 (CH), 112.4 (CH), 108.5 (CH), 101.9 (CH), 47.4 (three CH$_3$), 43.5 (CH$_3$); IR (film)$_{max}$ 3409, 1716, 1605, 1564, 1489, 1433, 1325, 1226, 1005, 942 cm$^{-1}$; FABHRMS (NBA) m/e 233.1290 (M$^+$–I, C$_{13}$H$_{17}$IN$_2$O$_2$ requires 233.1290). Anal. Calcd for C$_{13}$H$_{17}$IN$_2$O$_2$: C, 43.35; H, 4.76; N, 7.78. Found: C, 43.36; H, 4.72; N, 7.81.

General Method for the Preparation of Trimethylammonium Substituted Indole-2-carboxylic Acids: 5-(Trimethylammonio)indole-2-carboxylic Acid (182,184, 186) (Illustrated in FIG. 29). A solution of 180 (100 mg, 0.28 mmol) in tetrahydrofuran-CH$_3$OH—H$_2$O (3:1:1, 2.6 mL) was treated with LiOH—H$_2$O (35 mg, 0.83 mmol, 3 equiv), and the reaction mixture was stirred at 24° C. for 6 h. The solvent was removed and the dry residue was mixed with H$_2$O (10 mL) and saturated aqueous NaCl (5 mL). The solution was acidified to pH 1 with the addition of 1N aqueous HCl and extracted with CH$_3$CN (10 mL each) until no UV active material was detected in aqueous solution. The extracts were combined, dried (Na$_2$SO$_4$) and concentrated. Recrystallization from CH$_3$CN afforded 186 (73.8 mg, 96.2 mg theoretical, 77%) as a pale yellow solid: $^1$H NMR (DIMETHYLSULFOXIDE-d$_6$, 400 MHz) 13.31 (br s, 1H, CO$_2$H), 12.19 (br s, 1H, NH), 8.23 (d, 1H, J=1.8 Hz, C4-H), 7.88 (d, 1H, J=9.2 Hz, C6-H or C7-H), 7.59 (d, 1H, J=9.2 Hz, C6-H or C7-H), 7.19 (d, 1H, J-=1.1 Hz, C3-H), 3.65 (s, 9H, N(CH$_3$)$_3$); $^{13}$C NMR (DIMETHYLSULFOXIDE-d$_6$, 100MHz) 162.4 (C), 140.5 (C), 136.3 (C), 131.3 (C), 126.1 (C), 116.5 (CH), 133.8 (two CH), 108.2 (CH), 56.8 (three CH$_3$); IR (film)$_{max}$ 3342, 3016, 1697, 1538, 1469, 1419, 1339, 1226, 1194, 938, 852, 772 cm$^{-1}$; FABHRMS (NBA) m/e 219.1143 (M$^+$–Cl, C$_{12}$H$_{15}$ClN$_2$O$_2$ requires 219.1134.)

7-(Trimethylammonio)indole-2-carboxylic Acid (182) procedure as above except use 176: mp>198° C. (dec, white solid); $^1$H NMR (DIMETHYLSULFOXIDE-d$_6$, 400 MHz) 13.41 (br s, 1H, CO$_2$H), 12.23 (br s, 1IX NH), 7.94 (d, 1H, J=7.9 Hz, C4-H), 7.74 (d, 1H, J=8.0 Hz, C6-H), 7.38 (s, 1H, C3-H), 7.26 (t, 1H, J=8.0 Hz, C5-H), 3.79 (s, 9H, N(CH$_3$)$_3$); $^{13}$C NMR (DIMETHYLSLFOXIDE-d$_6$, 100 MHz) 162.2 (C), 132.2 (C), 131.5 (C), 131.3 (C), 126.6 (C), 125.3 (CH), 120.1 (CH), 116.9 (CH), 109.5 (CH), 55.5 (three CH$_3$); TR (film)$_{max}$ 3327, 1694, 1477, 1444, 1416, 1388, 1328, 1173, 1141, 940, 730cm$^{-1}$; FABHRMS (NBA) m/e 219.1141 (M$^+$–Cl, C$_{12}$H$_{15}$ClN$_2$O$_2$ requires 219.1134).

6-(Trimethylammonio)indole-2-carboxylic Acid (184) procedure as above except use 178: mp>195° C. (dec, off-white needles); $^1$H NMR (DIMETHYLSULFOXIDE-d$_6$, 400 MHz) 13.12 (br s, 1H, CO$_2$H), 12.33 (br s, 1H, NH), 7.88 (d, 1H, J=9.0 Hz, C4-H), 7.81 (d, 1H, J=2.2 Hz, C7-H), 7.73 (d, 1H, J=2.2, 9.0 Hz, C5-H), 7.17 (d, 1H, J=1.7 Hz, C3-H), 3.66 (s, 9H, N(CH$_3$)$_3$); $^{13}$C NMR (DIMETHYLSULFOXIDE-d$_6$, 100 MHz) 162.3 (C), 143.7 (C), 135.7 (C), 131.6 (C), 126.9 (C), 123.6 (CH), 112.5 (CH), 107.0 (CH), 104.5 (CH), 56.5 (three CH$_3$); IR (film)$_{max}$ 3260, 1689, 1530, 1328, 1222, 1131, 835, 778 cm$^{-1}$; FABHRMS (NBA) m/e 219.1142 (M$^+$–Cl, C$_{12}$H$_{15}$ClN$_2$O$_2$ requires 219.1134).

Preparation of 3-[(Indol-2'-yl)carbonyl]-1-(chloromethyl)-5-hydroxy-1,2-dihydro-3H-benz[e]indole (seco-CBI-indole$_1$, 190) (illustrated in FIG. 30). A sample of 14 (4.0 mg, 0.012 mmol) was treated with anhydrous 4 M HCl-Ethylacetate (1 mL) at 25° C. for 30 min. The solvent was removed in vacuo to afford crude unstable 16 (quantitative). A mixture of 16, [3-(dimethylamino)propyl] ethylcarbodiimide hydrochloride (1-(3-DIMETHYLAMINOPROPYL)-3-ETHYLCARBODIIMIDE HYDROCHLORIDE (EDCI), 5.8 mg, 0.030 mmol, 2.5 equiv), and indole-2-carboxylic acid (188, 2.9 mg, 0.018 mmol, 1.5 equiv) from Aldrich company in 0.2 mL of dimethylformamide was stirred at 25° C. under Ar for 16 h. The mixture was diluted with 0.3 mL of H$_2$O and extracted with Ethylacetate (0.4 LL×4). The combined organic layer was concentrated. Chromatography (SiO$_2$, 40% Ethylacetate-hexane) afforded 190 (3.4 mg, 4.3 mg theoretical, 79%) as a pale yellow solid: $^1$H NMR (tetrahydrofuran-d$_8$, 400 MHz) 11.04 (br s, 1H, NH), 9.31 (s, 1H, OH), 8.21 (d, 1H, J=8.3 Hz, C6-H), 8.02 (br s, 1H, C4-H), 7.78 (d, 1H, J=8.3 Hz, C9-H), 7.67 (d, 1H, J=7.9 Hz, C4'-H), 7.48 (dd, 1H, C8-H partially obscured by overlapping C7'-H), 7.47 (d, 1H, J=8.3 Hz, C7'-H), 7.30 (dd, 1H, J=8.0, 8.3 Hz, C7'-H), 7.22 (dd, 1H, J=7.1, 8.3 Hz, C6'-H), 7.17 (s, 1H, C3'-H), 7.06 (dd, 1H, J=7.1, 7.9 Hz, C5'-H), 4.78 (m, 2H, C2-H$_2$), 4.17 (m, 1H, C1-H), 4.00 (dd, 1H, J=3.2, 11.1 Hz, CHHCl), 3.61 (m, 1H, CHHCl); IR (film)$_{max}$, 3427, 3225, 3056, 2965, 2865, 1608, 1578, 1512, 1417, 1394, 1363, 1338, 1316, 1252, 1140, 1058, 850, 804, 743 cm$^{-1}$; FABHRMS (NBA) m/e 377.1065 (M$^+$+H, C$_{22}$H$_{17}$ClN$_2$O$_2$ requires 377.1057). Natural (1S)-2: [α]$^3$ +8.8 (c 0.17, tetrahydrofuran).

General Method for the Coupling of seco-N-BOC-CBI (14) with 15–17: 3-[7'-((Trimethylammonio)indol-2'-yl)carbonyl]-1-(chloromethyl)-5-hydroxy-1,2-dihydro-3H-benz[e]indoles (190,192,194,196) (Illustrated in FIG. 30). Phenol 14 (9.0 mg, 0.027 mmol) was treated with anhydrous 3M HCl-Ethylacetate (2 mL) at 24° C. for 30 min. The solvent was removed in vacuo to afford crude unstable 16 (quantitative). A mixture of 16, [3-(dimethylamino)propyl] ethylcarbodiimide hydrochloride (1-(3-DIMETHYLAMINOPROPYL)-3-ETHYLCARBODIIMIDE HYDROCHLORIDE (EDCI), 10.3 mg, 0.054 mmol, 2.0 equiv), and 182 (9.3 mg, 0.027 mmol, 1.0 equiv) in 0.5 mL of dimethylformamide was stirred at 24° C. under Ar for 12 h. The solvent was removed in vacuo and the dry residue was mixed with H$_2$O (3 mL) and saturated aqueous NaCl (2 mL). The mixture was extracted with CH$_3$CN (5 mL×3). The organic layer was dried (Na$_2$SO$_4$) and concentrated. Chromatography (SiO$_2$, n-Butanol-H$_2$O-Ethylacetate-HOAc, 5:5:5:3) afforded 192 (10.3 mg, 15.2 mg theoretical, 68%) as a pale yellow solid: mp>152° C. (dec); $^1$H NMR (CD$_3$OD, 400 MHz) 8.22 (d, 1H, J=8.3 Hz, C6-H), 8.02 (d, 1H, J=7.9 Hz, C4'-H), 7.97 (br s, 1H, C4-H), 7.81 (d, 1H, J=8.6 Hz, C6'-H or C9-H), 7.79 (d, 1H, J=8.4 Hz, C6'-H or C9-H), 7.55 (t, 1H, J=8.2 Hz, C8-H), 7.43 (s, 1H, C3'-H), 7.39 (t, 1H, J=8.2 Hz, C7'-H), 7.35 (t, 1H, J=8.0 Hz, C5'-H), 4.73–4.77 (m, 1H, C2-H), 4.65 (dd, J=1.7, 11.0 Hz, C2-H), 4.17–4.21 (m, 1H, C1-H), 4.00 (dd, 1H, J=3.1, 11.2 Hz, CHHCl), 3.90 (s, 9H, N(CH$_3$)$_3$), 3.69 (apparent t, 1H, J=10.6 Hz, CHHCl); IR (film)$_{max}$ 3354, 1624, 1584, 1466, 1414, 1326, 1259 cm$^{-1}$; FABHRMS (NBA) m/e 434.1648 (M$^+$-Cl, C$_{25}$H$_{25}$Cl$_2$N$_3$O$_2$ requires 434.1635). Natural (1S)-3: [ ]$^3$ −9.9 (c 0.10, CH$_3$OH).

3-[6'-((Trimethylammonio)indol-2'-yl)carbonyl]-1-(chloromethyl)-5-hydroxy-1,2-dihydro-3H-benz[e]indole (194) procedure as above except use 186: $^1$H NMR (CD$_3$OD, 400 MHz) 8.21 (d, 1H, J=8.3 Hz, C6-H), 7.99 (d, 1H, J=8.8 Hz, C4'-H), 7.87 (br s, 1H, C4-H), 7.80 (d, 1H, J=8.3 Hz, C9-H), 7.65 (dd, 1H, J=2.3, 9.3 Hz, C5'-H), 7.64 (s, 1H, C7'-H), 7.54 (t, 1H, J=8.2 Hz, C8-H), 7.36–7.45 (m, 1H, C7-H), 7.30 (s, 1H, C3'-H), 4.75–4.82 (m, 1H, C2-H), 4.70 (dd, 1H, J=1.8, 10.9 Hz, C2-H), 4.194.23 (m, 1H, C1-H), 4.00 (dd, 1H, J=3.2, 11.2 Hz, CHHCl), 3.75 (s, 9H, N(CH$_3$)$_3$), 3.69 (dd, 1H, J=3.0, 11.2 Hz, CHHCl); IR (film)$_{max}$ 3373, 1625, 1577, 1558, 1519, 1409, 1342, 1256 cm$^{-1}$; FABHRMS (NBA) m/e 434.1722 (M$^+$-Cl, C$_{25}$H$_{25}$Cl$_2$N$_3$O$_2$ requires 434.1714). Natural (1S)-4: [ ]$^3$ +53 (c 0.04, CH$_3$OH).

3-[5'-((Trimethylammonio)indol-2'-yl)carbonyl]-(chloromethyl)-5-hydroxy-1,2-dihydro-3H-benz[e]indole (196) procedure as above except use 188: $^1$H NMR (CD$_3$OD, 400 MHz) 8.27 (d, 1H, J=2.6 Hz, C4'-H), 8.21 (d, 1H, J=8.3 Hz, C6-H), 7.83 (br s, 1H, C4-H), 7.81 (dd, 1H, J=2.8, 9.3 Hz, C6'-H), 7.80 (d, 1H, J=8.3 Hz, C9-H), 7.73 (d, 1H, J=9.2 Hz, C7'-H), 7.53 (t, 1H, J=8.2 Hz, C8-H), 7.37 (t, 1H, J=8.4 Hz, C7-H), 7.33 (s, 1H, C3'-H), 4.68–4.76 (m, 2H, partially obscured by H$_2$O, C2-H2), 4.17–4.21 (m, 1H, C1-H), 3.99 (dd, H, J=3.2, 11.2 Hz, CHHCl), 3.73 (s, 9H, N(CH$_3$)$_3$), 3.65 (dd, 1H, J=8.8, 11.2 Hz, CHHCl); IR (film)$_{max}$ 3374, 1557, 1416, 1342, 1265, 1232, 758 cm$^{-1}$; FABHRMS (NBA) m/e 434.1619 (M$^+$-Cl, CH$_{25}$H$_{25}$Cl$_2$N$_3$O$_2$ requires 434.1635). Natural (1S)-5 [ ]$^3$+64 (c 0.10, CH$_3$OH).

DNA Alkylation Studies of 2-5: Selectivity and Efficiency. Eppendorf tubes containing singly $^{32}$P 5'-end-labeled double-stranded DNA[10] (9 μL) in TE buffer (10 mM Tris, 1 mM EDTA, pH 7.5) were treated with the agents 190–196 in DIMETHYLSULFOXIDE (1 μL, at the specified concentrations). The solutions were mixed by vortexing and brief centrifugation and subsequently incubated at 4° C. for 24 h. The covalently modified DNA was separated from unbound agent by Ethanol precipitation of the DNA. The Ethanol precipitations were carried out by adding t-RNA as a carrier (1 μL, 10 1μg/μL), a buffer solution containing salt (0.1 volume, 3 M NaOAc in TE) and −20° C. Ethanol (2.5 volumes). The solutions were mixed and chilled at −78° C. in a REVCO freezer for 1 h or longer. The DNA was reduced to a pellet by centrifugation at 4° C. for 15 min, washed with −20° C. 70% Ethanol (in TE containing 0.2 M NaCl) and recentrifuged briefly. The pellets were dried in a Savant Speed Vac concentrator and resuspended in TE buffer (10 μL). The solutions of alkylated DNA were warmed at 100° C. for 30 min to induce cleavage at the adenine N3 alkylation sites. After brief centrifugation, formamide dye solution (5 μL) was added. Prior to electrophoresis, the samples were denatured by warming at 100° C. for 5 min, placed in an ice bath, centrifuged briefly, and the supernatant (2.8 μL) was loaded onto a gel. Sanger dideoxynucleotide sequencing reactions were run as standards adjacent to the agent treated DNA reaction samples. Polyacrylamide gel electrophoresis (PAGE) was run on an 8% sequencing gel under denaturing conditions (19:1 acrylamide: N,N'-methylenebisacrylamide, 8 M urea) in TBE buffer (100 mM Tris, 100 mM boric acid, 0.2 mM Na$_2$EDTA). PAGE was pre-run for 30 min with formamide dye solution prior to loading the samples. Autoradiography of dried gels was carried out at −78° C. using Kodak X-Omat AR film and a Picker Spectra™ intensifying screen.

What is claimed:

1. A compound represented by the following structure:

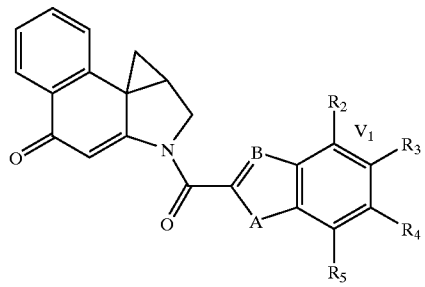

wherein:
A is selected from the group consisting of NH and O;
B is selected from the group consisting of C and N;
$R_2$ is incorporated into a first N-substituted pyrrolidine ring containing $V_1$, a double bond between $R_2$ and $R_3$, or is selected from the group consisting of hydrogen, hydroxyl, and O-alkyl (C1–C6);
$R_3$ is incorporated into the first N-substituted pyrrolidine ring containing $V_1$, a double bond between $R_2$ and $R_3$, or is NH—C(O)—$R_6$;
$R_4$ is selected from the group consisting of hydrogen, hydroxyl, and O-alkyl (C1–C6);
$R_5$ is selected from the group consisting of hydrogen, hydroxyl, and O-alkyl (C1–C6); and
the first N-substituted pyrrolidine ring containing $V_1$ being fused to the double bond between $R_2$ and $R_3$ and being represented by the following structure:

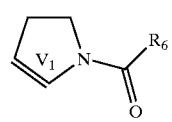

wherein:
$R_6$ is a radical represented by the following structure:

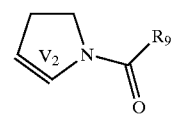

wherein:
E is selected from the group consisting of NH, S, and O;
D is selected from the group consisting of C and N;
$R_7$ is incorporated into a second N-substituted pyrrolidine ring containing $V_2$, a double bond between $R_7$ and $R_8$, or is selected from the group consisting of hydrogen, hydroxyl, and O-alkyl (C1–C6);
$R_8$ is incorporated into a second N-substituted pyrrolidine ring containing $V_2$, a double bond between $R_7$ and $R_8$, or is selected from the group consisting of hydrogen, hydroxyl, and O-alkyl (C1–C6);
the second N-substituted pyrrolidine ring containing $V_2$ being fused to the double bond between $R_7$ and $R_8$ and being represented by the following structure:

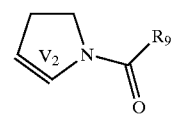

wherein:
$R_9$ is selected from the group consisting of —$CH_2CH_3$, -alkyl, —$NHCH_3$, —N-alkyl, —$OCH_3$, —O-alkyl, —$NH_2$, —$NHNH_2$, and —$NHNHCO_2$-t-Bu, with the following provisos:

if $R_2$ participates in the first N-substituted pyrrolidine ring, then $R_3$ also participates in the first N-substituted pyrrolidine ring;

if $R_3$ participates in the first N-substituted pyrrolidine ring, then $R_2$ also participates in the first N-substituted pyrrolidine ring;

if $R_7$ participates in the N-substituted pyrrolidine ring, then $R_8$ also participates in the N-substituted pyrrolidine ring;

if $R_8$ participates in the N-substituted pyrrolidine ring only if $R_7$ also participates in the N-substituted pyrrolidine ring;

if A and E are simultaneously NH, then B and D can not simultaneously be C; and if E is S, then B and D are C.

2. A compound according to claim 1 represented by the following stereoisometric structure:

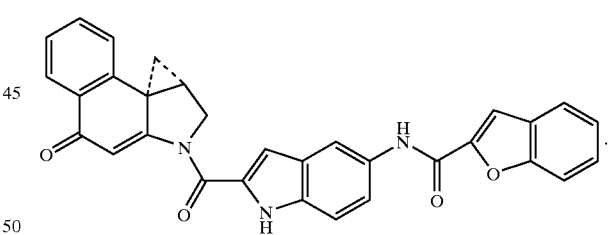

3. A compound according to claim 1 represented by the following stereoisometric structure:

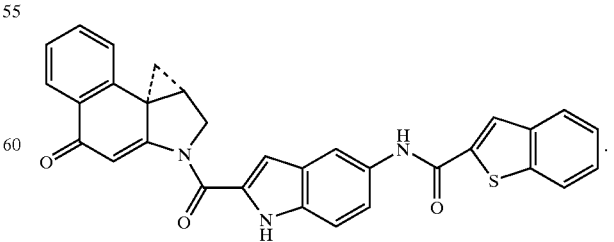

4. A compound according to claim 1 represented by the following stereoisometric structure:

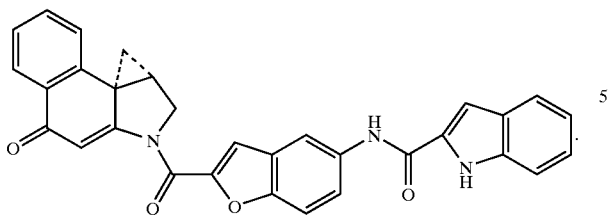

5. A compound according to claim 1 represented by the following stereoisometric structure:

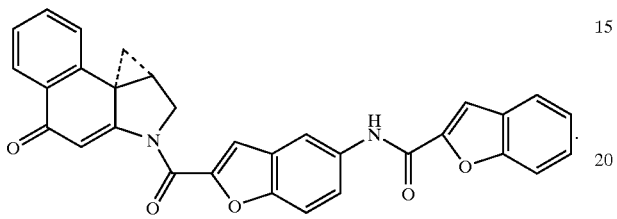

6. A compound according to claim 1 represented by the following stereoisometric structure:

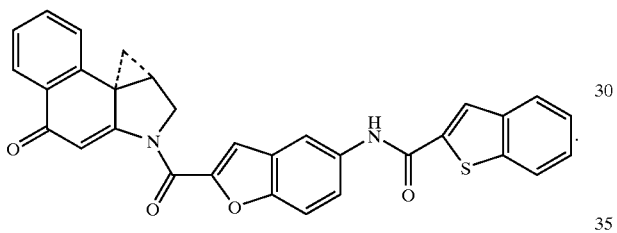

7. A composition having a radical represented by the following structure:

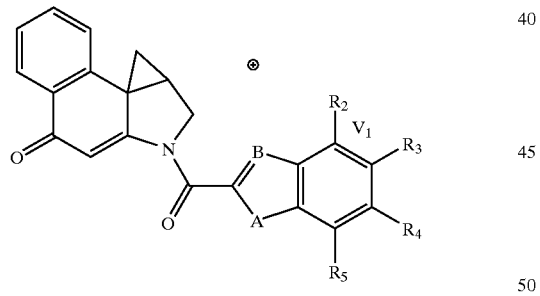

wherein:
A is selected from the group consisting of NH and O;
B is selected from the group consisting of C and N;
$R_2$ is incorporated into a first N-substituted pyrrolidine ring containing $V_1$, a double bond between $R_2$ and $R_3$, or is selected from the group consisting of hydrogen, hydroxyl, O-alkyl (C1–C6), and $N^+$-alkyl $(C1–C6)_3$;
$R_3$ is incorporated into the first N-substituted pyrrolidine ring containing $V_1$, a double bond between $R_2$ and $R_3$, or is NH—C(O)—$R_6$;
$R_4$ is selected from the group consisting of hydrogen, hydroxyl, O-alkyl (C1–C6), and $N^+$-alkyl $(C1–C6)_3$;
$R_5$ is selected from the group consisting of hydrogen, hydroxyl, O-alkyl (C1–C6), and $N^+$-alkyl $(C1–C6)_3$; and the first N-substituted pyrrolidine ring containing $V_1$ being fused to the double bond between $R_2$ and $R_3$ and being represented by the following structure:

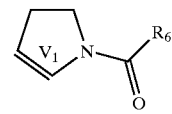

wherein:
$R_6$ is a radical represented by the following structure:

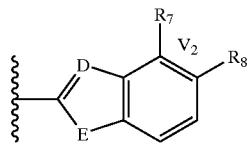

wherein:
E is selected from the group consisting of NH, S, and O;
D is selected from the group consisting of C and N;
$R_7$ is incorporated into a second N-substituted pyrrolidine ring containing $V_2$, a double bond between $R_7$ and $R_8$, or is selected from the group consisting of hydrogen, hydroxyl, O-alkyl (C1–C6), and $N^+$-alkyl $(C1–C6)_3$;
$R_8$ is incorporated into a second N-substituted pyrrolidine ring containing $V_2$, a double bond between $R_7$ and $R_8$, or is selected from the group consisting of hydrogen, hydroxyl, O-alkyl (C1–C6), and $N^+$-alkyl $(C_1–C6)_3$;
the second N-substituted pyrrolidine ring containing $V_2$ being fused to the double bond between $R_7$ and $R_8$ and being represented by the following structure:

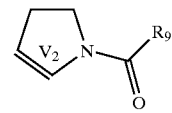

wherein:
$R_9$ is selected from the group consisting of —$CH_2CH_3$, -alkyl, —$NHCH_3$, —N-alkyl, —$OCH_3$, —O-alkyl, —$NH_2$, —$NHNH_2$, and —$NHNHCO_2$-t-Bu,
with the following provisos:
if $R_2$ participates in the first N-substituted pyrrolidine ring, then $R_3$ also participates in the first N-substituted pyrrolidine ring;
if $R_3$ participates in the first N-substituted pyrrolidine ring, then $R_2$ also participates in the first N-substituted pyrrolidine ring;
if $R_7$ participates in the N-substituted pyrrolidine ring, then $R_8$ also participates in the N-substituted pyrrolidine ring;
if $R_8$ participates in the N-substituted pyrrolidine ring only if $R_7$ also participates in the N-substituted pyrrolidine ring;
if A and E are simultaneously NH, then B and D can not simultaneously be C; and
if E is S, then B and D are C; and
one and only one of $R_2$, $R_4$, $R_5$, $R_7$, and $R_8$ is $N^+$-alkyl $(C1–C6)_3$.

* * * * *